(12) United States Patent
Sasada

(10) Patent No.: US 9,783,736 B2
(45) Date of Patent: Oct. 10, 2017

(54) LIQUID CRYSTAL COMPOUND, LIQUID CRYSTAL COMPOSITION AND LIQUID CRYSTAL DISPLAY DEVICE

(71) Applicants: JNC CORPORATION, Tokyo (JP); JNC Petrochemical Corporation, Tokyo (JP)

(72) Inventor: Yasuyuki Sasada, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 15/203,075

(22) Filed: Jul. 6, 2016

(65) Prior Publication Data

US 2017/0009137 A1    Jan. 12, 2017

(30) Foreign Application Priority Data

Jul. 7, 2015 (JP) .................................. 2015-135918

(51) Int. Cl.

| | |
|---|---|
| *G02F 1/1333* | (2006.01) |
| *C09K 19/34* | (2006.01) |
| *C07C 43/225* | (2006.01) |
| *C07C 22/08* | (2006.01) |
| *C07C 25/13* | (2006.01) |
| *C07C 25/24* | (2006.01) |
| *C07C 381/00* | (2006.01) |
| *C09K 19/30* | (2006.01) |
| *C09K 19/06* | (2006.01) |
| *C09K 19/20* | (2006.01) |
| *C09K 19/04* | (2006.01) |
| *C09K 19/12* | (2006.01) |

(52) U.S. Cl.

CPC .......... *C09K 19/3402* (2013.01); *C07C 22/08* (2013.01); *C07C 25/13* (2013.01); *C07C 25/24* (2013.01); *C07C 43/225* (2013.01); *C07C 381/00* (2013.01); *C09K 19/063* (2013.01); *C09K 19/20* (2013.01); *C09K 19/3001* (2013.01); *C09K 19/3003* (2013.01); *C09K 19/3066* (2013.01); *C09K 19/3068* (2013.01); *C09K 2019/0466* (2013.01); *C09K 2019/122* (2013.01); *C09K 2019/301* (2013.01); *C09K 2019/3004* (2013.01); *C09K 2019/308* (2013.01); *C09K 2019/3009* (2013.01); *C09K 2019/3016* (2013.01); *C09K 2019/3019* (2013.01); *C09K 2019/3071* (2013.01); *C09K 2019/3077* (2013.01); *C09K 2019/3083* (2013.01); *C09K 2019/3422* (2013.01); *C09K 2019/3425* (2013.01)

(58) Field of Classification Search

CPC ............ C09K 19/3402; C09K 19/3068; C09K 19/3066; C09K 19/3001; C09K 19/3003; C09K 19/063; C09K 19/20; C09K 2019/3422; C09K 2019/3071; C09K 2019/0466; C09K 2019/3425; C09K 2019/3004; C09K 2019/3009; C09K 2019/301; C09K 2019/3083; C09K 2019/3077; C09K 2019/308; C09K 2019/3016; C09K 2019/122; C09K 2019/3019; G02F 1/1333; C07C 43/225; C07C 22/08; C07C 25/13; C07C 25/24; C07C 381/00

USPC .............. 252/299.01, 299.6, 299.61, 299.63; 428/1.1

See application file for complete search history.

(56) References Cited

U.S. PATENT DOCUMENTS 5,728,319 A * 3/1998 Matsui .................. C07C 43/225
                                                               252/299.63

FOREIGN PATENT DOCUMENTS

WO    WO 96-11897    4/1996

* cited by examiner

*Primary Examiner* — Geraldina Visconti
(74) *Attorney, Agent, or Firm* — Foley & Lardner LLP

(57) ABSTRACT

A solution is a compound represented by formula (1), a liquid crystal composition containing the compound and a liquid crystal display device including the composition.

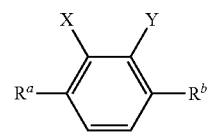

(1)

In formula (1), $R^a$ and $R^b$ are independently alkyl having 1 to 30 carbons or the like; and X and Y are independently fluoroalkyl having 1 to 5 carbons, fluoroalkoxy having 1 to 5 carbons or pentafluorosulfanil, and one of X and Y may be fluorine.

13 Claims, No Drawings

LIQUID CRYSTAL COMPOUND, LIQUID CRYSTAL COMPOSITION AND LIQUID CRYSTAL DISPLAY DEVICE

RELATED APPLICATION

This application claims priority to and the benefit of Japanese Patent Application Number JP 2015-135918, filed Jul. 7, 2015. The entire contents of the foregoing are hereby incorporated herein by reference for all purposes.

TECHNICAL FIELD

The invention relates to a liquid crystal compound, a liquid crystal composition and a liquid crystal display device. More specifically, the invention relates to a liquid crystal compound having one phenylene ring and a negative dielectric anisotropy, a liquid crystal composition containing the compound and a liquid crystal display device including the composition.

The liquid crystal display device has been widely used for a display of a personal computer, a television and so forth. The device utilizes physical properties such as optical anisotropy and dielectric anisotropy of the liquid crystal compound. The device includes an operating mode such as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode, a polymer sustained alignment (PSA) mode. In the device having the PSA mode, a liquid crystal composition containing a polymer is used. In the composition, alignment of liquid crystal molecules can be controlled by the polymer.

In such a liquid crystal display device, a liquid crystal composition having suitable physical properties is used. In order to further improve characteristics of the device, the liquid crystal compound contained in the composition preferably has physical properties described in (1) to (8) below: (1) a high stability to heat and light, (2) a high clearing point, (3) a low minimum temperature of a liquid crystal phase, (4) a small viscosity (a), (5) a suitable optical anisotropy ($\Delta$n), (6) a large negative dielectric anisotropy ($\Delta\epsilon$), (7) a suitable elastic constant, and (8) an excellent compatibility with other liquid crystal compounds.

An effect of physical properties of the liquid crystal compound on the characteristics of the device is as described below. A compound having the high stability to heat and light as described in (1) increases a voltage holding ratio of the device. Thus, a service life of the device becomes longer. A compound having the high clearing point as described in (2) extends a temperature range in which the device can be used. A compound having the low minimum temperature of the liquid crystal phase such as a nematic phase and a smectic phase as described in (3), in particular, a compound having the low minimum temperature of the nematic phase, also extends a temperature range in which the device can be used. A compound having the small viscosity as described in (4) decreases a response time of the device.

According to a design of the device, a compound having the suitable optical anisotropy as described in (5), more specifically, a compound having a large optical anisotropy or a small optical anisotropy is required. When the response time is shortened by decreasing a cell gap of the device, the compound having the large optical anisotropy is suitable. The compound having the large positive or negative dielectric anisotropy as described in (6) decreases a threshold voltage of the device. Thus, an electric power consumption of the device is reduced. On the other hand, a compound having a small dielectric anisotropy shortens the response time of the device by decreasing viscosity of the composition. The compound extends the temperature range in which the device can be used by increasing a maximum temperature of the nematic phase.

With regard to (7), a compound having a large elastic constant decreases the response time of the device. A compound having a small elastic constant decreases the threshold voltage of the device. Therefore, the suitable elastic constant is required according to the characteristics that are desirably improved. A compound having the excellent compatibility with other liquid crystal compounds as described in (8) is preferred. The reason is that the physical properties of the composition are adjusted by mixing liquid crystal compounds having different physical properties.

A variety of liquid crystal compounds having the large negative dielectric anisotropy have so far been prepared. A variety of liquid crystal compounds having the large optical anisotropy have also been prepared. The reason is that a new liquid crystal compound is expected to be excellent in physical properties that are not found in conventional compounds. The reason is that a suitable balance is expected to be obtained between at least two physical properties in the composition by adding the new compound to the liquid crystal composition. In view of such a situation, with regard to the physical properties (1) to (8) described above, a compound having excellent physical properties and a suitable balance has been desired.

The following compound is described in Example 1 of Patent literature No. 1:

CITATION LIST

Patent Literature

Patent literature No. 1: WO 1996-011897 A.

SUMMARY OF INVENTION

Technical Problem

A first object is to provide a liquid crystal compound satisfying at least one of physical properties such as a high stability to heat and light, a high clearing point (or a maximum temperature of a nematic phase), a low minimum temperature of a liquid crystal phase, a small viscosity, a suitable optical anisotropy, a large negative dielectric anisotropy, a suitable elastic constant and an excellent compatibility with other liquid crystal compounds. The object is to provide a compound having a large dielectric anisotropy in comparison with a similar compound. A second object is to provide a liquid crystal composition that contains the compound and satisfies at least one of physical properties such as a high stability to heat and light, a high maximum temperature of a nematic phase, a low minimum temperature of the nematic phase, a small viscosity, a suitable optical anisotropy, a large dielectric anisotropy, a large specific resistance and a suitable elastic constant. The object is to provide a liquid crystal composition having a suitable balance regarding at least two of the physical properties. A third object is to provide a liquid crystal display device including the composition and having a wide temperature range in which the device can be used, a short response time, a large voltage holding ratio, a low threshold voltage, a large contrast ratio and a long service life.

Solution to Problem

The invention relates to a compound represented by formula (1), a liquid crystal composition containing the compound and a liquid crystal display device including the composition:

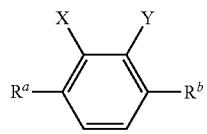
(1)

wherein, in formula (1), $R^a$ and $R^b$ are independently alkyl having 1 to 30 carbons, and in the groups, at least one piece of —CH$_2$— may be replaced by —O—, —S—, —CO— or —SiH$_2$—, at least one piece of —CH$_2$CH$_2$— may be replaced by —CH═CH— or —C≡C—, and in the monovalent groups, at least one piece of hydrogen may be replaced by fluorine or chlorine; and X and Y are independently fluoroalkyl having 1 to 5 carbons, fluoroalkoxy having 1 to 5 carbons or pentafluorosulfanil, and one of X and Y may be fluorine.

Advantageous Effects of Invention

A first advantage is to provide a liquid crystal compound satisfying at least one of physical properties such as a high stability to heat and light, a high clearing point (or a high maximum temperature of a nematic phase), a low minimum temperature of a liquid crystal phase, a small viscosity, a suitable optical anisotropy, a large negative dielectric anisotropy, a suitable elastic constant and an excellent compatibility with other liquid crystal compounds. The advantage is to provide a compound having a large dielectric anisotropy in comparison with a similar compound (see Comparative Example 1 in Table 1). A second advantage is to provide a liquid crystal composition that contains the compound and satisfies at least one of physical properties such as a high stability to heat and light, a high maximum temperature of a nematic phase, a low minimum temperature of the nematic phase, a small viscosity, a suitable optical anisotropy, a large negative dielectric anisotropy, a large specific resistance and a suitable elastic constant. The advantage is to provide a liquid crystal composition having a suitable balance regarding at least two of the physical properties. A third advantage is to provide a liquid crystal display device including the composition and having a wide temperature range in which the device can be used, a short response time, a large voltage holding ratio, a low threshold voltage, a large contrast ratio and a long service life.

DESCRIPTION OF EMBODIMENTS

Usage of terms herein is as described below. Terms "liquid crystal compound," "liquid crystal composition" and "liquid crystal display device" may be occasionally abbreviated as "compound," "composition" and "device," respectively. "Liquid crystal compound" is a generic term for a compound having a liquid crystal phase such as a nematic phase or a smectic phase, and also a compound having no liquid crystal phase but to be added for the purpose of adjusting physical properties such as a maximum temperature, a minimum temperature, viscosity and dielectric anisotropy. The compound has a six-membered ring such as 1,4-cyclohexylene, and has a rod-like molecular structure. "Liquid crystal display device" is a generic term for a liquid crystal display panel and a liquid crystal display module. "Polymerizable compound" is a compound to be added for the purpose of forming a polymer in the composition.

The liquid crystal composition is prepared by mixing a plurality of liquid crystal compounds. An additive is added to the composition for the purpose of further adjusting the characteristics. The additive such as an optically active compound, an antioxidant, an ultraviolet light absorber, a light stabilizer, a heat stabilizer, a dye, an antifoaming agent, a polymerizable compound, a polymerization initiator and a polymerization inhibitor is added as necessary. The liquid crystal compound and the additive are mixed in such a procedure. Even if the additive is added, a proportion (amount of addition) of the liquid crystal compound is expressed in terms of weight percent (% by weight) based on the weight of the liquid crystal composition containing no additive. A proportion (amount of addition) of the additive is expressed in terms of weight percent (% by weight) based on the weight of the liquid crystal composition containing no additive. Weight parts per million (ppm) may be occasionally used. A proportion of the polymerization initiator or the polymerization inhibitor is exceptionally expressed based on the weight of the polymerizable compound.

"Clearing point" is a transition temperature between a liquid crystal phase and an isotropic phase in the liquid crystal compound. "Minimum temperature of the liquid crystal phase" means a transition temperature between a solid and the liquid crystal phase (the smectic phase, the nematic phase or the like) in the liquid crystal compound. "Maximum temperature of the nematic phase" means a transition temperature between the nematic phase and the isotropic phase in a mixture of the liquid crystal compound and a base liquid crystal, or the liquid crystal composition, and may be occasionally abbreviated as "maximum temperature." "Minimum temperature of the nematic phase" may be occasionally abbreviated as "minimum temperature". An expression "increases the dielectric anisotropy" means that the value positively increases for the composition having a positive dielectric anisotropy, and that the value negatively increases for the composition having a negative dielectric anisotropy.

A compound represented by formula (1) may be occasionally abbreviated as "compound (1)." At least one compound selected from the group of compounds represented by formula (1) may be occasionally abbreviated as "compound (1)." "Compound (1)" means one compound or a mixture of two compounds or a mixture of three or more compounds represented by formula (1). A same rule applies also to any other compound represented by any other formula. In formulas (1) to (15), a symbol $A^1$, $B^1$, $C^1$ or the like surrounded by a hexagonal shape corresponds to ring $A^1$, ring $B^1$, ring $C^1$ or the like, respectively. The hexagonal shape represents a six-membered ring such as cyclohexane or benzene. The hexagonal shape may occasionally represents a condensed ring such as naphthalene or a bridged ring such as adamantane.

A symbol of terminal group $R^{11}$ is used for a plurality of compounds in chemical formulas. In the compounds, two groups represented by two pieces of arbitrary $R^{11}$ may be identical or different. In one case, for example, $R^{11}$ of compound (2) is ethyl and $R^{11}$ of compound (3) is ethyl. In another case, $R^{11}$ of compound (2) is ethyl and $R^{11}$ of compound (3) is propyl. A same rule also applies to a symbol such as $R^{12}$, $R^{13}$ and $Z^{11}$. In compound (15), when i is 2, two pieces of ring $E^1$ exist. In the compound, two groups represented by two pieces of ring $E^1$ may be identical or different. A same rule also applies to two pieces of arbitrary ring $E^1$ when i is larger than 2. A same rule also applies to any other symbols.

An expression "at least one piece of 'A'" means that the number of 'A' is arbitrary. An expression "at least one piece of 'A' may be replaced by 'B'" means that, when the number of 'A' is 1, a position of 'A' is arbitrary, and also when the number of 'A' is 2 or more, positions thereof can be selected without limitation. A same rule also applies to an expression "at least one piece of 'A' is replaced by 'B'." An expression "at least one piece of 'A' may be replaced by 'B', 'C' or 'D'" means a case where at least one piece of arbitrary 'A' is replaced by 'B', a case where at least one piece of arbitrary 'A' is replaced by 'C', and a case where at least one piece of arbitrary 'A' is replaced by 'D', and also a case where a plurality of pieces of 'A' are replaced by at least two pieces of 'B', 'C' and/or 'D'. For example, an expression "alkyl in which at least one piece of —$CH_2$— may be replaced by —O— or —CH=CH—" includes alkyl, alkoxy, alkoxyalkyl, alkenyl, alkoxyalkenyl and alkenyloxyalkyl. In addition, a case where replacement of two successive pieces of —$CH_2$— by —O— results in forming —O—O— is not preferred. In the alkyl or the like, a case where replacement of —$CH_2$— of a methyl group (—$CH_2$—H) by —O— results in forming —O—H is not preferred, either.

"Halogen" means fluorine, chlorine, bromine and iodine. Preferred halogen is fluorine and chlorine. Further preferred halogen is fluorine. Alkyl has a straight or a branched chain, but includes no cyclic alkyl. In general, straight-chain alkyl is preferred to branched-chain alkyl. A same rule also applies to a terminal group such as alkoxy and alkenyl. "Fluoroalkyl" means alkyl in which at least one piece of hydrogen is replaced by fluorine. "Fluoroalkyl" is a generic term for monofluoroalkyl, polyfluoroalkyl and perfluoroalkyl. A same rule also applies to fluoroalkoxy or the like. With regard to a configuration of 1,4-cyclohexylene, trans is generally preferred to cis. Then, 2-fluoro-1,4-phenylene means two divalent groups described below. In a chemical formula, fluorine may be leftward (L) or rightward (R). A same rule also applies to an asymmetrical divalent group formed by removing two pieces of hydrogen from a ring such as tetrahydropyran-2,5-diyl.

The invention includes items described below.

Item 1. A compound represented by formula (1):

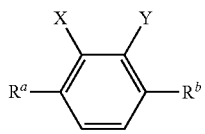

(1)

wherein, in formula (1), $R^a$ and $R^b$ are independently alkyl having 1 to 30 carbons, and in the groups, at least one piece of —$CH_2$— may be replaced by —O—, —S—, —CO— or —$SiH_2$—, at least one piece of —$CH_2CH_2$— may be replaced by —CH=CH— or —C≡C—, and in the monovalent groups, at least one piece of hydrogen may be replaced by fluorine or chlorine; and X and Y are independently fluoroalkyl having 1 to 5 carbons, fluoroalkoxy having 1 to 5 carbons or pentafluorosulfanil, and one of X and Y may be fluorine.

Item 2. The compound according to item 1, wherein, in formula (1), $R^a$ and $R^b$ are independently alkyl having 1 to 20 carbons, and in the groups, at least one piece of —$CH_2$— may be replaced by —O— or —S—, one or two pieces of —$CH_2CH_2$— may be replaced by —CH=CH— or —C≡C—, and in the monovalent groups, at least one piece of hydrogen may be replaced by fluorine or chlorine; and X and Y are independently fluoroalkyl having 1 to 3 carbons, fluoroalkoxy having 1 to 3 carbons or pentafluorosulfanil, and one of X and Y may be fluorine.

Item 3. The compound according to item 1, wherein, in formula (1), $R^a$ and $R^b$ are independently alkyl having 1 to 15 carbons, and in the groups, at least one or two pieces of —$CH_2$— may be replaced by —O—, one piece of —$CH_2CH_2$— may be replaced by —CH=CH— or —C≡C—, and in the monovalent groups, at least one piece of hydrogen may be replaced by fluorine; and X is fluorine, fluoroalkyl having 1 to 3 carbons, fluoroalkoxy having 1 to 3 carbons or pentafluorosulfanil, and Y is fluoroalkyl having 1 to 3 carbons.

Item 4. The compound according to item 1, represented by formula (1a):

(1a)

wherein, in formula (1a), $R^a$ and $R^b$ are independently alkyl having 1 to 10 carbons or alkoxy having 1 to 10 carbons; and Y is —$CF_3$, —$CF_2H$, —$CFH_2$ or fluorine.

Item 5. The compound according to item 4, wherein, in formula (1a), $R^a$ is alkyl having 1 to 10 carbons, and $R^b$ is alkoxy having 1 to 10 carbons; and Y is —$CF_3$.

Item 6. The compound according to item 1, represented by formula (1b):

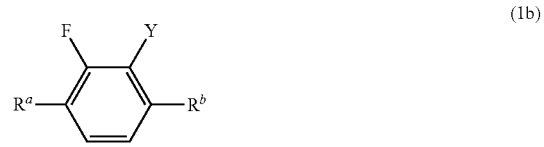

(1b)

wherein, in formula (1b), $R^a$ and $R^b$ are independently alkyl having 1 to 10 carbons or alkoxy having 1 to 10 carbons; and Y is —$CF_3$, —$CF_2H$ or —$CFH_2$.

Item 7. The compound according to item 6, wherein, in formula (1b), $R^a$ and $R^b$ are independently alkoxy having 1 to 10 carbons; and Y is —$CF_3$.

Item 8. A liquid crystal composition containing at least one compound according to any one of items 1 to 7.

Item 9. The liquid crystal composition according to item 8, containing at least one compound selected from the group of compounds represented by formulas (2) to (4):

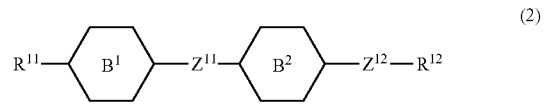

(2)

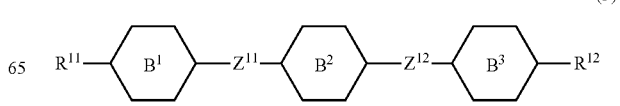

(3)

-continued (4)

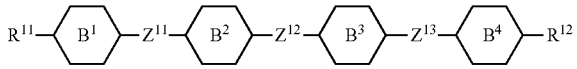

wherein, in formulas (2) to (4), $R^{11}$ and $R^{12}$ are independently alkyl having 1 to 10 carbons or alkenyl having 2 to 10 carbons, and in the groups, at least one piece of —CH$_2$— may be replaced by —O—, and in the monovalent groups, at least one piece of hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —COO—, —CH$_2$CH$_2$—, —CH=CH— or —C≡C—.

Item 10. The liquid crystal composition according to item 8 or 9, further containing at least one compound selected from the group of compounds represented by formulas (5) to (11):

1,4-phenylene in which at least one piece of hydrogen is replaced by fluorine, tetrahydropyran-2,5-diyl or decahydronaphthalene-2,6-diyl;

ring $C^5$ and ring $C^6$ are independently 1,4-cyclohexylene, 1,4-cyclohexenylene, 1,4-phenylene, tetrahydropyran-2,5-diyl or decahydronaphthalene-2,6-diyl;

$Z^{14}$, $Z^{15}$, $Z^{16}$ and $Z^{17}$ are independently a single bond, —COO—, —CH$_2$O—, —OCF$_2$—, —CH$_2$CH$_2$— or —OCF$_2$CH$_2$CH$_2$—;

$L^{11}$ and $L^{12}$ are independently fluorine or chlorine;

$S^{11}$ is hydrogen or methyl;

X is —CHF— or —CF$_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 11. The liquid crystal composition according to any one of items 8 to 10, further containing at least one compound selected from the group of compounds represented by formulas (12) to (14):

(5)

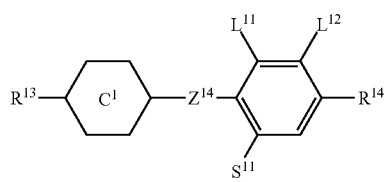

(6)

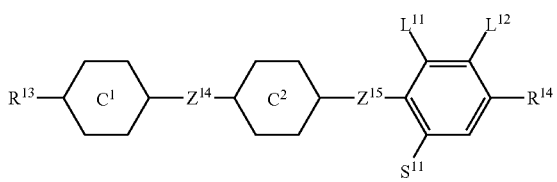

(7)

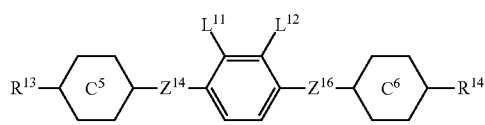

(8)

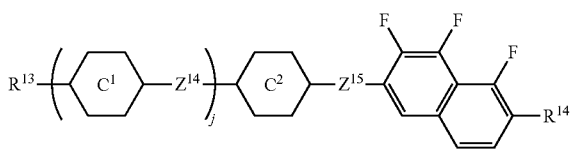

(9)

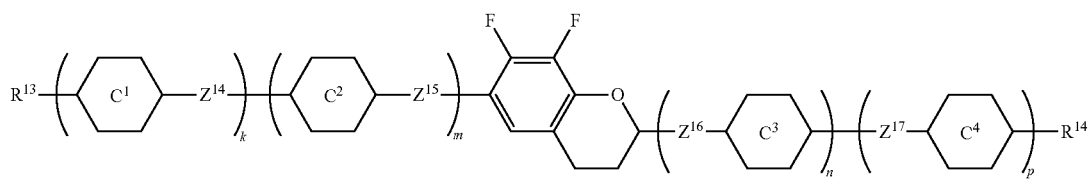

(10)

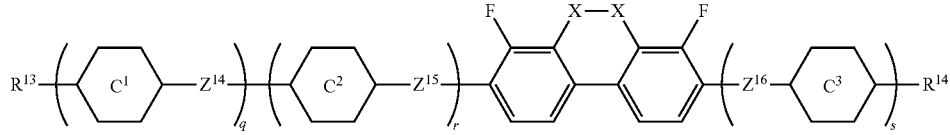

(11)

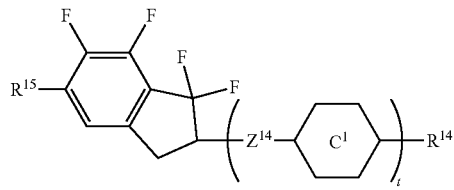

wherein, in formulas (5) to (11), $R^{13}$, $R^{14}$ and $R^{15}$ are independently alkyl having 1 to 10 carbons or alkenyl having 2 to 10 carbons, and in the groups, at least one piece of —CH$_2$— may be replaced by —O—, and in the monovalent groups, at least one piece of hydrogen may be replaced by fluorine, and $R^{15}$ may be hydrogen or fluorine;

ring $C^1$, ring $C^2$, ring $C^3$ and ring $C^4$ are independently 1,4-cyclohexylene, 1,4-cyclohexenylene, 1,4-phenylene, (12)

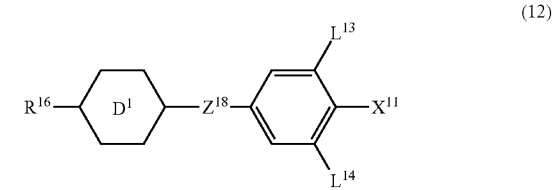

-continued

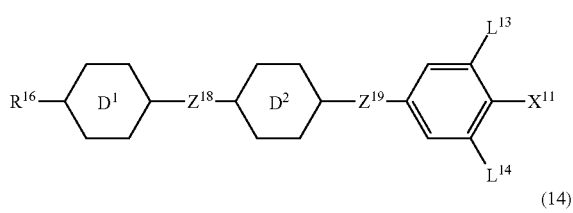

(13)

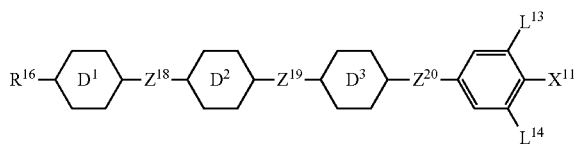

(14)

wherein, in formulas (12) to (14), $R^{16}$ is alkyl having 1 to 10 carbons or alkenyl having 2 to 10 carbons, and in the groups, at least one piece of —$CH_2$— may be replaced by —O—, and in the monovalent groups, at least one piece of hydrogen may be replaced by fluorine;

$X^{11}$ is fluorine, chlorine, —$CF_3$, —$CHF_2$, —$CH_2F$, —$OCF_3$, —$OCHF_2$, —$OCF_2CHF_2$ or —$OCF_2CHFCF_3$;

ring $D^1$, ring $D^2$ and ring $D^3$ are independently 1,4-cyclohexylene, 1,4-phenylene, 1,4-phenylene in which at least one piece of hydrogen is replaced by fluorine, tetrahydropyran-2,5-diyl, 1,3-dioxane-2,5-diy or pyrimidine-2,5-diyl;

$Z^{18}$, $Z^{19}$ and $Z^{20}$ are independently a single bond, —COO—, —$CH_2O$—, —$CF_2O$—, —$OCF_2$—, —$CH_2CH_2$—, —CH=CH—, —C≡C— or —$(CH_2)_4$—; and $L^{13}$ and $L^{14}$ are independently hydrogen or fluorine.

Item 12. The liquid crystal composition according to any one of items 8 to 11, further containing at least one compound selected from the group of compounds represented by formula (15):

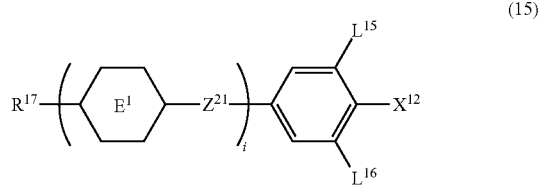

(15)

wherein, in formula (15), $R^{12}$ is alkyl having 1 to 10 carbons or alkenyl having 2 to 10 carbons, and in the groups, at least one piece of —$CH_2$— may be replaced by —O—, and in the monovalent groups, at least one piece of hydrogen may be replaced by fluorine;

$X^{12}$ is —C≡N or —C≡C—C≡N;

ring $E^1$ is 1,4-cyclohexylene, 1,4-phenylene, 1,4-phenylene in which at least one piece of hydrogen is replaced by fluorine, tetrahydropyran-2,5-diyl, 1,3-dioxane-2,5-diyl or pyrimidine-2,5-diyl;

$Z^{21}$ is a single bond, —COO—, —$CH_2O$—, —$CF_2O$—, —$OCF_2$—, —$CH_2CH_2$— or —C≡C—;

$L^{15}$ and $L^{16}$ are independently hydrogen or fluorine; and i is 1, 2, 3 or 4.

Item 13. A liquid crystal display device, including the liquid crystal composition according to any one of items 8 to 12.

The invention further includes the following items: (a) the liquid crystal composition, further containing one, two or at least three of additives selected from the group of additives such as a polymerizable compound, a polymerization initiator, a polymerization inhibitor, a optically active compound, an antioxidant, an ultraviolet light absorber, a light stabilizer, a heat stabilizer, a dye, and an antifoaming agent; (b) the liquid crystal composition having a maximum temperature of a nematic phase of 70° C. or more, an optical anisotropy (measured at 25° C.) of 0.08 or more at a wavelength of 589 nanometers and dielectric anisotropy (measured at 25° C.) of −2 or less at a frequency of 1 kHz; (c) the liquid crystal display device, wherein an operating mode of the device is a TN mode, an ECB mode, an OCB mode, an IPS mode or an FPA mode, and a driving mode in the device includes an active matrix (AM) mode; and (d) the liquid crystal display device having a PSA mode, prepared by using the above liquid crystal composition further containing the polymerizable compound.

An aspect of compound (1), a synthesis method of compound (1), the liquid crystal composition and the liquid crystal display device are described in the order.

1. Aspect of Compound (1)

Compound (1) of the invention has a feature of having one phenylene ring. The compound has a negative dielectric anisotropy. The compound has an excellent compatibility with other liquid crystal compounds. A composition containing the compound is physically or chemically stable under conditions in which a device including the composition is ordinarily used. Even if the composition is stored under conditions in which a device including the composition is ordinarily used, no compound is precipitated as a crystal (or smectic phase). The compound has a suitable optical anisotropy and a suitable dielectric anisotropy.

Preferred examples of terminal groups $R^a$ and $R^b$ and side chain groups X and Y in compound (1) are as described below. A same rule also applies to a subordinate formula of compound (1). In compound (1), physical properties can be arbitrarily adjusted by suitably selecting the groups, and therefore compound (1) may also contain an isotope such as $^2H$ (deuterium) and $^{13}C$ in an amount larger than an amount of natural abundance because no significant difference is in the physical properties of the compound. Moreover, a symbol of compound (1) is defined in a manner identical with the definitions in item 1.

(1)

In formula (1), $R^a$ and $R^b$ are independently alkyl having 1 to 30 carbons, and in the groups, at least one piece of —$CH_2$— may be replaced by —O—, —S—, —CO— or —$SiH_2$— at least one piece of —$CH_2CH_2$— may be replaced by —CH=CH— or —C≡C—, and in the monovalent groups, at least one piece of hydrogen may be replaced by fluorine or chlorine.

Preferred $R^a$ or $R^b$ includes hydrogen, alkyl, alkoxy, alkoxyalkyl, alkoxyalkoxy, alkylthio, alkylthioalkoxy, acyl, acyl alkyl, acyloxy, acyloxy alkyl, alkoxycarbonyl, alkoxycarbonylalkyl, alkenyl, alkenyloxy, alkenyloxyalkyl, alkoxyalkenyl, alkynyl, alkynyloxy, silaalkyl and disilaalkyl. The groups in which at least one piece of hydrogen is replaced by fluorine and/or chlorine are also preferred. The groups in which at least one piece of hydrogen is replaced by fluorine are further preferred. In the groups, a straight chain is preferred to a branched chain. Even if $R^a$ or $R^b$ is the branched chain group, when the group is optically active, such a group is preferred. Further preferred $R^a$ or $R^b$ is alkyl, alkoxy, alkoxyalkyl, alkenyl, fluoroalkyl and fluoroalkoxy.

A preferred configuration of —CH═CH— in the alkenyl depends on a position of a double bond. Trans is preferred in alkenyl such as 1-propenyl, 1-butenyl, 1-pentenyl, 1-hexenyl, 3-pentenyl and 3-hexenyl. Cis is preferred in alkenyl such as 2-butenyl, 2-pentenyl and 2-hexenyl.

Specific $R^a$ or $R^b$ includes methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxy propyl, propoxy methyl, butoxy methyl, pentoxy methyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, 1-propynyl or 1-pentenyl.

Specific $R^a$ or $R^b$ includes 2-fluoroethyl, 3-fluoropropyl, 2,2,2-trifluoroethyl, 2-fluorovinyl, 2,2-difluorovinyl, 2-fluoro-2-vinyl, 3-fluoro-1-propenyl, 3,3,3-trifluoro-1-propenyl, 4-fluoro-1-propenyl or 4,4-difluoro-3-butenyl.

Further preferred $R^a$ or $R^b$ includes ethyl, propyl, butyl, pentyl, methoxy, ethoxy, propoxy, butoxy, pentyloxy, methoxymethyl, ethoxymethyl, propoxy methyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyl oxy or 2-pentenyl oxy. Most preferred $R^a$ or $R^b$ includes ethyl, propyl, butyl, pentyl, methoxy, ethoxy, propoxy or methoxymethyl.

In formula (1), X and Y are independently fluoroalkyl having 1 to 5 carbons, fluoroalkoxy having 1 to 5 carbons or pentafluorosulfanil (—SF$_5$), and one of X and Y may be fluorine. Fluoroalkyl means monofluoroalkyl, polyfluoroalkyl and perfluoroalkyl. Fluoroalkoxy means monofluoroalkoxy, polyfluoroalkoxy and perfluoroalkoxy.

Preferred X or Y includes fluoroalkyl, fluoroalkoxy or fluorine. Further preferred X or Y includes fluoroalkoxy or fluorine. Preferred fluoroalkyl includes polyfluoroalkyl or perfluoroalkyl. Further preferred fluoroalkyl includes perfluoroalkyl. Preferred fluoroalkoxy includes polyfluoroalkoxy or perfluoroalkoxy. Further preferred fluoroalkoxy includes perfluoroalkoxy. A preferred number of carbons is 1 to 3. A further preferred number of carbons is 1 or 2. A most preferred number of carbons is 1.

Preferred X or Y includes fluorine —CF$_3$, —CHF$_2$, —CH$_2$F, —CF$_2$CF$_3$, —CF$_2$CHF$_2$, —CF$_2$CH$_2$F, —CHFCF$_3$, —CH$_2$CF$_3$, —CF$_2$CF$_2$CF$_3$, —CF$_2$CHFCF$_3$, —CHFCF$_2$CF$_3$, —OCF$_3$, —OCHF$_2$, —OCH$_2$F, —OCF$_2$CF$_3$, —OCF$_2$CHF$_2$, —OCF$_2$CH$_2$F, —OCHFCF$_3$, —OCH$_2$CF$_3$, —OCF$_2$CF$_2$CF$_3$, —OCF$_2$CHFCF$_3$ or —OCHFCF$_2$CF$_3$.

Further preferred X or Y includes fluorine, —CF$_3$, —CHF$_2$, —CH$_2$F, —CF$_2$CF$_3$, —CF$_2$CHF$_2$, —CHFCF$_3$, —CH$_2$CF$_3$, —CF$_2$CF$_2$CF$_3$, —CF$_2$CHFCF$_3$, —CHFCF$_2$CF$_3$, —OCF$_3$, —OCHF$_2$ or —OCH$_2$F. Particularly preferred X or Y includes fluorine, —CF$_3$, —CHF$_2$ or —CH$_2$F. Most preferred X or Y includes fluorine or —CF$_3$.

Physical properties such as the optical anisotropy and the dielectric anisotropy can be arbitrarily adjusted by suitably selecting terminal group and side chain groups X and Y of compound (1). An effect of the groups on the physical properties of compound (1) is described below.

In compound (1), when $R^a$ or $R^b$ has a straight chain, the temperature range of the liquid crystal phase is wide, and the viscosity is small. When $R^a$ or $R^b$ has the branched chain, the compatibility with other liquid crystal compounds is excellent. A compound in which $R^a$ or $R^b$ is an optically active group is useful as a chiral dopant. A reverse twisted domain to be generated in the device can be prevented by adding the compound to the composition. A compound in which $R^a$ or $R^b$ is not the optically active group is useful as a component of the composition. When $R^a$ or $R^b$ is alkenyl, a preferred configuration depends on a position of a double bond. An alkenyl compound having the preferred configuration has a high maximum temperature or a wide temperature range of the liquid crystal phase. A detailed description is found in Mol. Cryst. Liq. Cryst., 1985, 131, 109 and Mol. Cryst. Liq. Cryst., 1985, 131, 327.

In formula (1), a compound in which X or Y is fluorine, —CF$_3$, —CHF$_2$ or —CH$_2$F is preferred. In view of a large dielectric anisotropy, —CF$_3$ is preferred. In view of a small viscosity, fluorine is preferred.

A preferred example of compound (1) includes compound (1a) or compound (1b). In the compounds, a symbol is defined in a manner identical with the definitions in the items above.

2. Synthesis of Compound (1)

A method for synthesizing compound (1) is described. Compound (1) can be prepared by suitably combining methods in synthetic organic chemistry. A methods for introducing an objective terminal group, ring and bonding group into a starting material is described in "Houben-Wyle" (Methoden der Organische Chemie, Georg-Thieme Verlag, Stuttgart), "Organic Syntheses" (John Wily & Sons, Inc.), "Organic Reactions" (John Wily & Sons Inc.), "Comprehensive Organic Synthesis" (Pergamon Press), "New Experimental Chemistry Course (Shin Jikken Kagaku Koza in Japanese)" (Maruzen Co., Ltd.) or the like.

A method for forming 2,3-disubstituted-1,4-phenylene is described. A starting material of a ring such as 2-fluoro-3-trifluoromethyl-1,4-phenylene is commercially available, or a synthetic method thereof is well known. Thus, compound (1-1), compound (1-1') and compounds (1-2) to (1-6) described below are described. The compounds can be converted into compound (1) by using a conventional method.

(1) Synthesis of Compound (1-1)

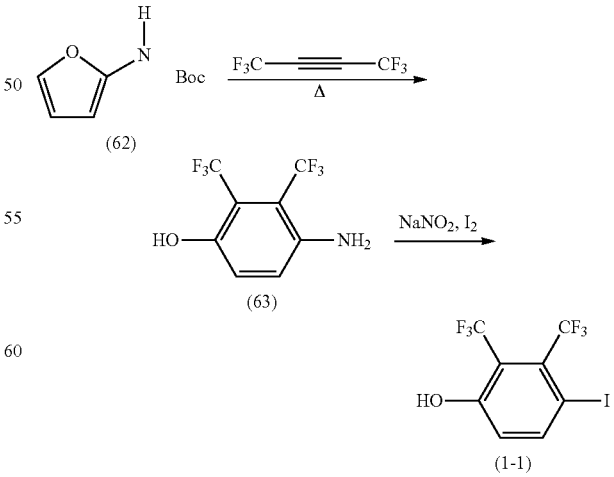

Then, 2,3-(bistrifluoromethyl)phenylene is formed by a method described in Org. Lett., 2000, 2(21), 3345. Aniline

(63) is prepared by allowing furan (62) to react with 1,1,1,4,4,4-hexafluoro-2-butyne by a Diels Alder reaction at a high temperature. Iodide (1-1) is obtained by performing a Sandmeyer reaction to the compound, according to a method described in Org. Synth. Coll., Vol. 2, 1943, 355.

(2) Synthesis of Compound (1-1')

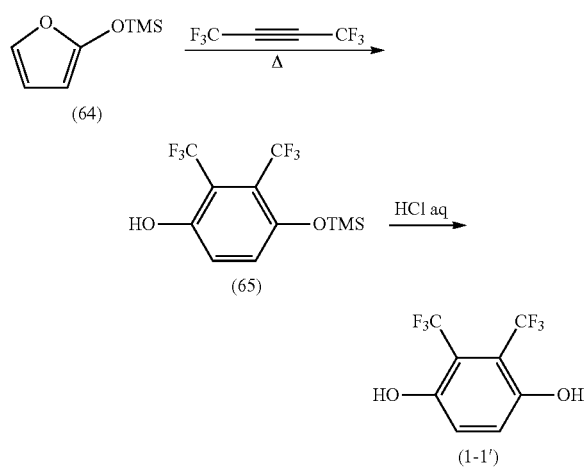

In a similar manner, phenol (65) is prepared by reacting furan (64) with 1,1,1,4,4,4-hexafluoro-2-butyne by a Diels Alder reaction at a high temperature. Hydroquinone (1-1') is obtained by allowing hydrochloric acid to react with the compound and then deprotecting the resulting material.

(3) Synthesis of Compound (1-2)

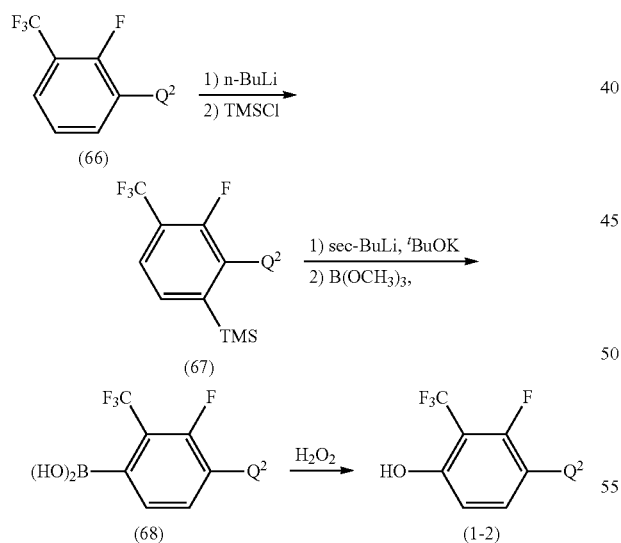

$Q^2$ in compound (66) means a monovalent group. Compound (67) is obtained by protecting a hydroxyl group of the compound with suitable protective group P (for example, a trimethylsilyl group). Boric acid (68) is obtained by acting s-butyllithium on compound (67) in the presence of t-BuOK, and subsequently acting trimethyl borate on the resulting material. Phenol (1-2) is obtained by oxidizing the compound with 30% hydrogen peroxide water.

(4) Synthesis of Compound (1-3)

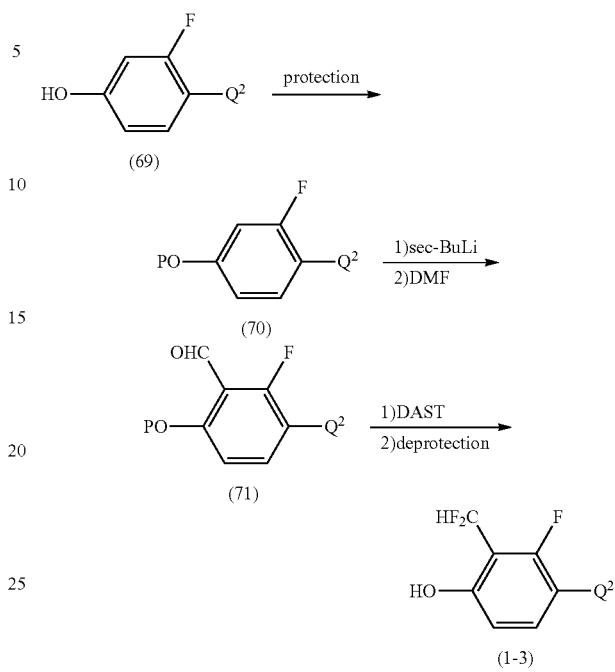

$Q^2$ in compound (69) means a monovalent group. Compound (70) is obtained by protecting a hydroxyl group of the compound with suitable protective group P. Aldehyde (71) is obtained by acting s-butyllithium on compound (70), and subsequently allowing N,N-dimethylformamide (DMF) to react with the resulting material. Phenol (1-3) is obtained by fluorinating the compound with diethylaminosulfur trifluoride (DAST), and subsequently deprotecting the resulting material.

(5) Synthesis of Compound (1-4)

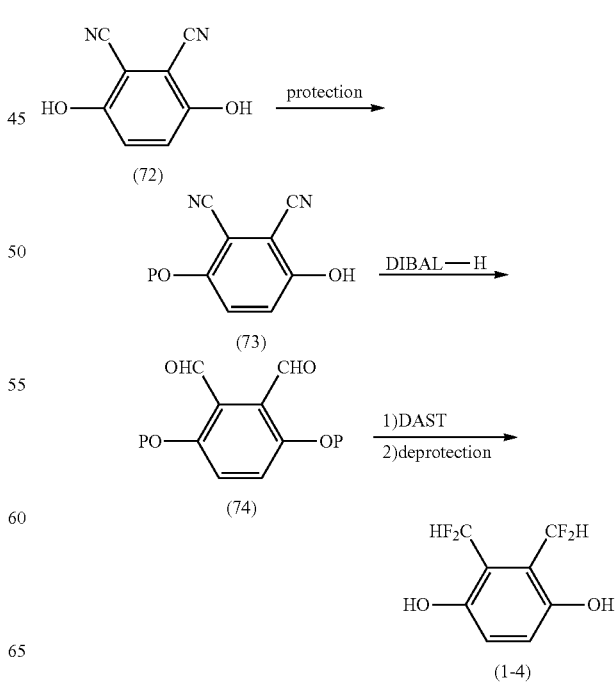

Compound (73) is obtained by protecting a hydroxyl group of the compound with suitable protective group P. Aldehyde (74) is obtained by reducing compound (73) with diisobutylaluminum hydride (DIBAL-H). Phenol (1-4) is obtained by fluorinating the compound with diethylaminosulfur trifluoride (DAST), and subsequently deprotecting the resulting material.

(6) Synthesis of Compound (1-5)

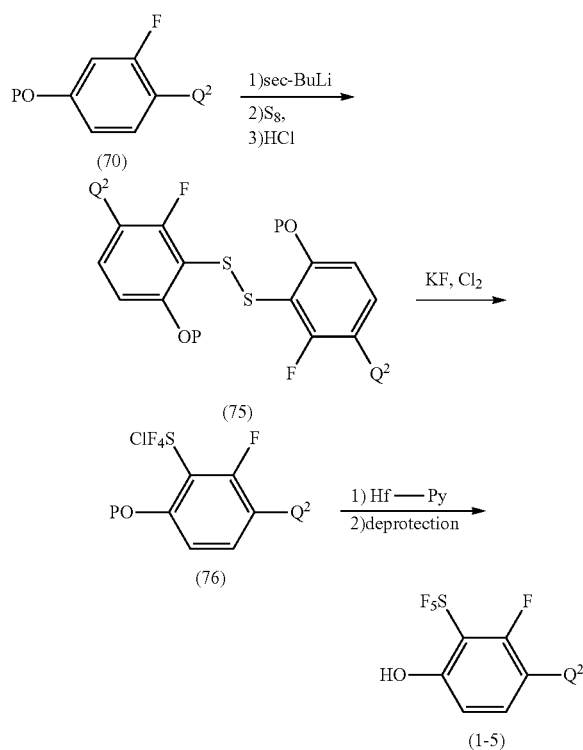

$Q^2$ in compound (70) is a monovalent group and P is a protective group of a hydroxyl group. Compound (75) being disulfide is obtained by acting s-butyllithium on the compound, and then allowing sulfur to react with the resulting material. Compound (76) is derived from the compound by allowing gaseous chlorine to react with the compound in the presence of potassium fluoride. Phenol (1-5) is obtained by fluorinating the compound by using a hydrogen fluoride-pyridine complex, and subsequently deprotecting the resulting material.

(7) Synthesis of Compound (1-6)

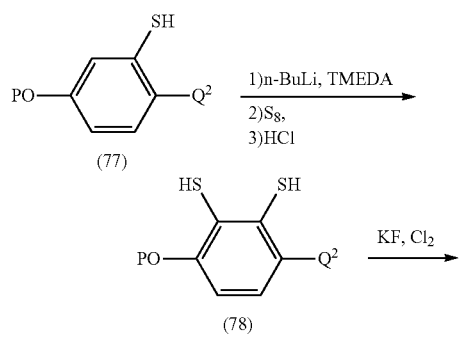

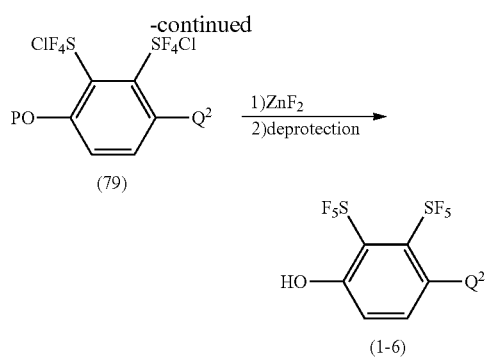

Dithiol (78) is obtained by acting n-butyllithium on thiol (77) in which a hydroxyl group is protected with suitable protective group P in the presence of tetramethylethylenediamine (TMEDA), and then allowing sulfur to react with the resulting material. Compound (79) is derived the compound by allowing reacting gaseous chlorine to react with the compound in the presence of potassium fluoride. Phenol (1-6) is obtained by fluorinating the compound by using zinc fluoride, and subsequently deprotecting the resulting material.

3. Liquid Crystal Composition 3-1. Component Compound

A liquid crystal composition of the invention is described. The composition contains at least one compound (1) as component (a). Compound (1) is useful for increasing a maximum temperature of the composition. Compound (1) is useful for increasing the dielectric anisotropy of the composition. The composition may contain two, three or more compounds (1). A component of the composition may include only compound (1). In order to develop excellent physical properties, the composition preferably contains at least one compound (1) in the range of about 1% by weight to about 99% by weight. In a composition having a negative dielectric anisotropy, a preferred content of compound (1) is in the range of about 5% by weight to about 60% by weight. In a composition having a positive dielectric anisotropy, a preferred content of compound (1) is about 30% by weight or less.

The liquid crystal composition of the invention contains compound (1) as component (a) and preferably further contains a liquid crystal compound selected from components (b) to (e).

| Component of composition | Component compound | Dielectric anisotropy |
|---|---|---|
| Component (a) | Compound (1) | Negatively large |
| Component (b) | Compound (2) to compound (4) | Small |
| Component (c) | Compound (5) to compound (11) | Negatively large |
| Component (d) | Compound (12) to compound (14) | Positively large |
| Component (e) | Compound (15) | Positively large |

The composition may contain other liquid crystal compounds different from compounds (2) to (15). The composition needs not contain other liquid crystal compounds. When the composition is prepared, the component is preferably selected from components (b) to (e) by taking into account a positive or negative dielectric anisotropy and magnitude of the dielectric anisotropy. A composition in which the components are suitably selected has a high stability to heat and light, a high maximum temperature, a low minimum temperature, a small viscosity, a suitable optical anisotropy (namely, a large optical anisotropy or a small optical anisotropy), a large dielectric anisotropy, a large specific resistance, and a suitable elastic constant (namely, a large elastic constant or a small elastic constant).

Component (b) includes a compound in which two terminal groups are alkyl or the like. Preferred examples of component (b) include compounds (2-1) to (2-11), compounds (3-1) to (3-19) and compounds (4-1) to (4-7). In the compound of component (b), $R^{11}$ and $R^{12}$ are independently alkyl having 1 to 10 carbons or alkenyl having 2 to 10 carbons, and in the groups, at least one piece of —CH$_2$— may be replaced by —O—, and in the monovalent groups, at least one piece of hydrogen may be replaced by fluorine.

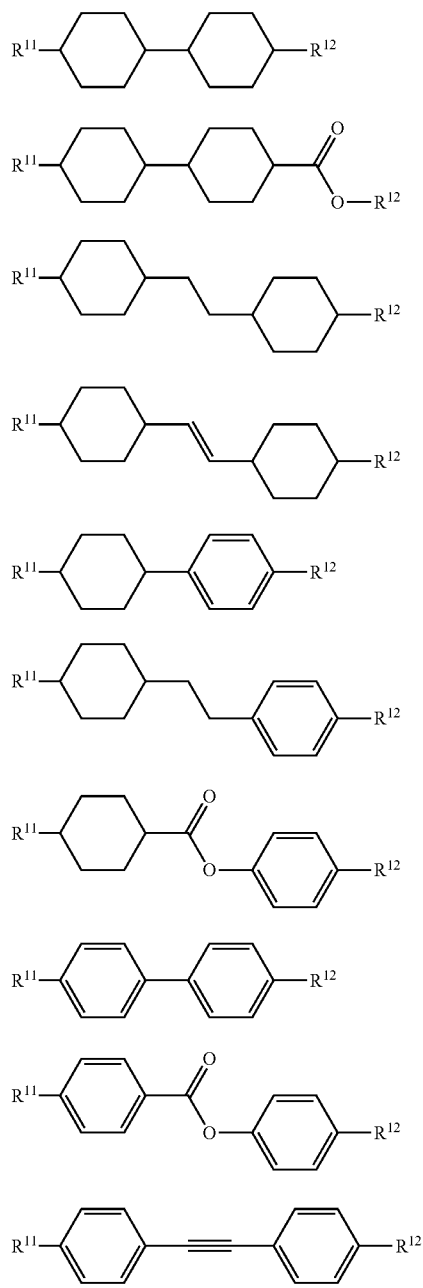

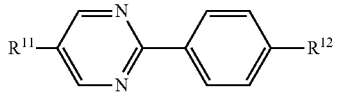
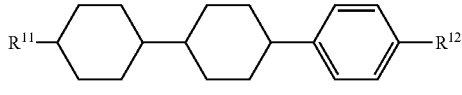
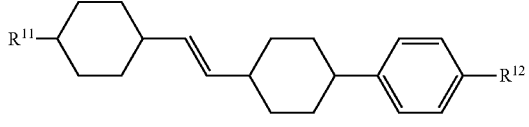
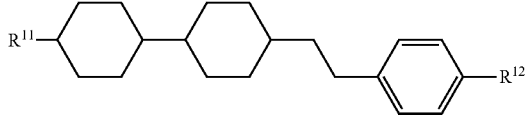
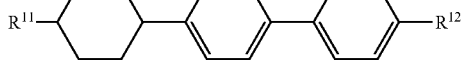
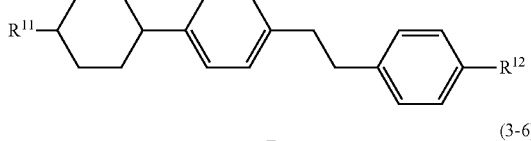
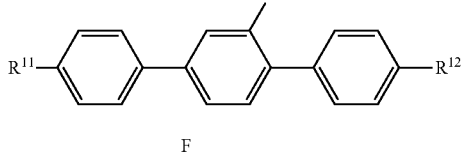
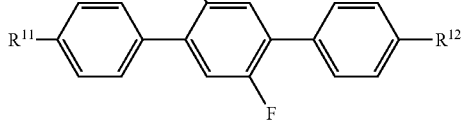
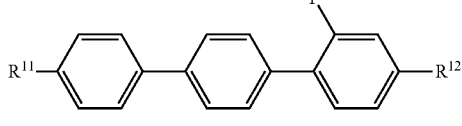
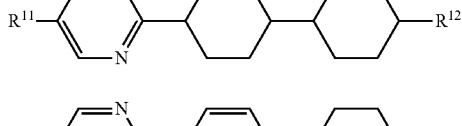
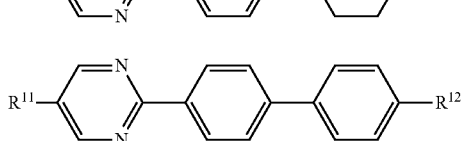

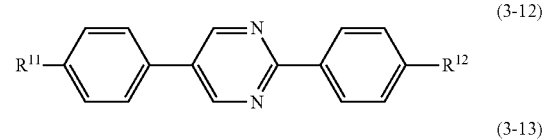
(3-12)

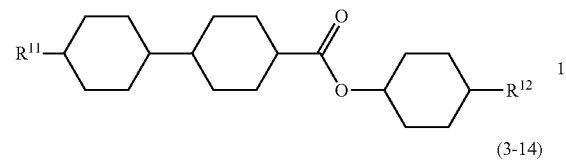
(3-13)

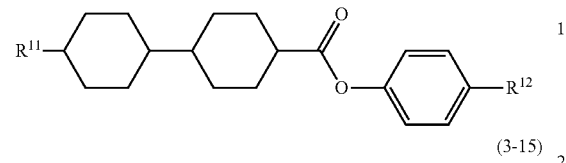
(3-14)

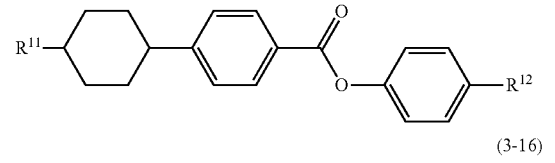
(3-15)

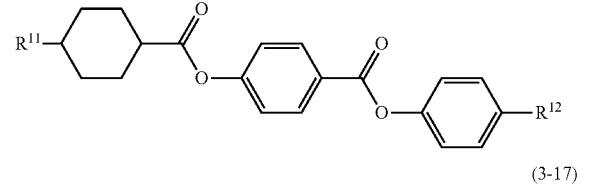
(3-16)

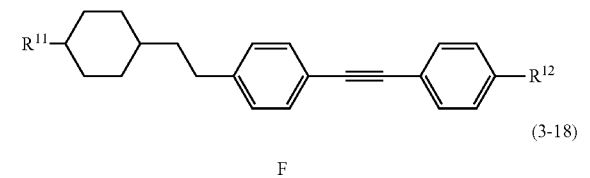
(3-17)

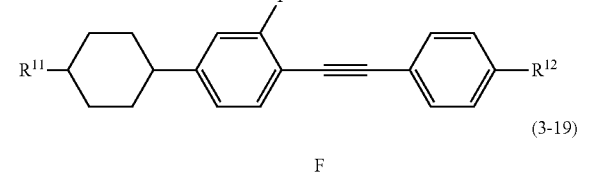
(3-18)

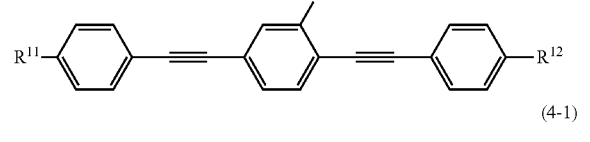
(3-19)

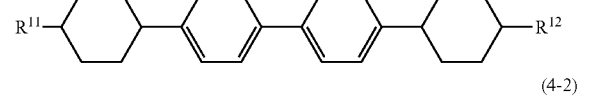
(4-1)

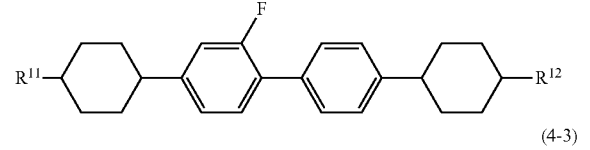
(4-2)

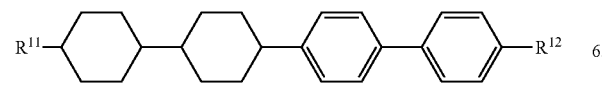
(4-3)

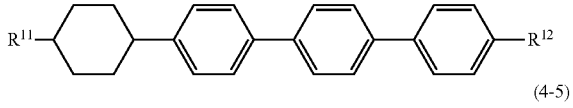
(4-4)

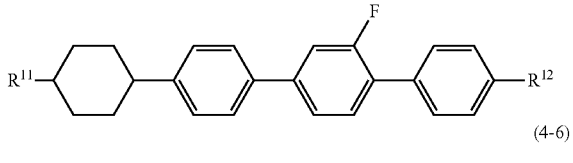
(4-5)

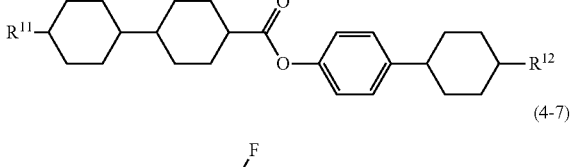
(4-6)

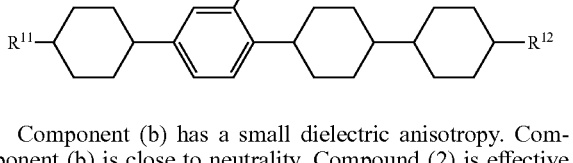
(4-7)

Component (b) has a small dielectric anisotropy. Component (b) is close to neutrality. Compound (2) is effective in reducing the viscosity or adjusting the optical anisotropy. Compounds (3) and (4) are effective in extending the temperature range of the nematic phase by increasing the maximum temperature, or in adjusting the optical anisotropy.

Accordingly as a content of compounds (b) is increased, the viscosity of the composition decreases, and the dielectric anisotropy decreases. Thus, as long as a desired value of threshold voltage of the device is met, the content is preferably as large as possible. When a composition for the IPS mode, the VA mode or the like is prepared, the content of compounds (2) to (4) is preferably about 30% by weight or more, and further preferably, about 40% by weight or more, based on the weight of the liquid crystal composition.

Component (c) includes compounds (5) to (11). The compounds have phenylene in which lateral positions are replaced by two pieces of halogen, such as 2,3-difluoro-1,4-phenylene. Preferred examples of component (c) include compounds (5-1) to (5-8), compounds (6-1) to (6-17), compound (7-1), compounds (8-1) to (8-3), compounds (9-1) to (9-11), compounds (10-1) to (10-3) and compounds (11-1) to (11-3). In the compounds, $R^{13}$, $R^{14}$ and $R^{15}$ are independently alkyl having 1 to 10 carbons or alkenyl having 2 to 10 carbons, and in the groups, at least one piece of —$CH_2$— may be replaced by —O— and at least one piece of hydrogen may be replaced by fluorine, and $R^{15}$ may be also hydrogen or fluorine.

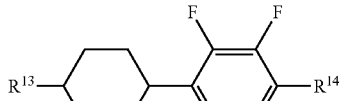
(5-1)

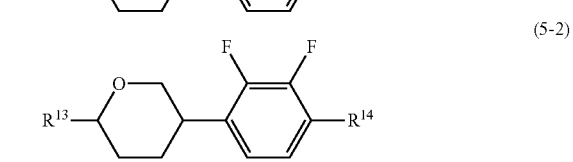
(5-2)

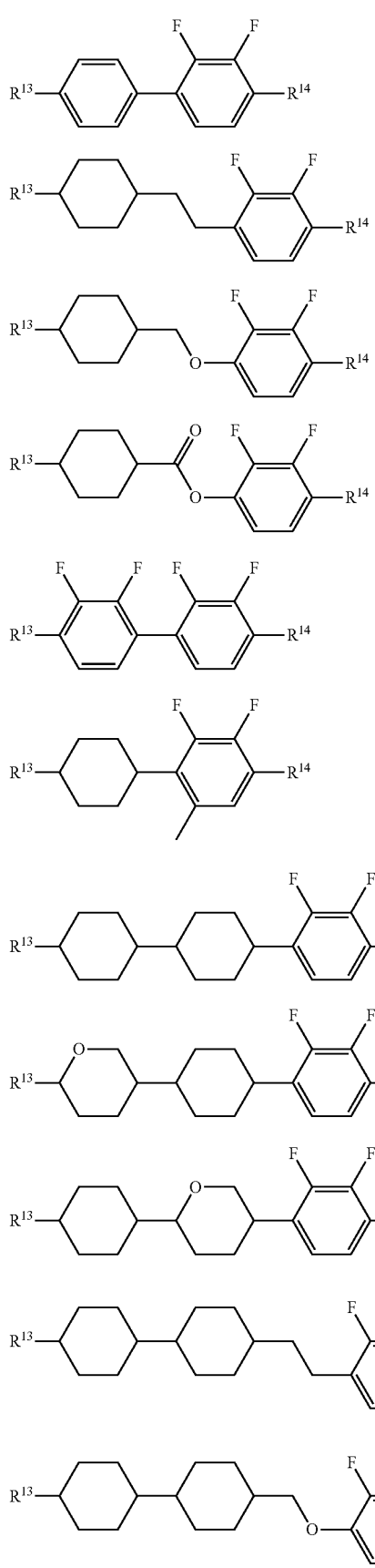
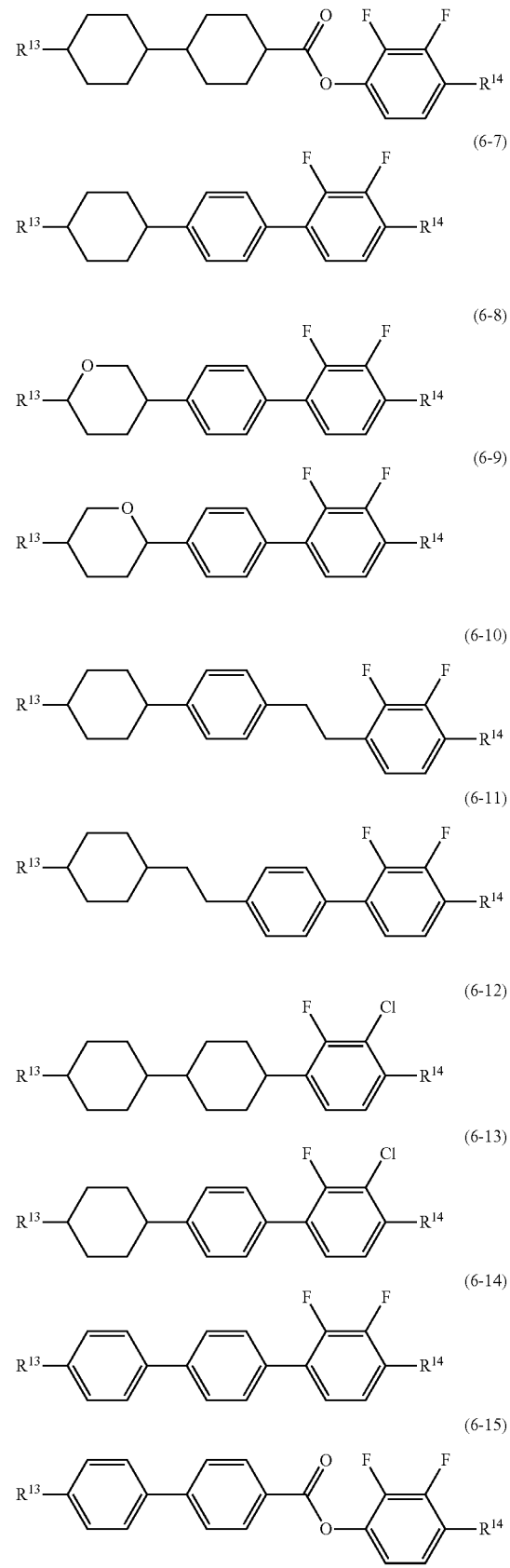

(6-16)
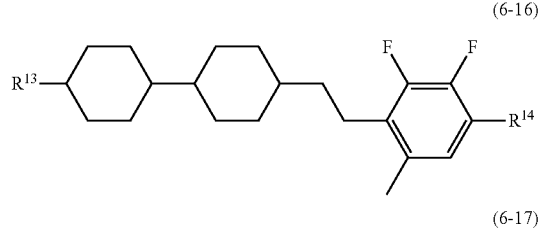
(6-17)
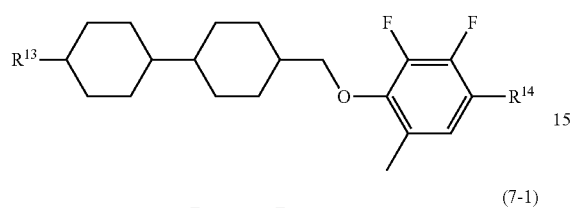
(7-1)
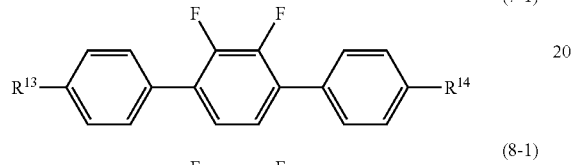
(8-1)
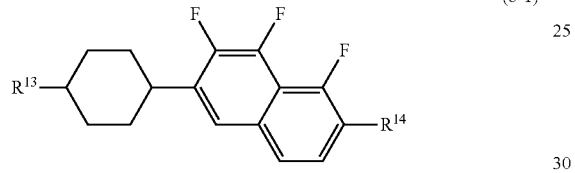
(8-2)
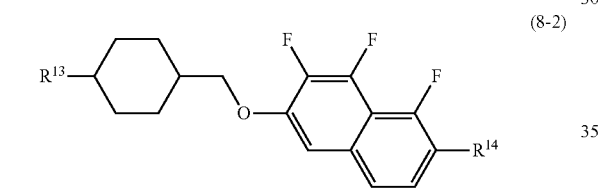
(8-3)
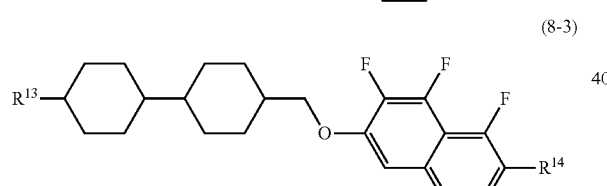
(9-1)
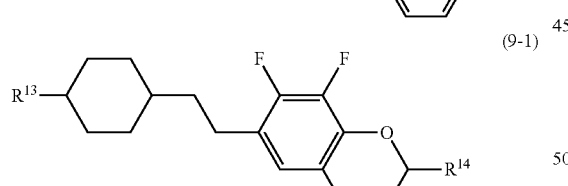
(9-2)
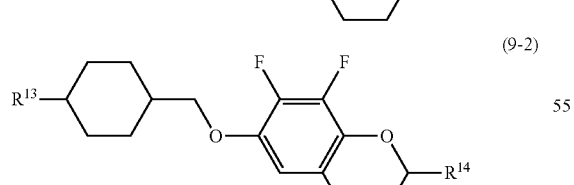
(9-3)
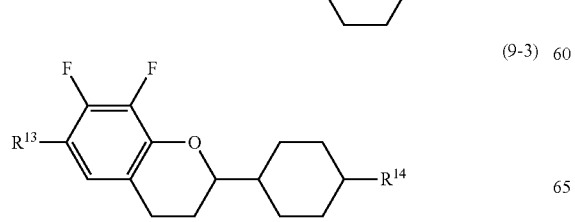
(9-4)
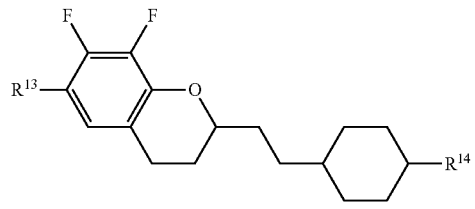
(9-5)
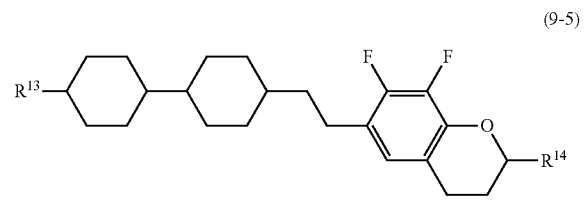
(9-6)
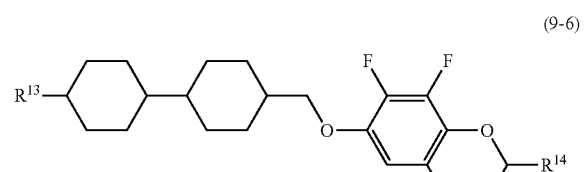
(9-7)
(9-8)
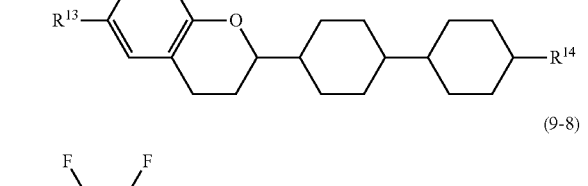
(9-9)
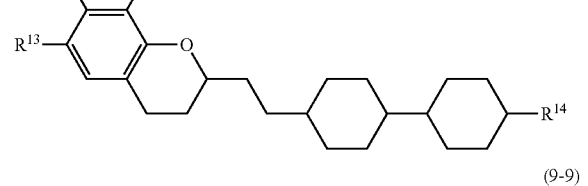
(9-10)
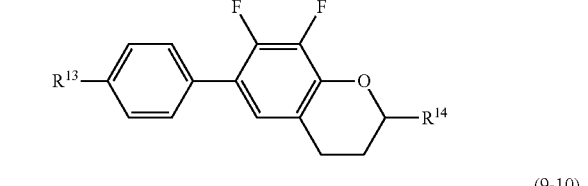
(9-11)
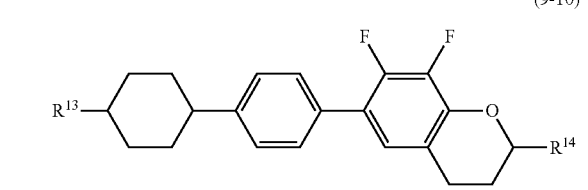

-continued

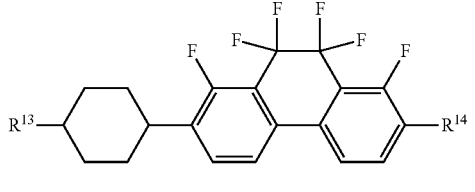
(10-1)

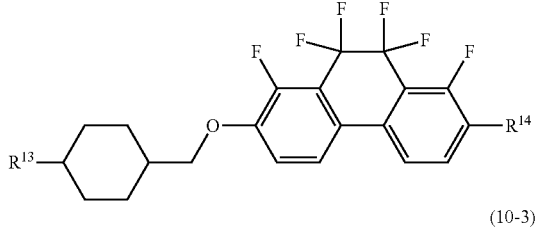
(10-2)

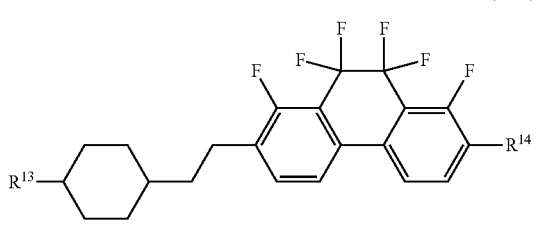
(10-3)

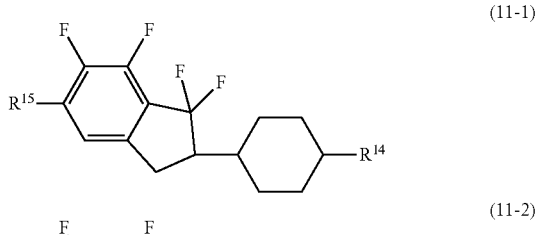
(11-1)

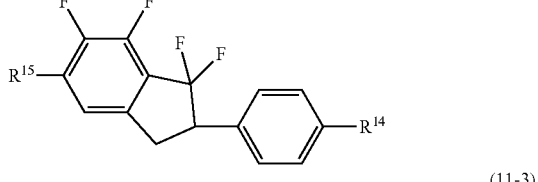
(11-2)

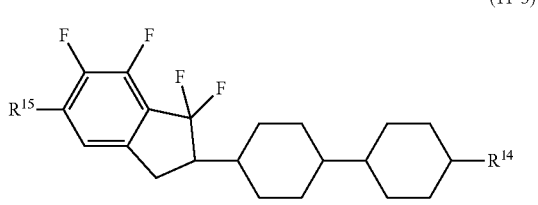
(11-3)

Component (c) has a large negative dielectric anisotropy. Component (c) is used when a composition having a mode such as the IPS mode, the VA mode and the PSA mode is prepared. Accordingly as a content of component (c) is increased, the dielectric anisotropy of the composition negatively increases, but the viscosity increases. Thus, as long as a desired value of threshold voltage of the device is met, the content is preferably as small as possible. Taking into account the dielectric anisotropy of about −5, the content is preferably about 40% by weight or more in order to perform sufficient voltage driving.

In component (c), compound (5) is a bicyclic compound, and therefore effective in decreasing the viscosity, adjusting the optical anisotropy or increasing the dielectric anisotropy. Compounds (6) and (7) are a tricyclic compound, and therefore effective in increasing the maximum temperature and the optical anisotropy or increasing the dielectric anisotropy. Compounds (8) to (11) are effective in increasing the dielectric anisotropy.

When a composition for a mode such as the IPS mode, the VA mode and the PSA mode is prepared, a content of component (c) is preferably about 40% by weight or more, and further preferably in the range of about 50% by weight to about 95% by weight, based on the weight of the composition. When component (c) is added to a composition having a positive dielectric anisotropy, a preferred content of component (c) is about 30% by weight or less. An elastic constant of the composition and a voltage-transmittance curve of the device can be adjusted by adding component (c) thereto.

Component (d) includes a compound having a halogen-containing or a fluorine-containing group at a right terminal. Specific preferred examples of component (d) include compounds (12-1) to (12-16), compounds (13-1) to (13-113) or compounds (14-1) to (14-57). In the compounds, $R^{16}$ is alkyl having 1 to 10 carbons or alkenyl having 2 to 10 carbons, and in the groups, at least one piece of hydrogen may be replaced by —O—, and in the monovalent groups, at least one piece of hydrogen may be replaced by fluorine; and $X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$.

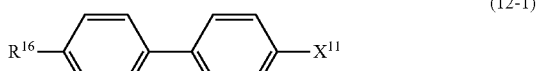
(12-1)

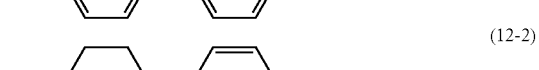
(12-2)

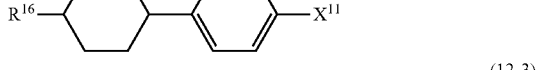
(12-3)

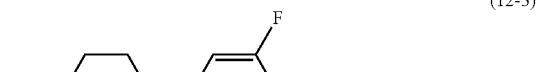
(12-4)

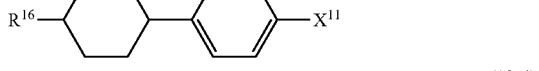
(12-5)

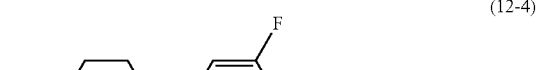
(12-6)

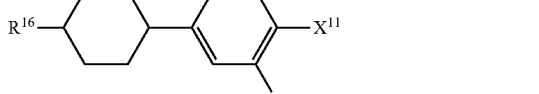
(12-7)

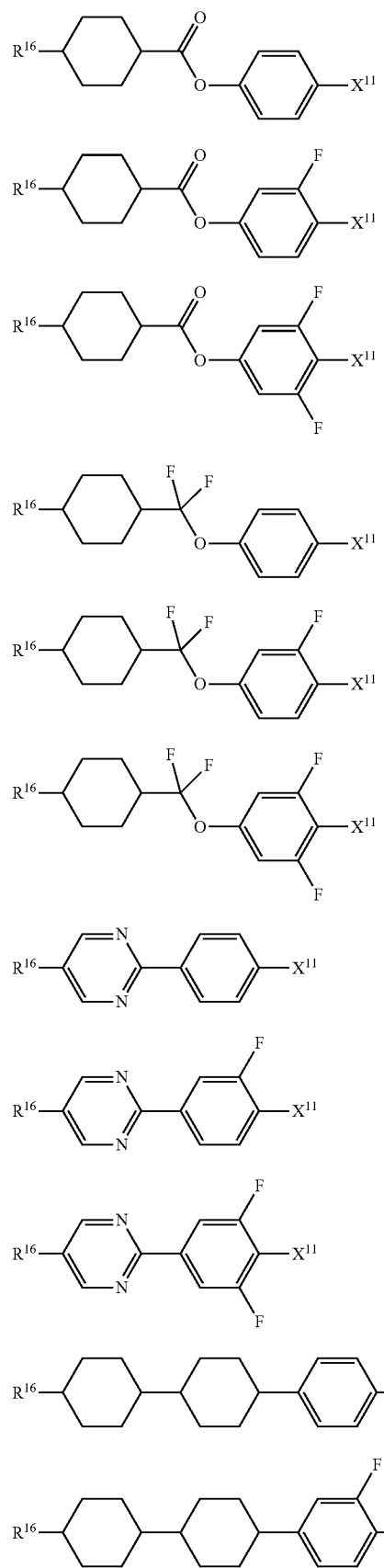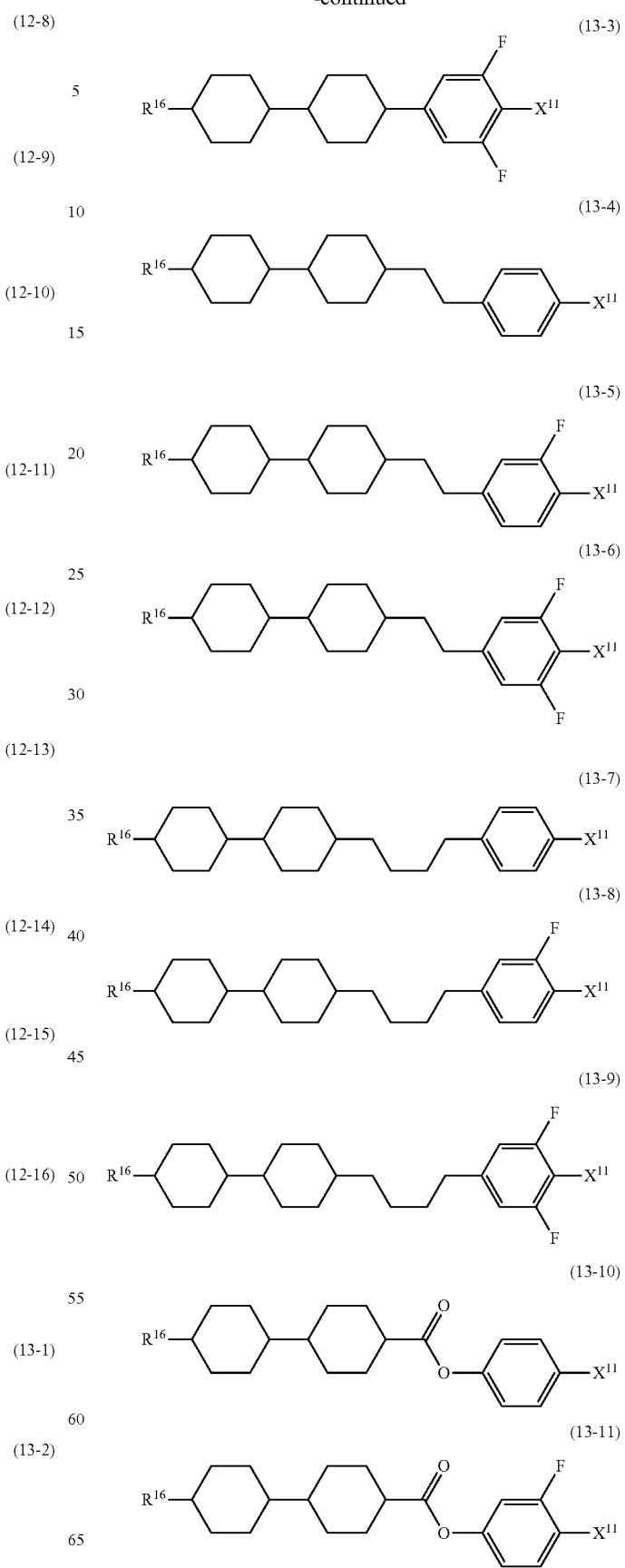

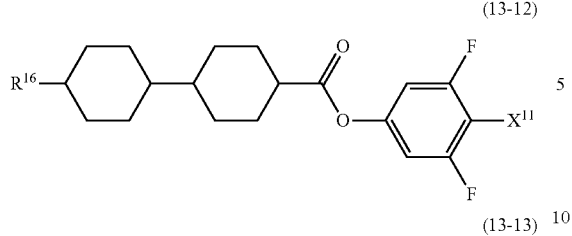
(13-12)
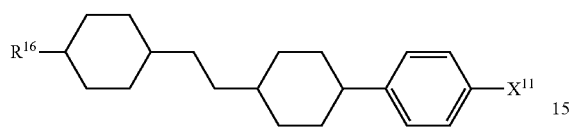
(13-13)
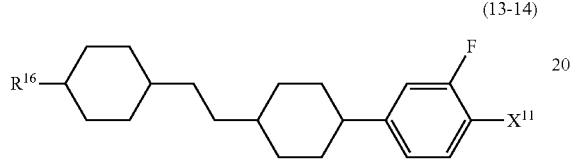
(13-14)
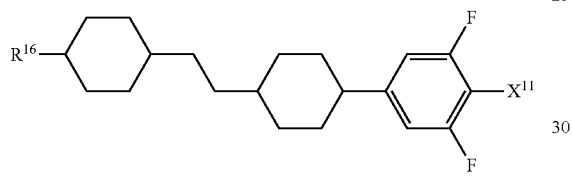
(13-15)
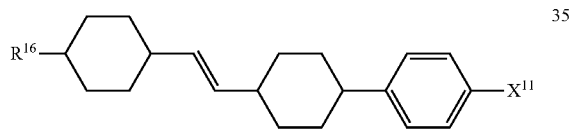
(13-16)
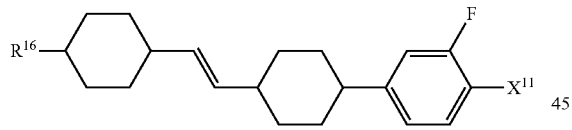
(13-17)
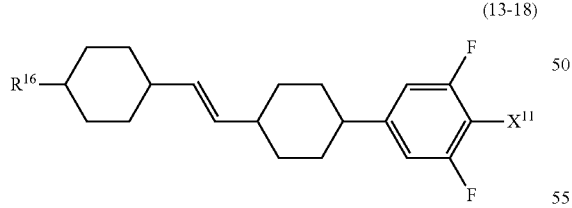
(13-18)
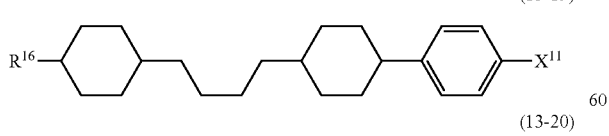
(13-19)
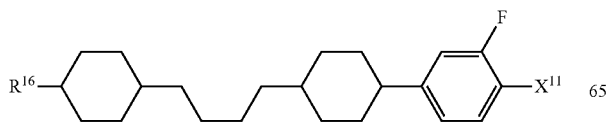
(13-20)
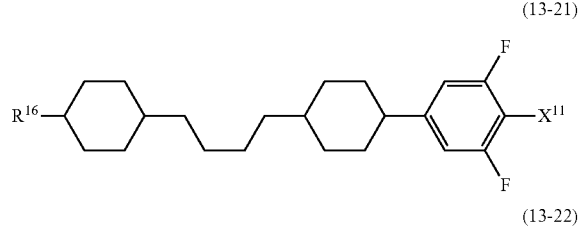
(13-21)
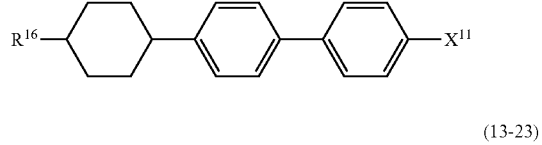
(13-22)
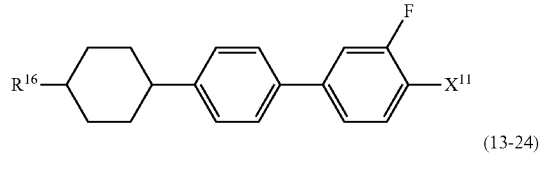
(13-23)
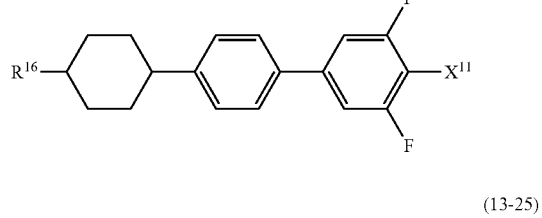
(13-24)
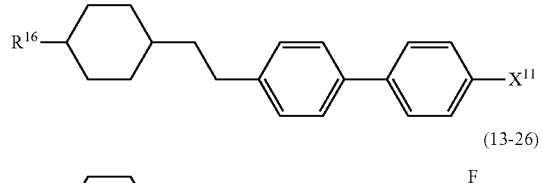
(13-25)
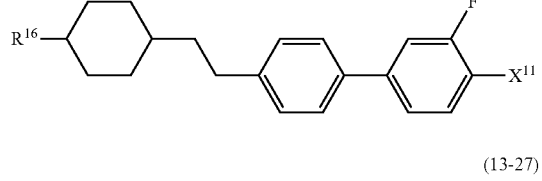
(13-26)
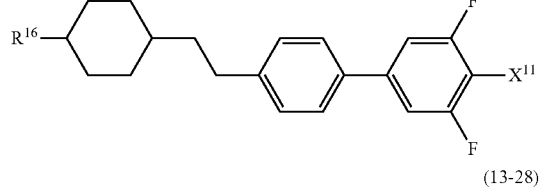
(13-27)
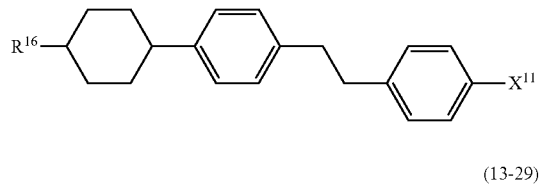
(13-28)
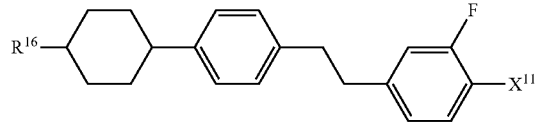
(13-29)

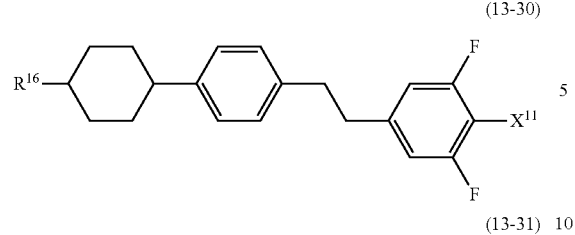
(13-30)
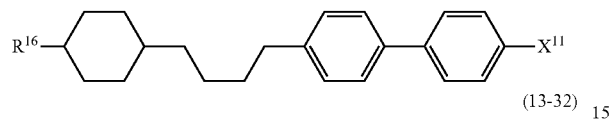
(13-31)
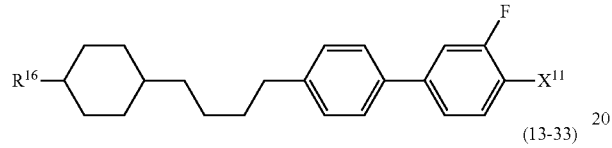
(13-32)
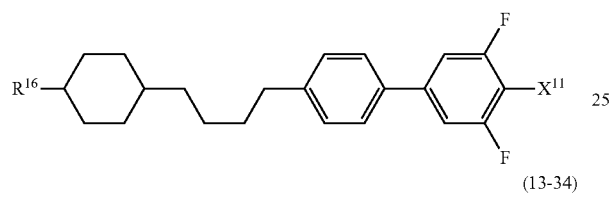
(13-33)
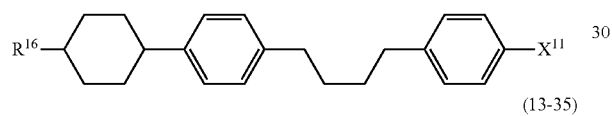
(13-34)
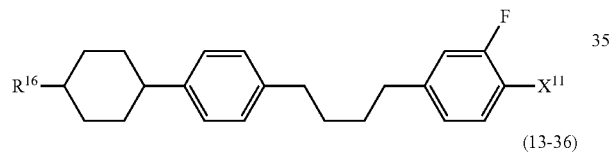
(13-35)
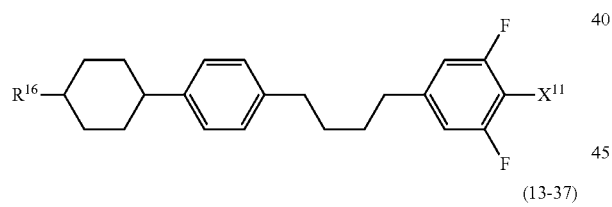
(13-36)
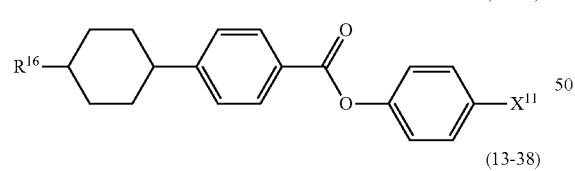
(13-37)
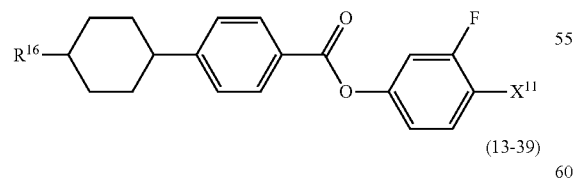
(13-38)
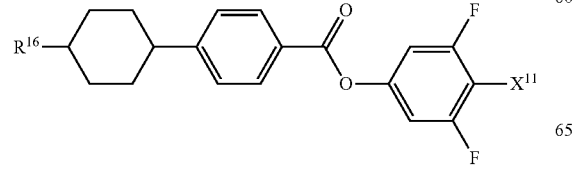
(13-39)
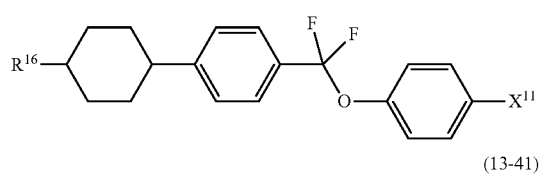
(13-40)
(13-41)
(13-42)
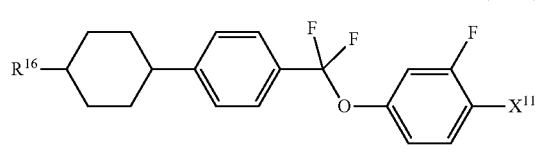
(13-43)
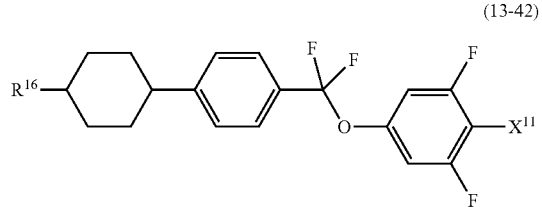
(13-44)
(13-45)
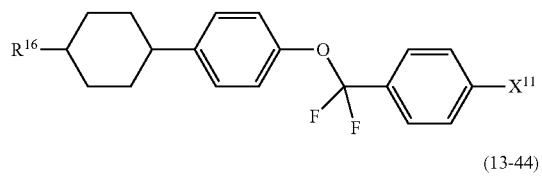
(13-46)
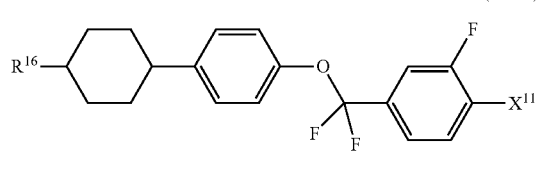
(13-47)
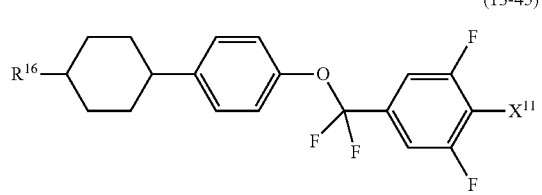
(13-48)
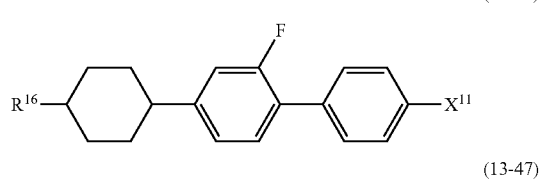
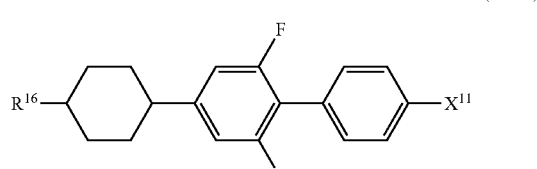

(13-49)
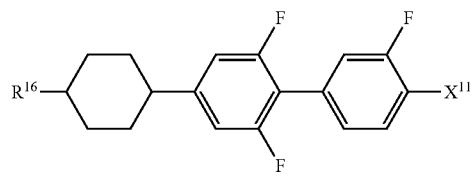
(13-50)
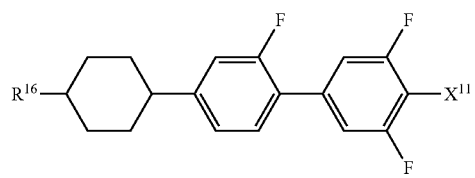
(13-51)
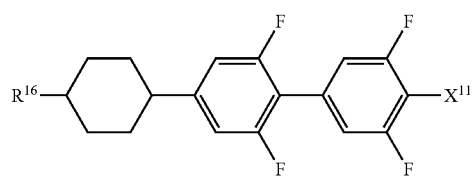
(13-52)
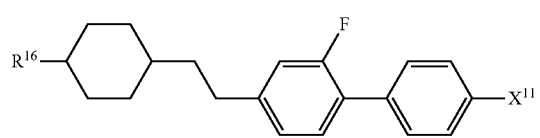
(13-53)
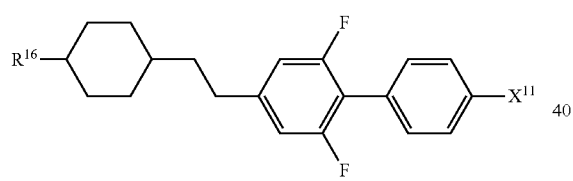
(13-54)
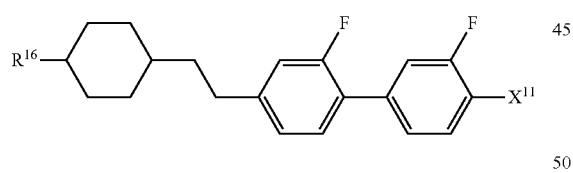
(13-55)
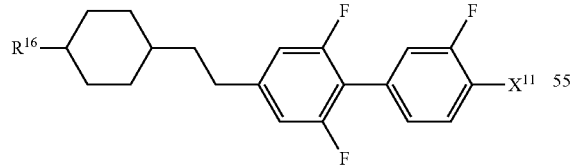
(13-56)
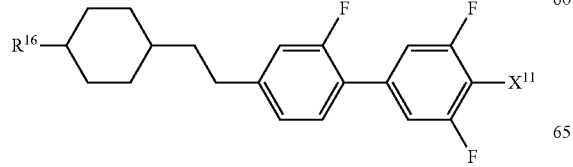
(13-57)
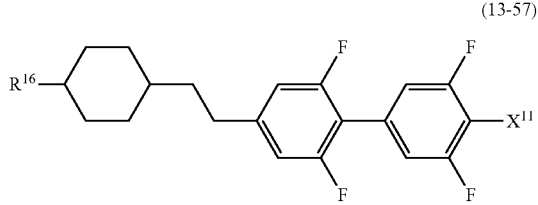
(13-58)
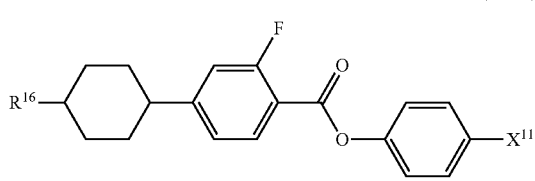
(13-59)
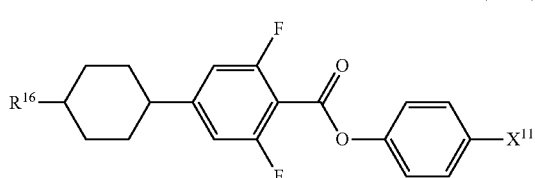
(13-60)
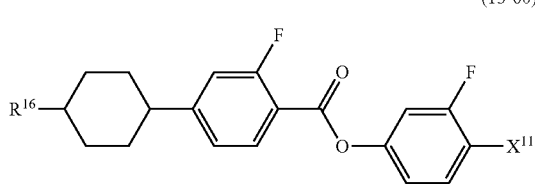
(13-61)
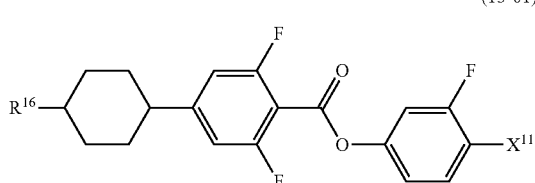
(13-62)
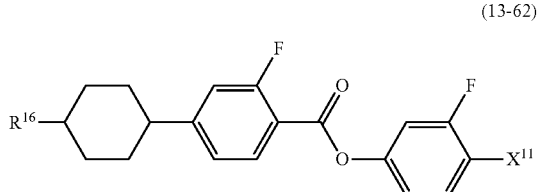
(13-63)
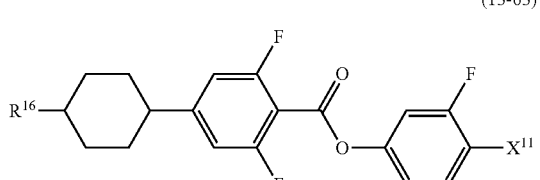
(13-64)
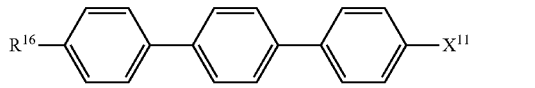

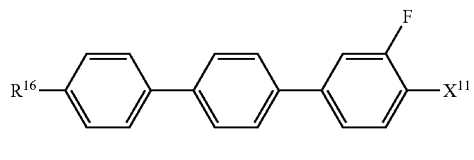 (13-65)
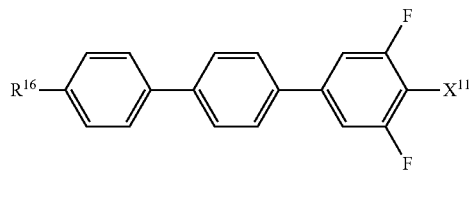 (13-66)
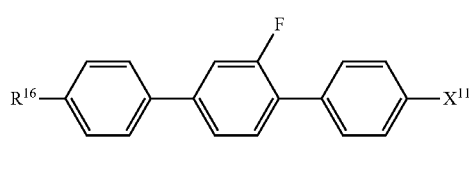 (13-67)
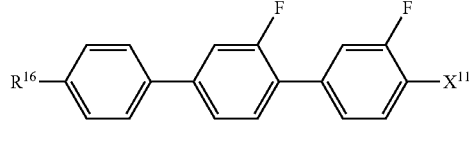 (13-68)
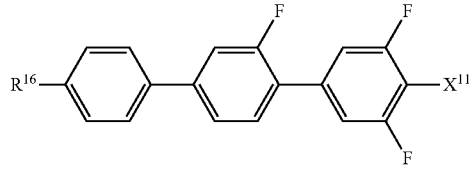 (13-69)
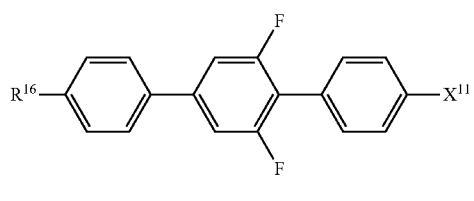 (13-70)
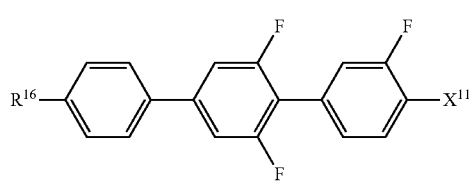 (13-71)
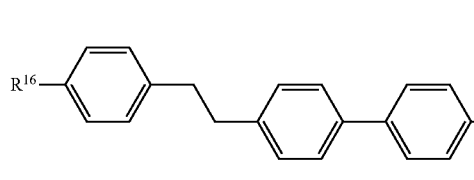 (13-72)
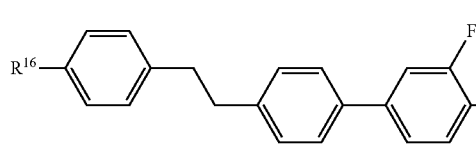 (13-73)
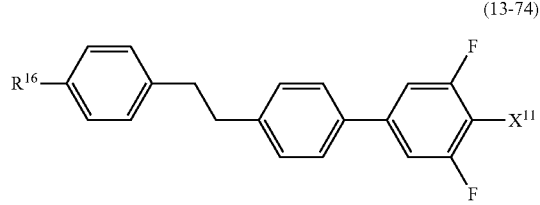 (13-74)
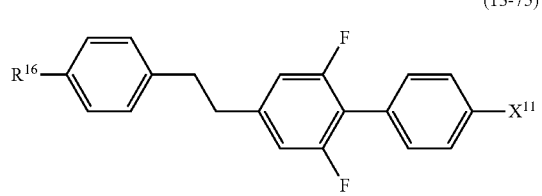 (13-75)
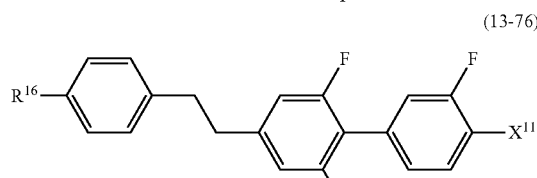 (13-76)
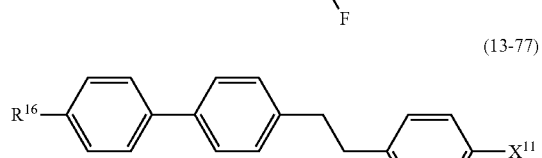 (13-77)
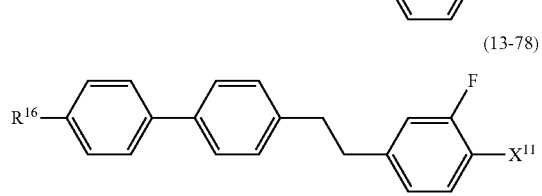 (13-78)
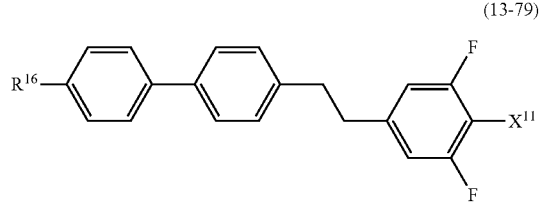 (13-79)
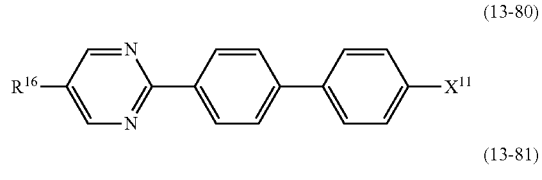 (13-80)
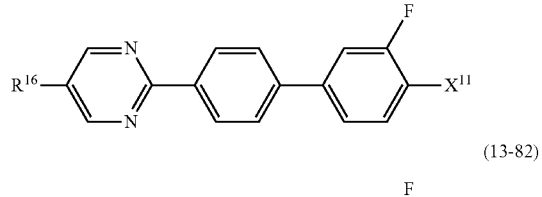 (13-81)
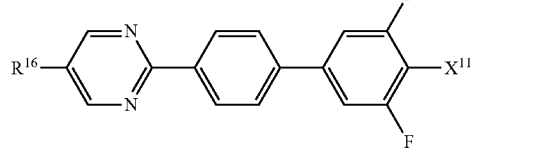 (13-82)

(13-83)
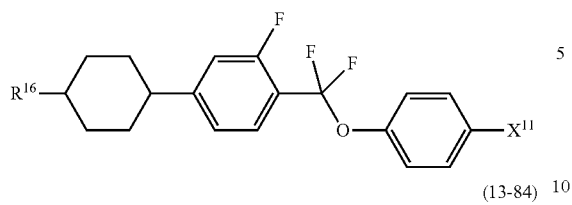
(13-84)
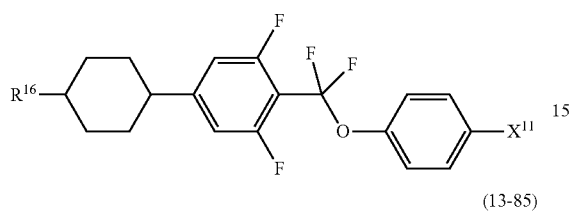
(13-85)
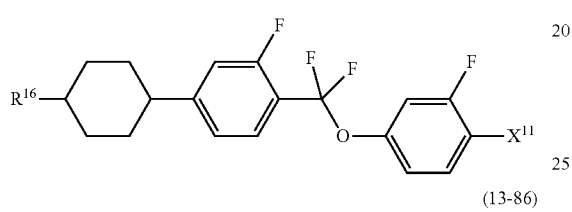
(13-86)
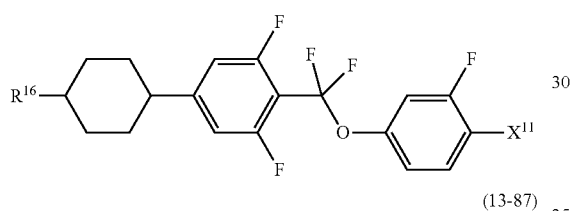
(13-87)
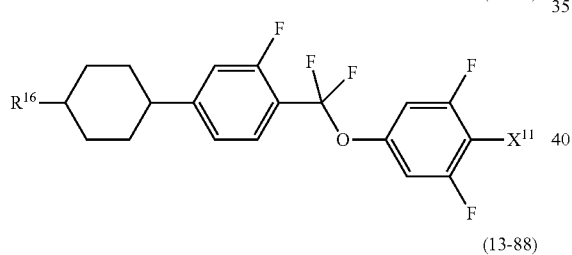
(13-88)
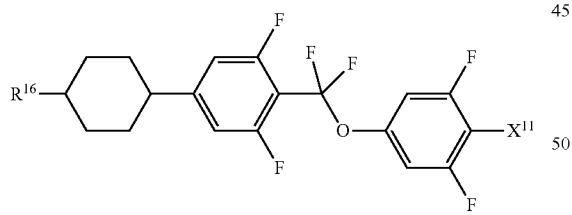
(13-89)
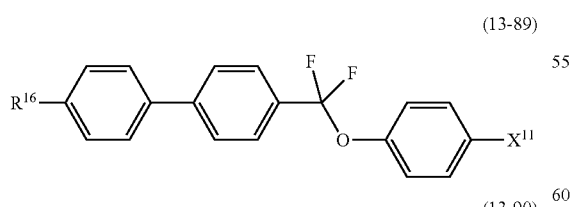
(13-90)
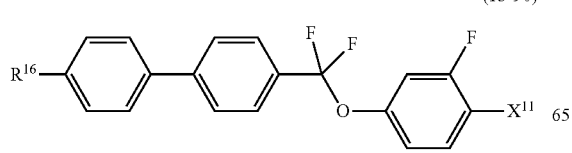
(13-91)
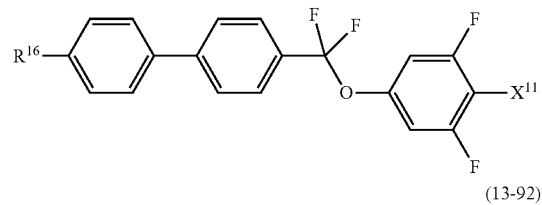
(13-92)
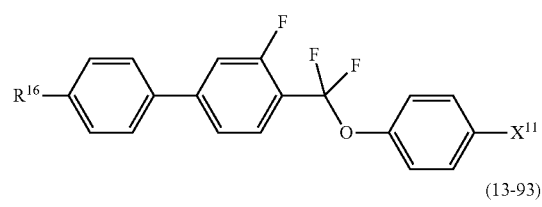
(13-93)
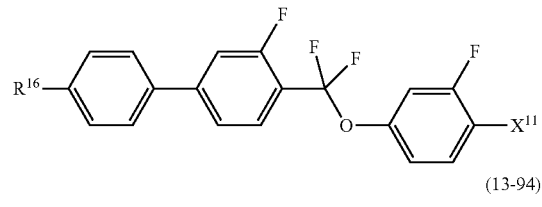
(13-94)
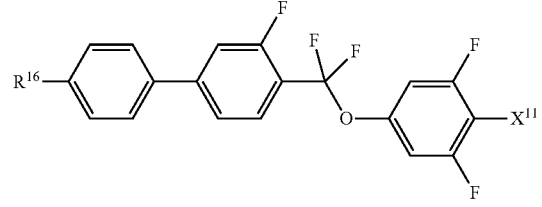
(13-95)
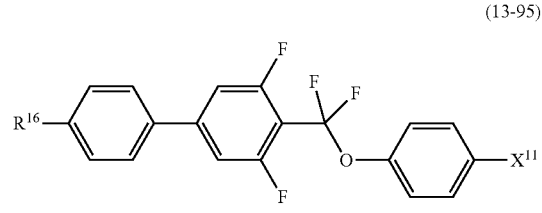
(13-96)
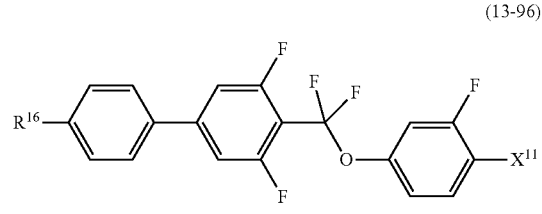
(13-97)
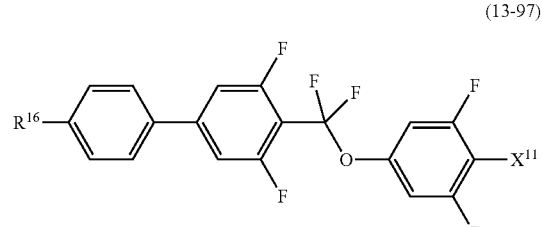
(13-98)
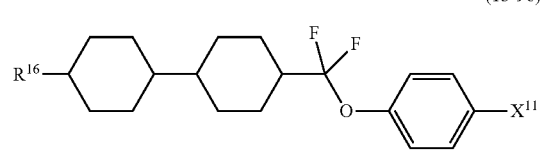

(13-99)
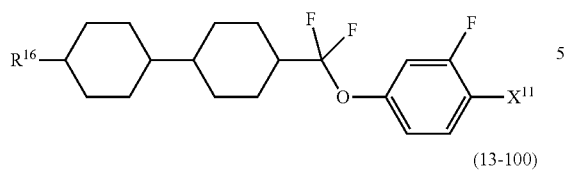
(13-100)
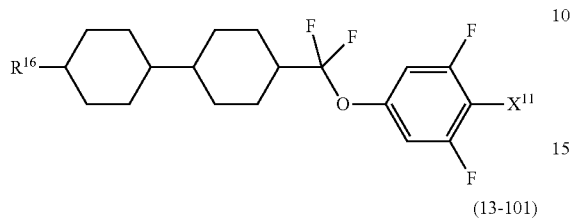
(13-101)
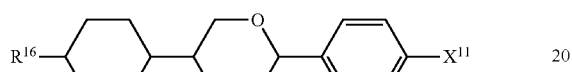
(13-102)
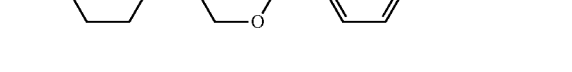
(13-103)
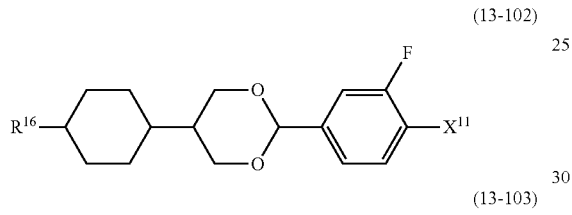
(13-104)
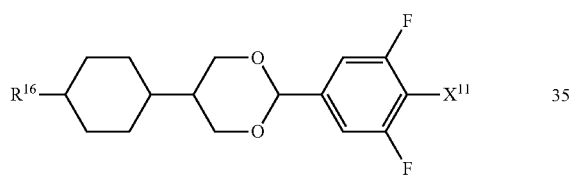
(13-105)
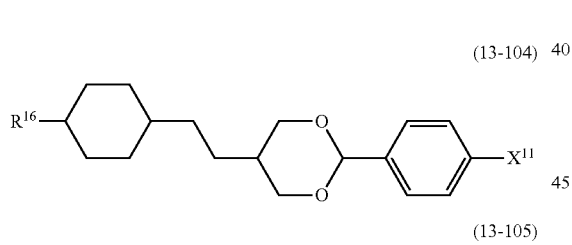
(13-106)
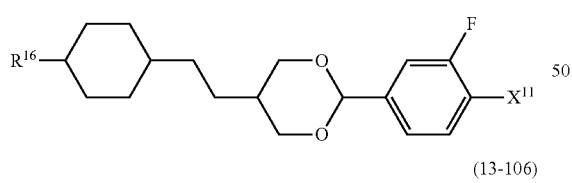
(13-107)
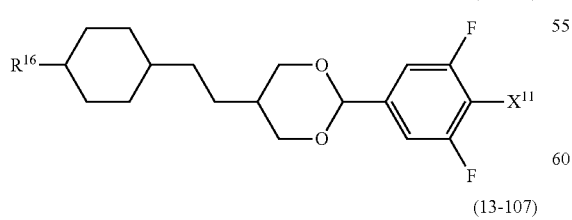
(13-108)
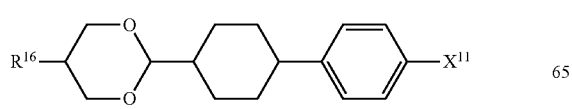
(13-109)
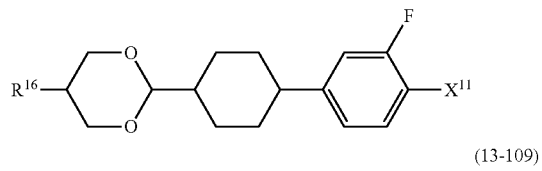
(13-110)
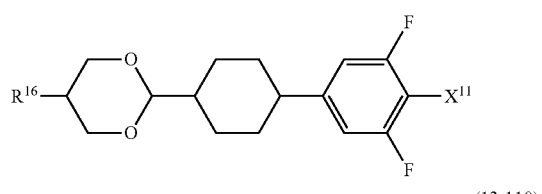
(13-111)
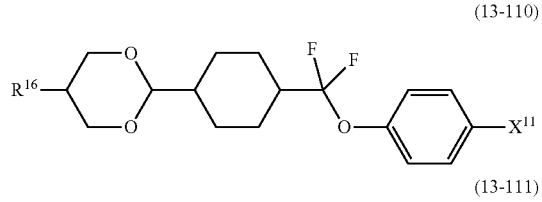
(13-112)
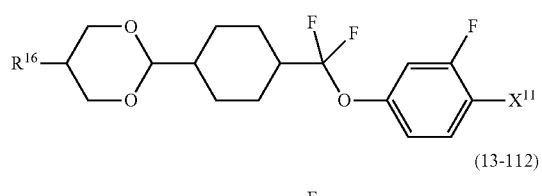
(13-113)
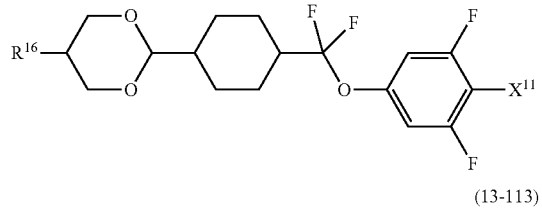
(14-1)
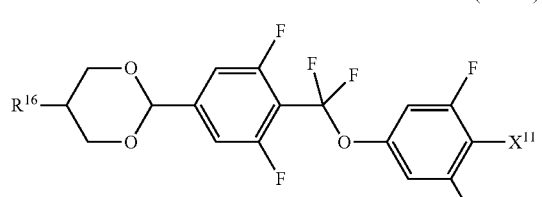
(14-2)
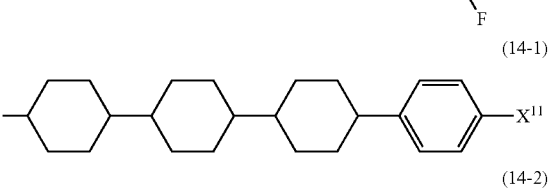
(14-3)
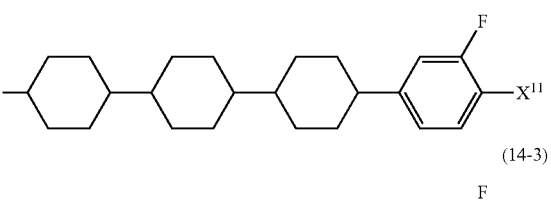
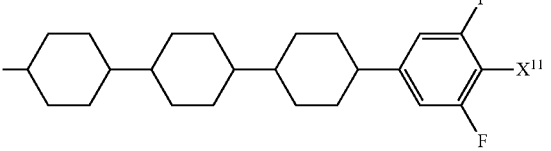

(14-4)
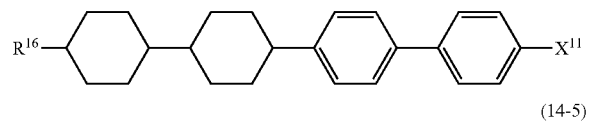
(14-5)
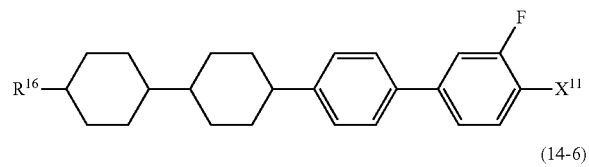
(14-6)
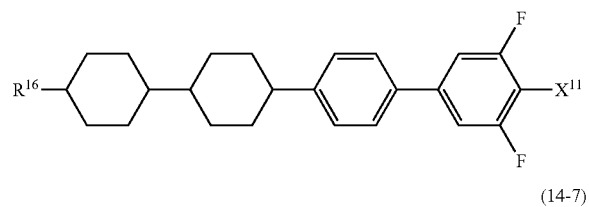
(14-7)
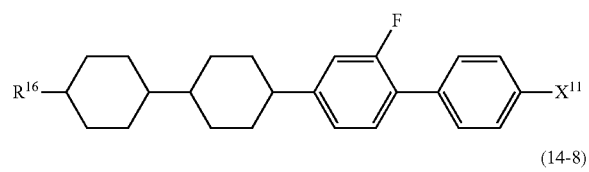
(14-8)
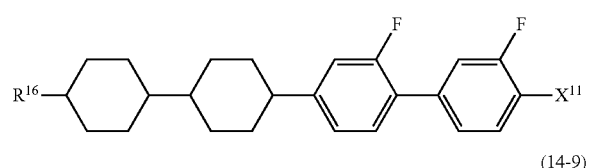
(14-9)
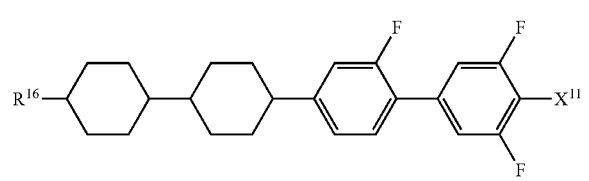
(14-10)
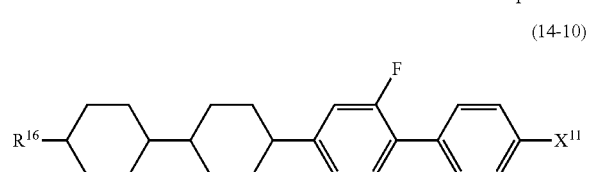
(14-11)
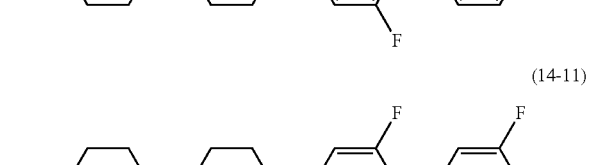
(14-12)
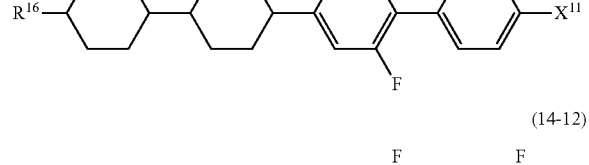
(14-13)
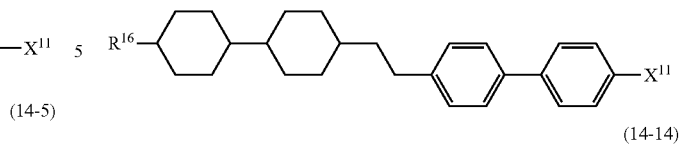
(14-14)
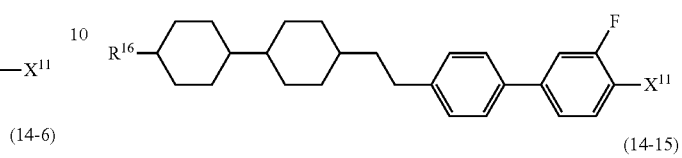
(14-15)
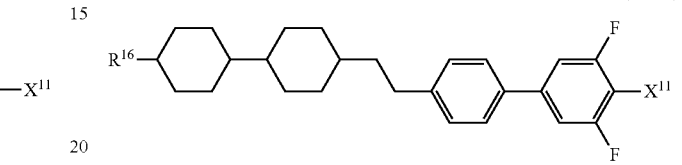
(14-16)
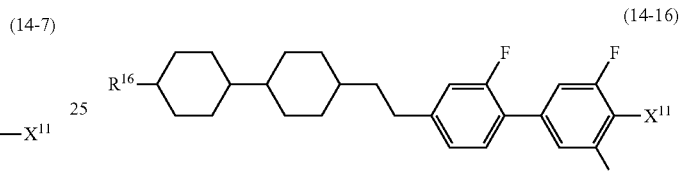
(14-17)
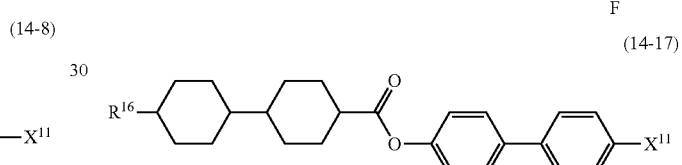
(14-18)
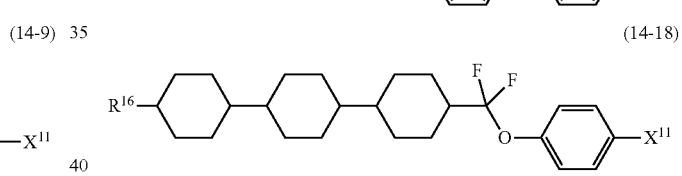
(14-19)
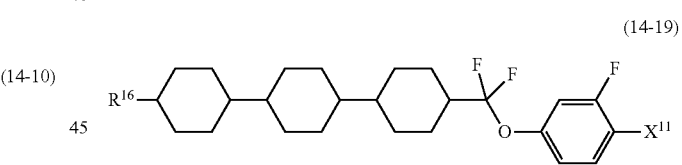
(14-20)
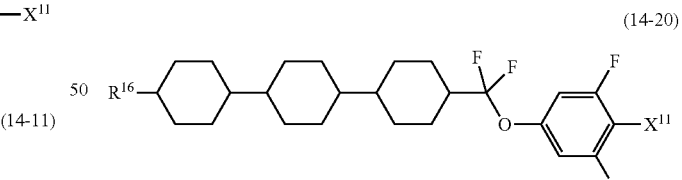
(14-21)
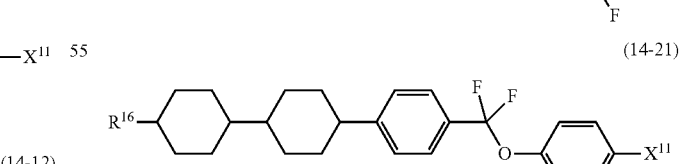
(14-22)
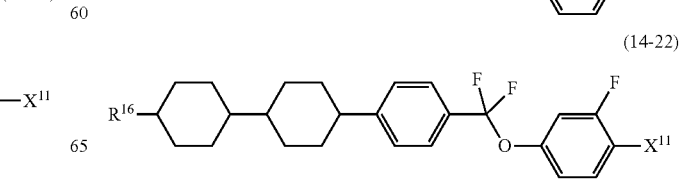

(14-23)
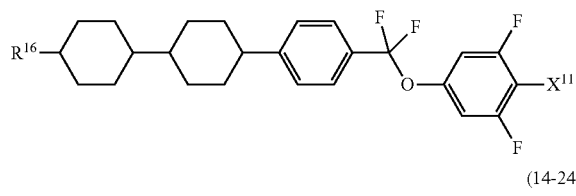
(14-24)
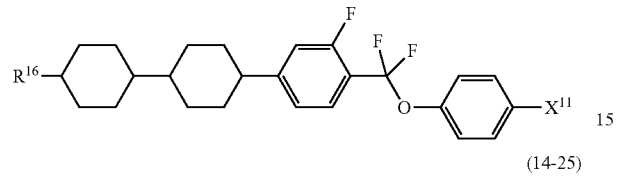
(14-25)
(14-26)
(14-27)
(14-28)
(14-29)
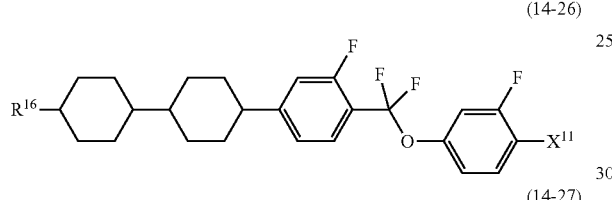
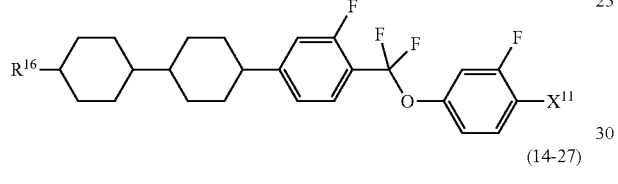
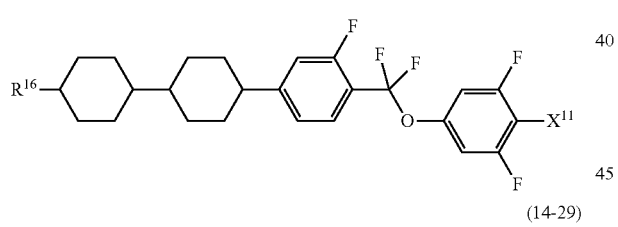
(14-30)
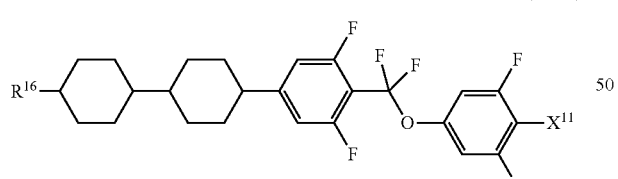
(14-31)
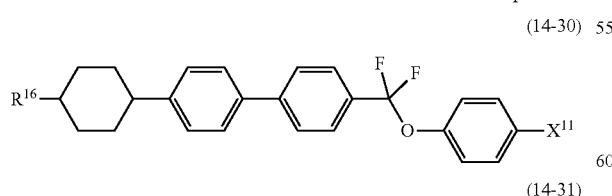
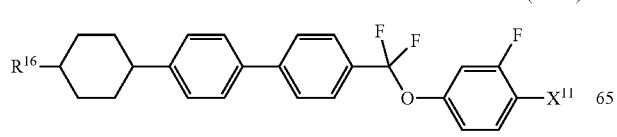
(14-32)
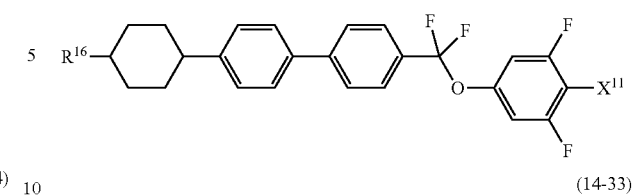
(14-33)
(14-34)
(14-35)
(14-36)
(14-37)
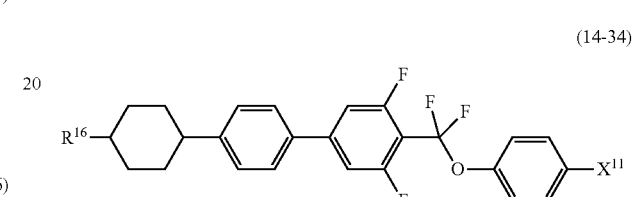
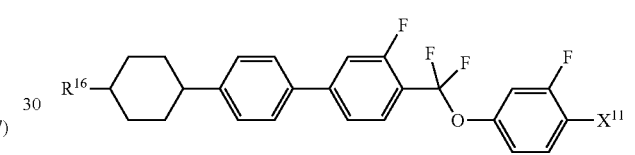
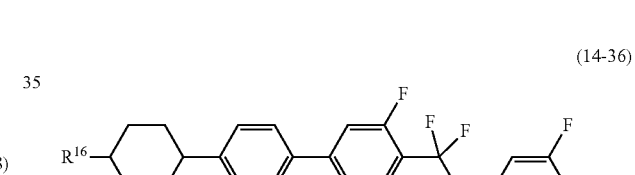
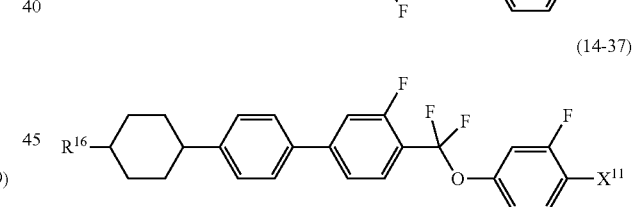
(14-38)
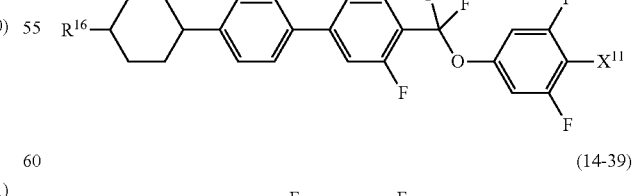
(14-39)
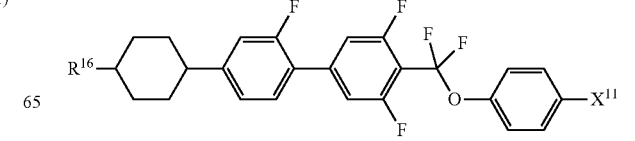

(14-40)
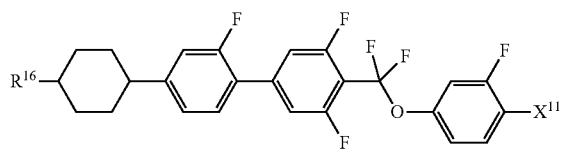
(14-41)
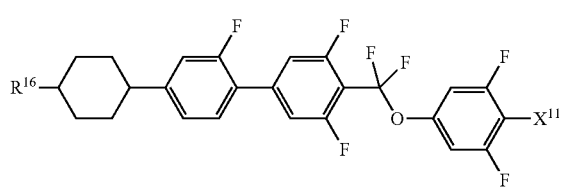
(14-42)
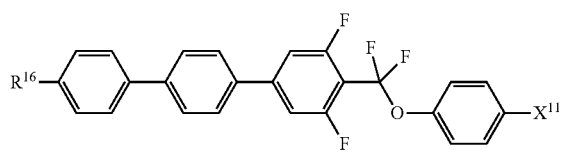
(14-43)
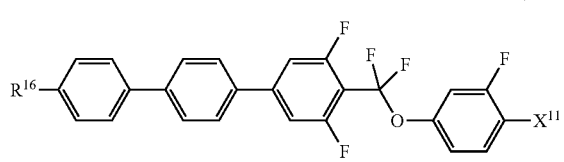
(14-44)
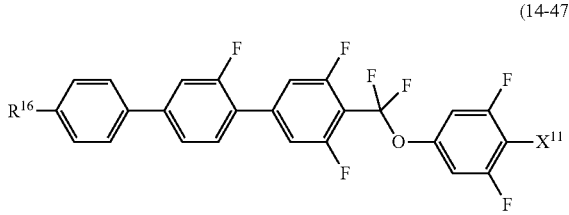
(14-45)
(14-46)
(14-47)
(14-48)
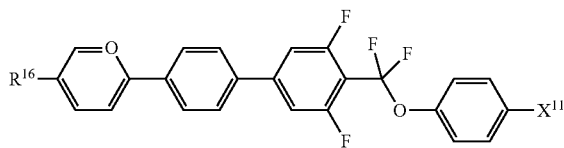
(14-49)
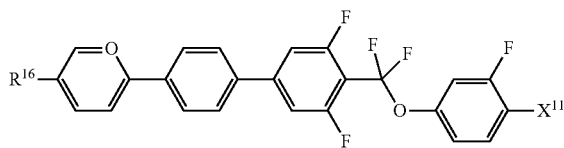
(14-50)
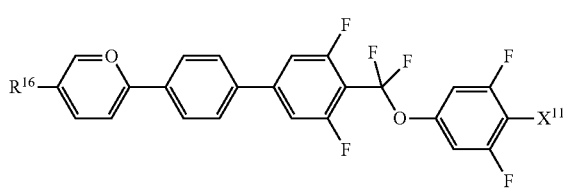
(14-51)
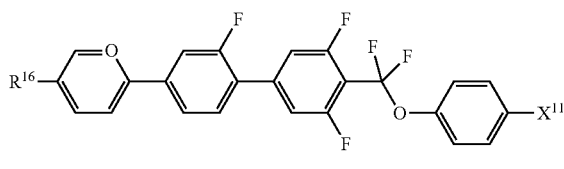
(14-52)
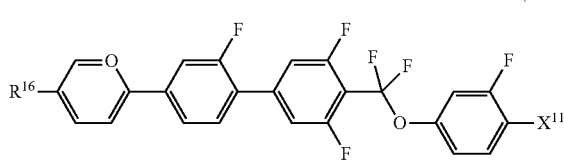
(14-53)
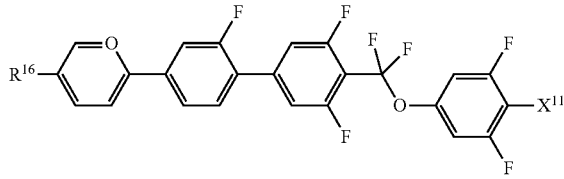
(14-54)
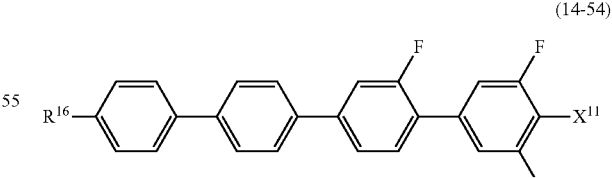
(14-55)
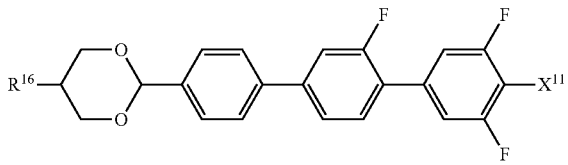

-continued (14-56)
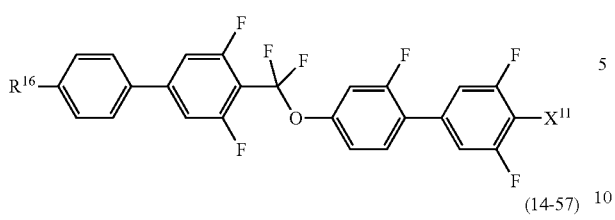

(14-57)
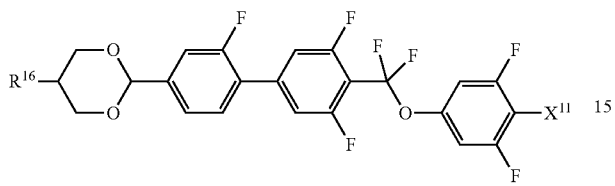

Component (d) has a positive dielectric anisotropy and an excellent stability to heat and light, and therefore is used for preparing a composition for a mode such as the IPS mode, the FFS mode and the OCB mode. A content of Component (d) is suitably in the range of about 1% by weight to about 99% by weight, preferably in the range of about 10% by weight to about 97% by weight, and further preferably in the range of about 40% by weight to about 95% by weight, based on the weight of the composition. When component (d) is added to a composition having a negative dielectric anisotropy, a preferred content of component (d) is about 30% by weight or less based on the weight of the composition. The elastic constant of the composition and the voltage-transmittance curve of the device can be adjusted by adding compound (d) thereto.

Component (e) includes compound (15) in which a right terminal group is —C≡N or —C≡C—C≡N. Preferred examples of component (e) include compounds (15-1) to (15-64). In the compounds, $R^{17}$ is alkyl having 1 to 10 carbons or alkenyl having 2 to 10 carbons, and in the groups, at least one piece of —CH$_2$— may be replaced by —O—, and in the monovalent groups, at least one piece of hydrogen may be replaced by fluorine; and $X^{12}$ is —C≡N or —C≡C—C≡N.

(15-1)
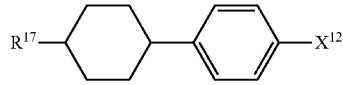

(15-2)
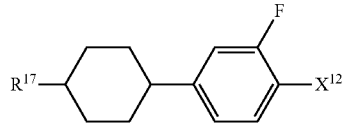

(15-3)
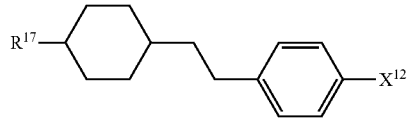

(15-4)
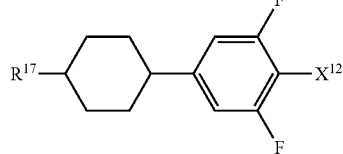

-continued (15-5)
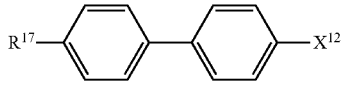

(15-6)
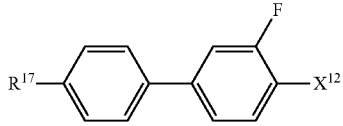

(15-7)
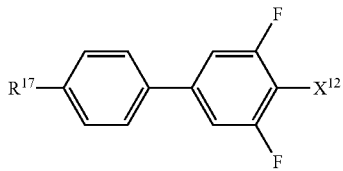

(15-8)
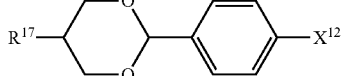

(15-9)
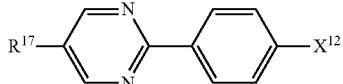

(15-10)
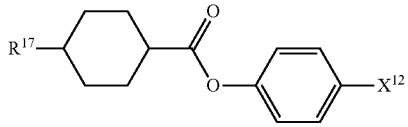

(15-11)
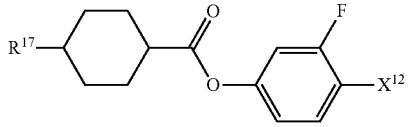

(15-12)
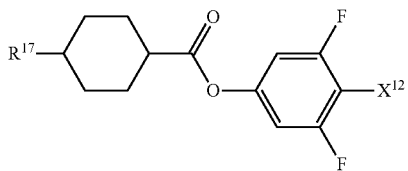

(15-13)
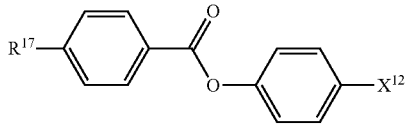

(15-14)
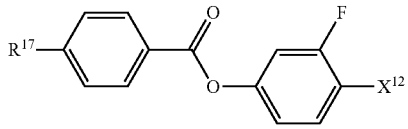

(15-15)
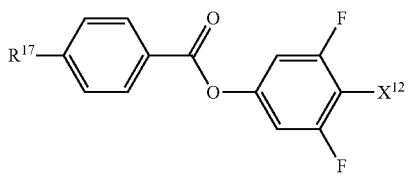

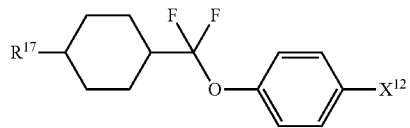 (15-16)
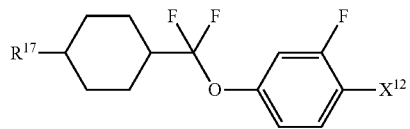 (15-17)
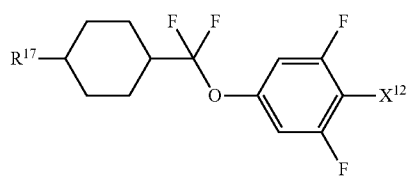 (15-18)
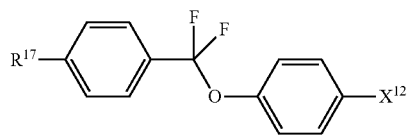 (15-19)
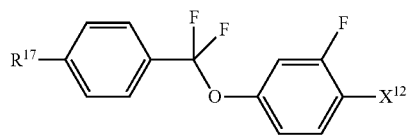 (15-20)
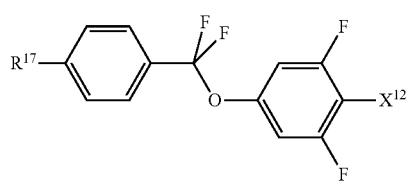 (15-21)
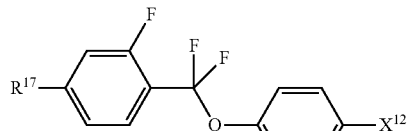 (15-22)
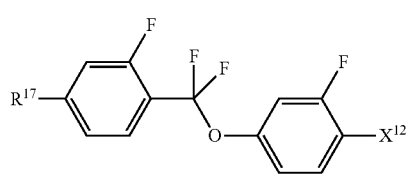 (15-23)
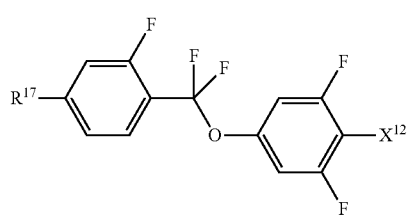 (15-24)
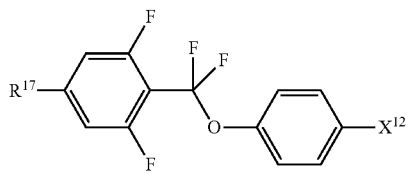 (15-25)
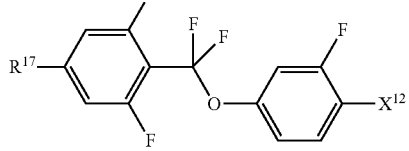 (15-26)
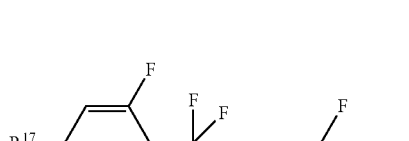 (15-27)
 (15-28)
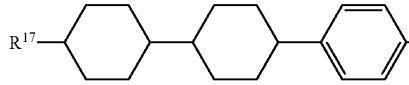 (15-29)
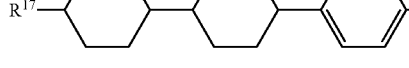 (15-30)
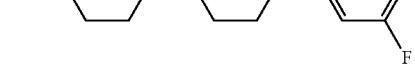 (15-31)
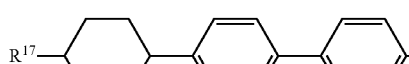 (15-32)
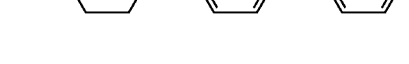 (15-33)

-continued
(15-34)
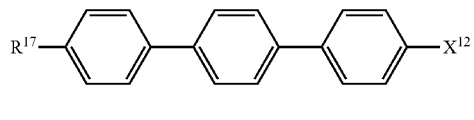
(15-35)
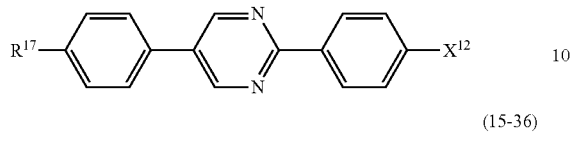
(15-36)
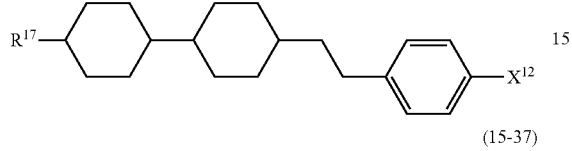
(15-37)
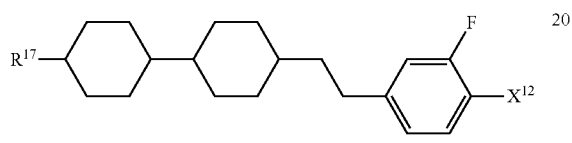
(15-38)
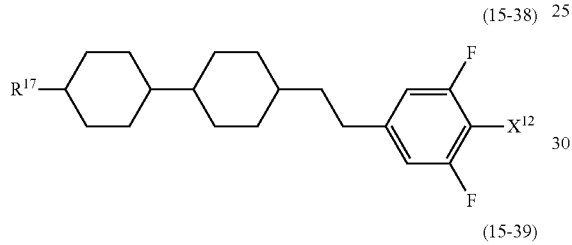
(15-39)
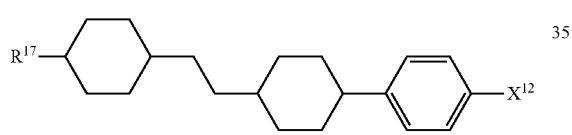
(15-40)
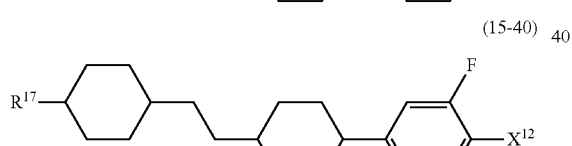
(15-41)
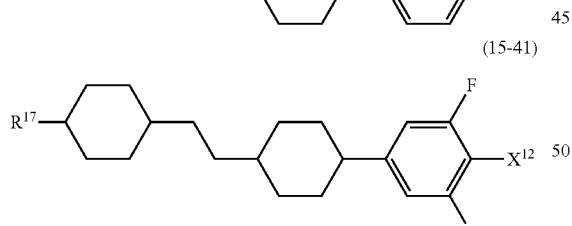
(15-42)
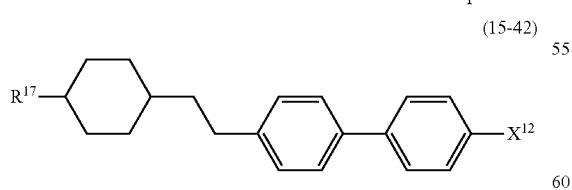
(15-43)
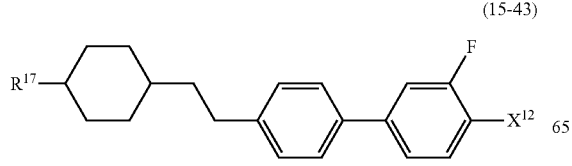
-continued
(15-44)
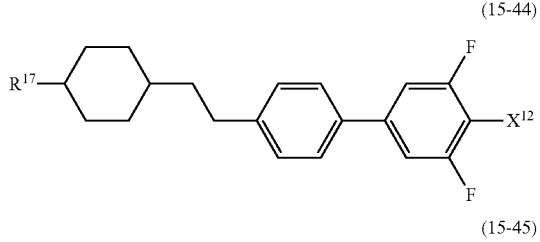
(15-45)
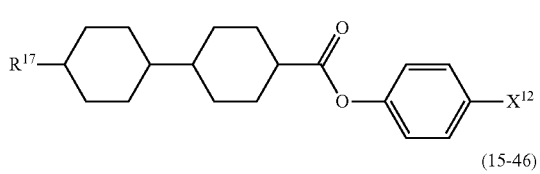
(15-46)
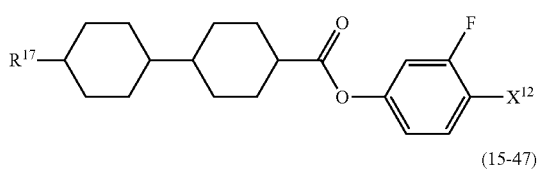
(15-47)
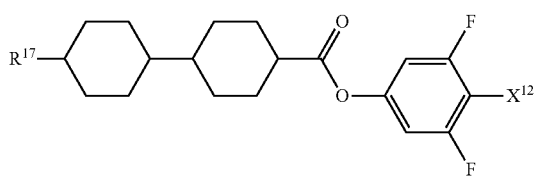
(15-48)
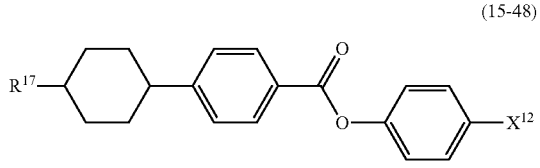
(15-49)
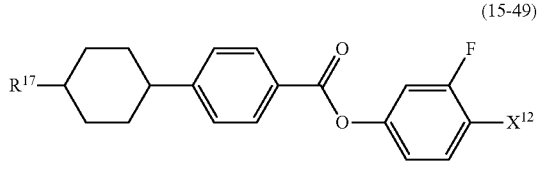
(15-50)
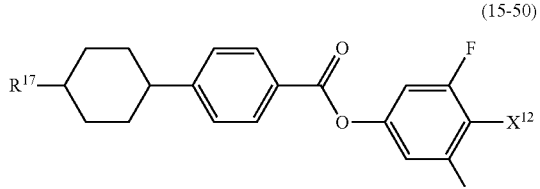
(15-51)
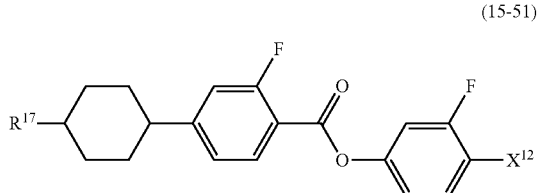
(15-52)
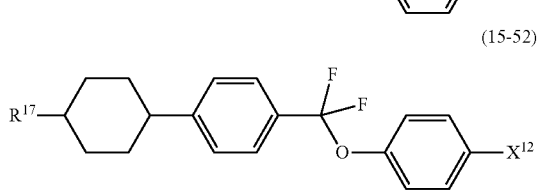

(15-53)
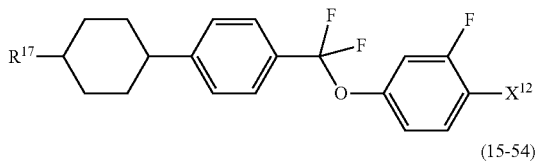

(15-54)
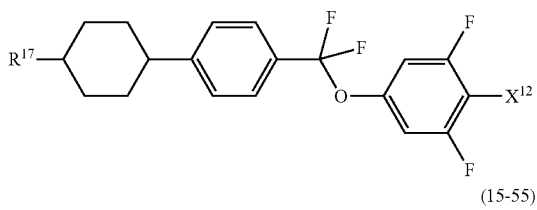

(15-55)
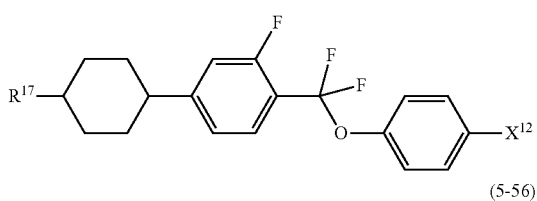

(5-56)
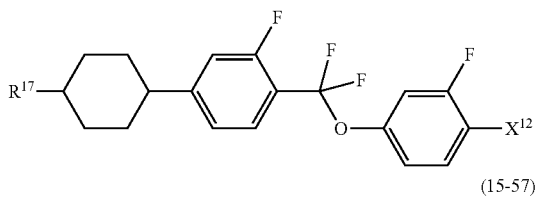

(15-57)
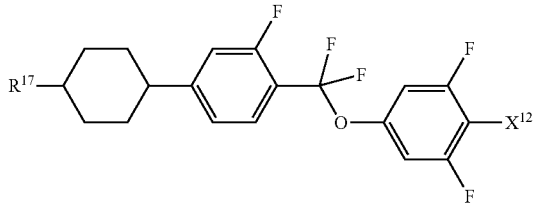

(15-58)
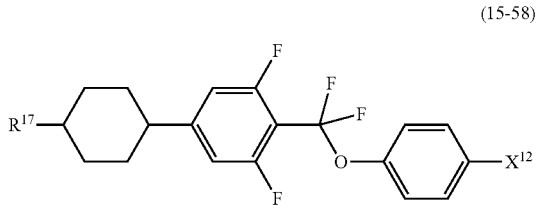

(15-59)
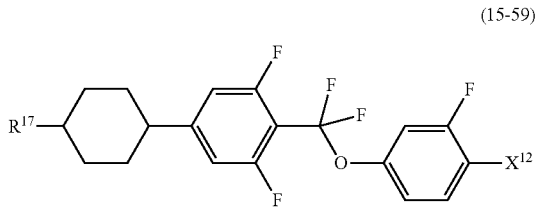

(15-60)
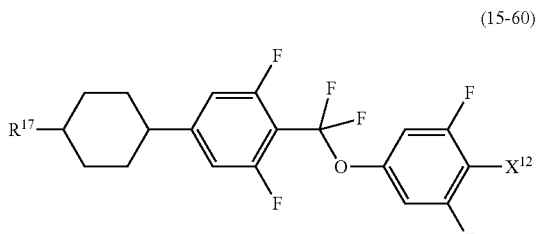

(15-61)
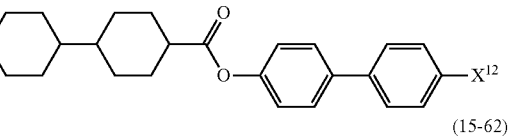

(15-62)
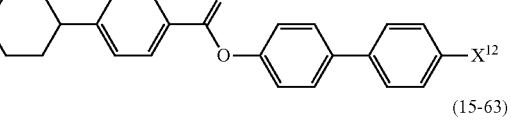

(15-63)
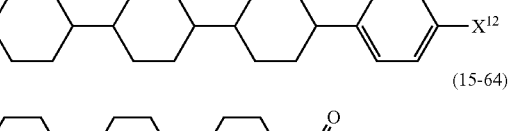

(15-64)
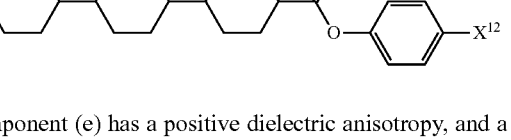

Component (e) has a positive dielectric anisotropy, and a value thereof is large, and therefore is used for preparing a composition for a mode such as the TN mode. The dielectric anisotropy of the composition can be increased by adding component (e) thereto. Component (e) is effective in extending the temperature range of the liquid crystal phase, adjusting the viscosity or adjusting the optical anisotropy. Component (e) is useful also in adjusting the voltage-transmittance curve of the device.

When a composition for a mode such as the TN mode is prepared, a content of component (e) is suitably in the range of about 1% by weight to about 99% by weight, preferably, in the range of about 10% by weight to about 97% by weight, and further preferably in the range of about 40% by weight to about 95% by weight, based on the weight of the composition. When component (e) is added to a composition having a negative dielectric anisotropy, the content of component (e) is preferably about 30% by weight or less. The elastic constant of the composition and the voltage-transmittance curve of the device can be adjusted by adding component (e) thereto.

The liquid crystal composition satisfying at least one of physical properties such as the high stability to heat and light, the high maximum temperature, the low minimum temperature, the small viscosity, the suitable optical anisotropy, the large dielectric anisotropy, the large specific resistance, the large specific resistance and the suitable elastic constant can be prepared by suitably combining compound (1) with the components (b) to (e). A liquid crystal compound different from compounds (1) to (15) may be added, when necessary.

3-2. Additive

A liquid crystal composition is prepared according to a known method. For example, the component compounds are mixed and dissolved in each other by heating. According to an application, an additive may be added to the composition. Specific examples of the additive include a polymerizable compound, a polymerization initiator, a polymerization inhibitor, an optically active compound, an antioxidant, a ultraviolet light absorber, a light stabilizer, a heat stabilizer, a dye and an antifoaming agent. Such additives are well known to those skilled in the art, and described in literature.

In a liquid crystal display device having the polymer sustained alignment (PSA) mode, the composition contains a polymer. The polymerizable compound is added for the purpose of forming the polymer in the composition. First, the composition in which a small amount of the polymerizable compound is added is injected into the device. Next, the composition is irradiated with ultraviolet light while voltage is applied between substrates of the device. The polymerizable compound is polymerized to form a network structure of the polymer in the liquid crystal composition. In the composition, alignment of liquid crystal molecules can be controlled by the polymer, and therefore a response time in the device is shortened and also image persistence is improved.

Preferred examples of the polymerizable compound include acrylate, methacrylate, a vinyl compound, a vinyloxy compound, propenyl ether, an epoxy compound (oxirane, oxetane) and vinyl ketone. Further preferred examples include a compound having at least one piece of acryloyloxy and a compound having at least one piece of methacryloyloxy. Still further preferred example also include a compound having both acryloyloxy and methacryloyloxy.

Still further preferred examples include compounds (M-1) to (M-18). In the compounds, $R^{25}$ to $R^{31}$ are independently hydrogen or methyl; $R^{32}$, $R^{33}$ and $R^{34}$ are independently hydrogen or alkyl having 1 to 5 carbons, at least one piece of $R^{32}$, $R^{33}$ and $R^{34}$ is alkyl having 1 to 5 carbons; s, v and x are independently 0 or 1; and t and u are independently integers of 1 to 10. $L^{21}$ to $L^{26}$ are independently hydrogen or fluorine; and $L^{27}$ and $L^{28}$ are independently hydrogen, fluorine or methyl.

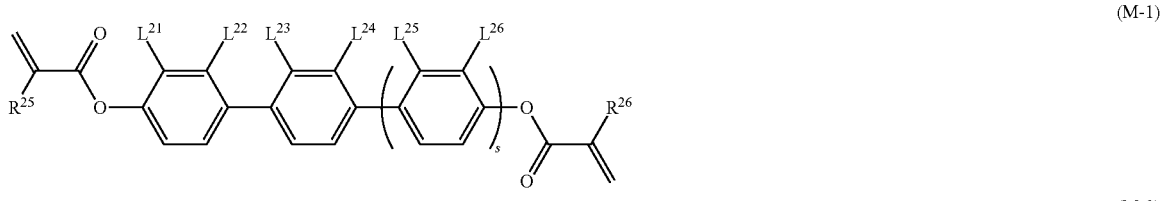

(M-1)

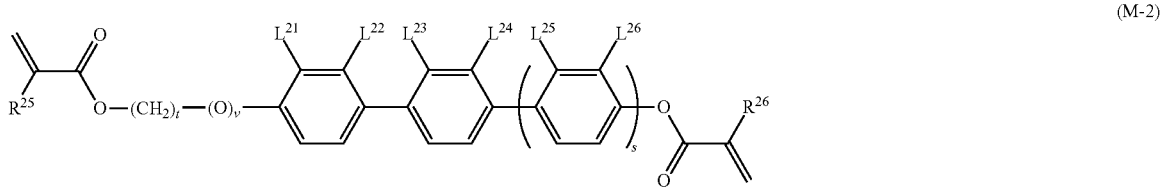

(M-2)

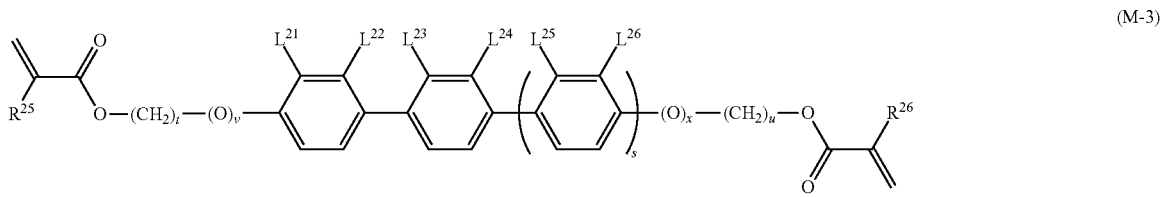

(M-3)

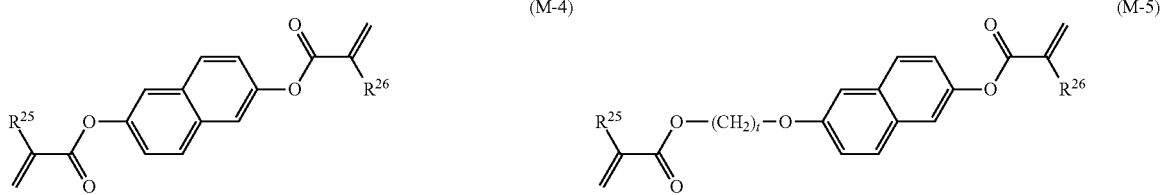

(M-4) (M-5)

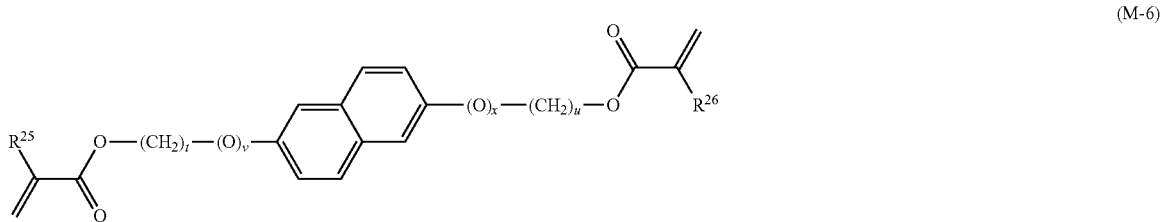

(M-6)

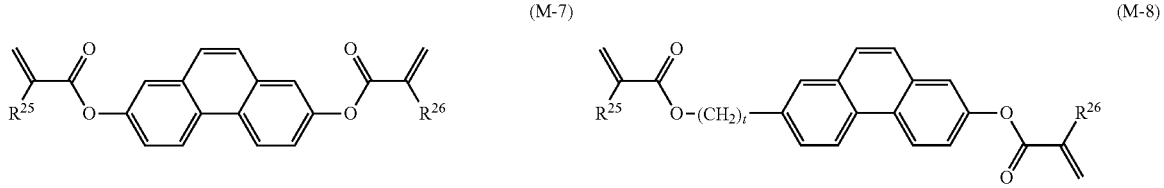

(M-7) (M-8)

(M-9)
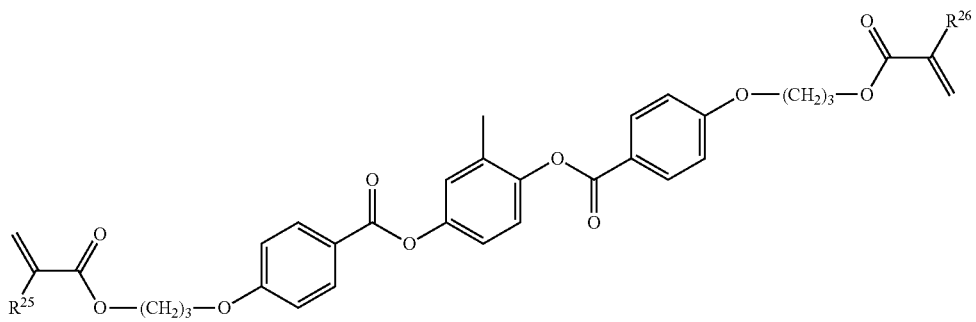
(M-10)
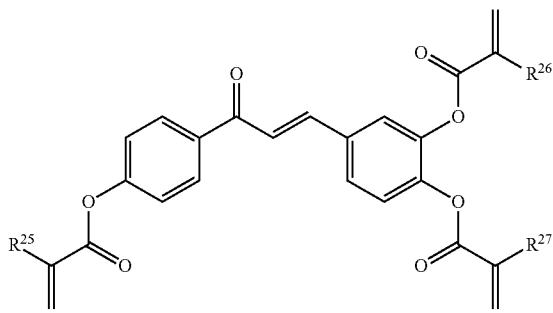
(M-11)
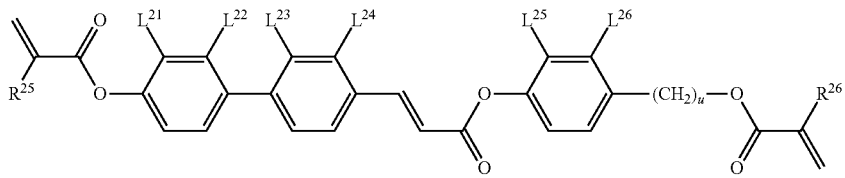
(M-12)
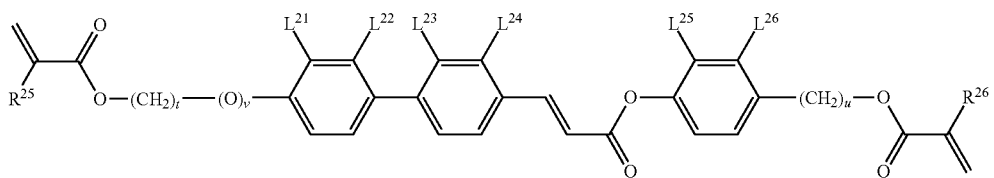
(M-13)
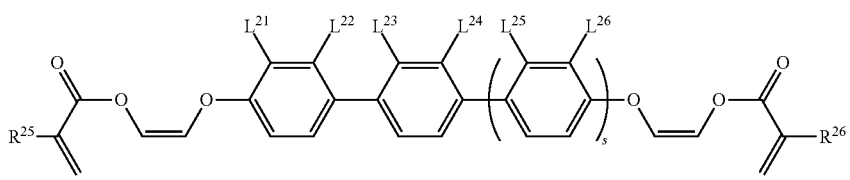
(M-14)
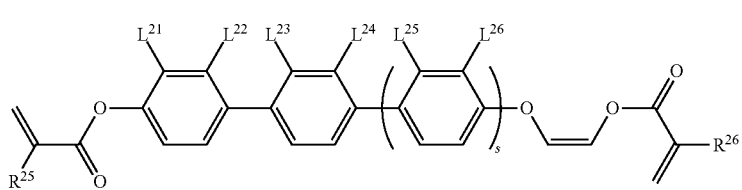

-continued

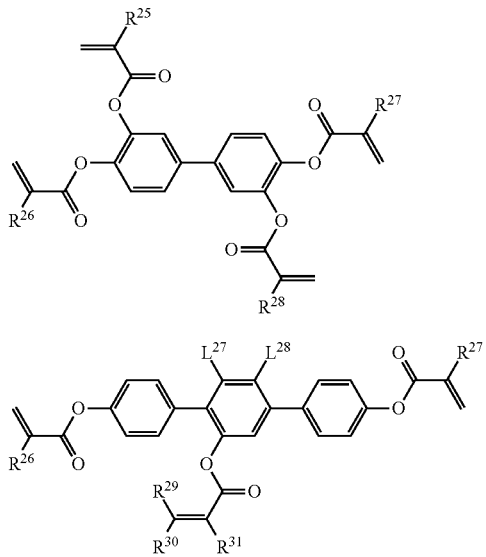

(M-15)

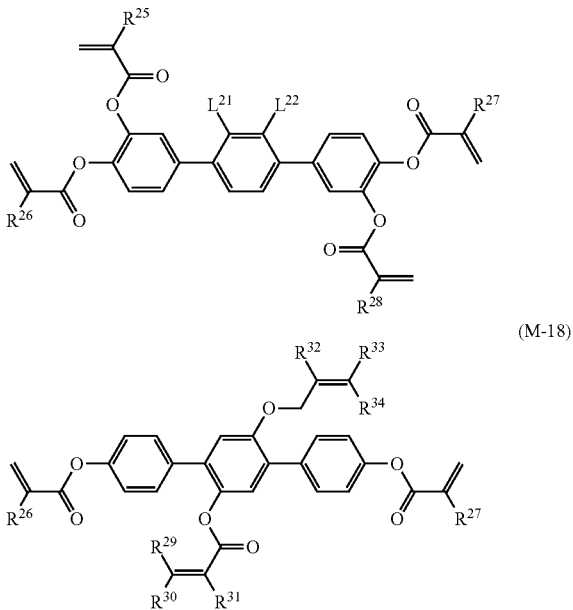

(M-16)

(M-17)

(M-18)

The polymerizable compound can be rapidly polymerized by adding the polymerizable initiator thereto. An amount of remaining polymerizable compound can be decreased by optimizing a reaction temperature. Specific examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series.

Additional examples of the photoradical polymerization initiator include 4-methoxyphenyl-2,4-bis(trichloromethyl)triazine, 2-(4-butoxystyryl)-5-trichloromethyl-1, 3, 4-oxadiazole, 9-phenylacridine, 9,10-benzphenazine, a mixture of benzophenone and Michler's ketone, a mixture of hexaarylbiimidazole and mercaptobenzimidazole, 1-(4-isopropylphenyl)-2-hydroxy-2-methylpropane-1-one, benzyldimethyl ketal, 2-methyl-1-[4-(methylthio)phenyl]-2-morpholinopropane-1-one, a mixture of 2,4-diethylxanthone and methyl p-dimethylaminobenzoate and a mixture of benzophenone and methyltriethanolamine.

After adding the optical radical polymerization initiator to the liquid crystal composition, polymerization can be performed by irradiating the liquid crystal composition with ultraviolet light while an electric field is applied thereto. However, an unreacted polymerization initiator or a decomposition product of the polymerization initiator may cause poor display such as image persistence in the device. Photopolymerization may be performed while no polymerization initiator is added in order to prevent such an event. A wavelength of light to be irradiated is preferably in the range of about 150 nanometers to about 500 nanometers. The wavelength is further preferably in the range of about 250 nanometers to about 450 nanometers and most preferably in the range of about 300 nanometers to about 400 nanometers.

Upon storing the polymerizable compound, the polymerization inhibitor may be added thereto in order to prevent polymerization. The polymerizable compound is ordinarily added to the composition without removing the polymerization inhibitor. Specific examples of the polymerization inhibitor include hydroquinone, a hydroquinone derivative such as methylhydroquinone, 4-t-butylcatechol, 4-methoxyphenol and phenothiazine.

The optically active compound is effective in inducing a helical structure in liquid crystal molecules to give a required twist angle, thereby preventing a reverse twist. A helical pitch can be adjusted by adding the optically active compound thereto. Two or more optically active compounds may be added thereto for the purpose of adjusting temperature dependence of the helical pitch. Preferred examples of the optically active compound include compounds (Op-1) to (Op-18) described below. In compound (Op-18), ring J is 1,4-cyclohexylene or 1,4-phenylene, and $R^{28}$ is alkyl having 1 to 10 carbons.

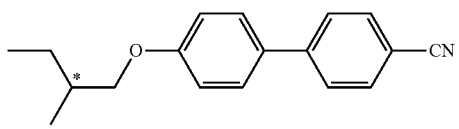

(Op-1)

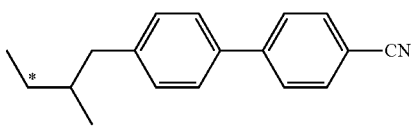

(Op-2)

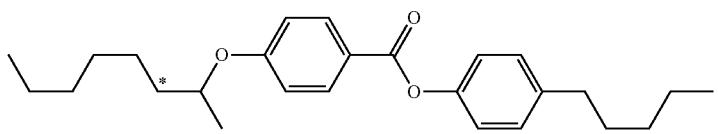

(Op-3)

-continued
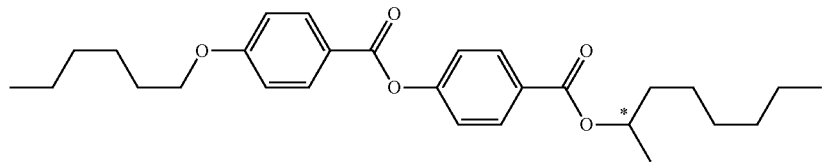
(Op-4)
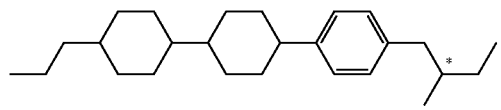
(Op-5)
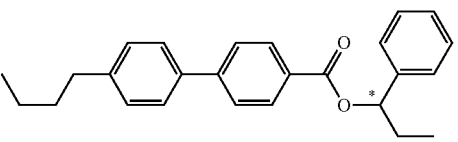
(Op-6)
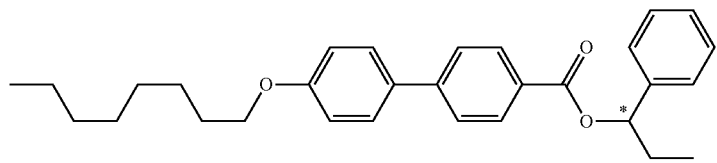
(Op-7)
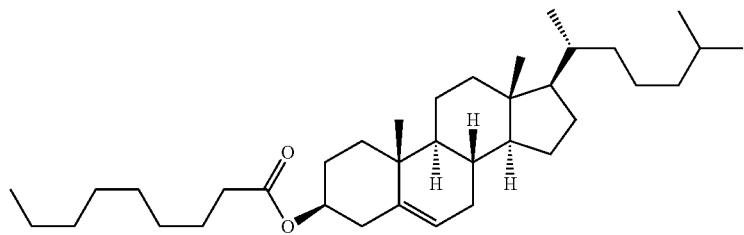
(Op-8)
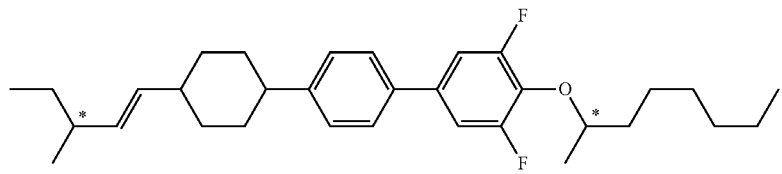
(Op-9)
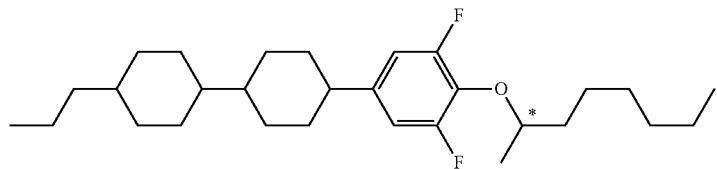
(Op-10)
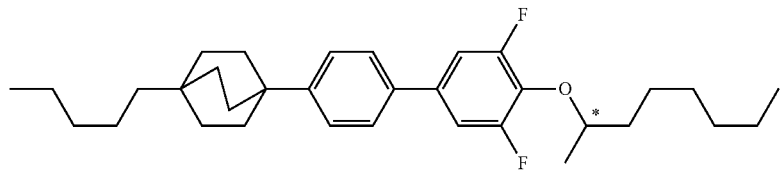
(Op-11)
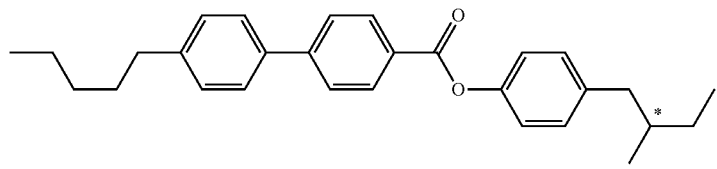
(Op-12)

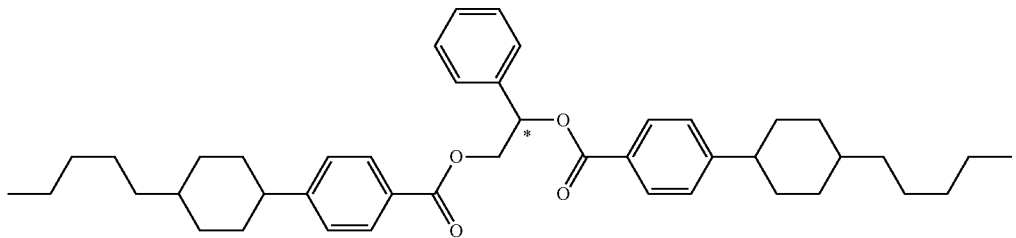
(Op-13)

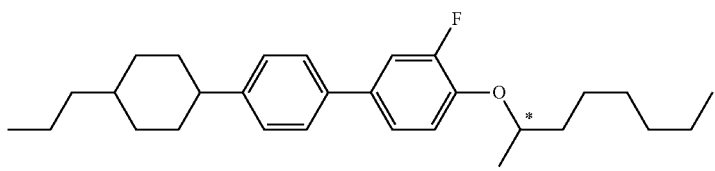
(Op-14)

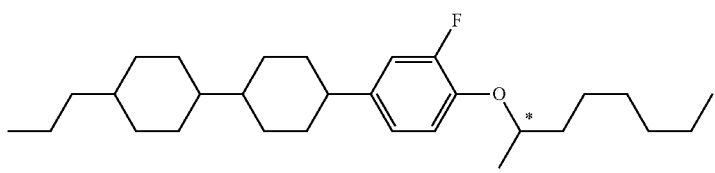
(Op-15)

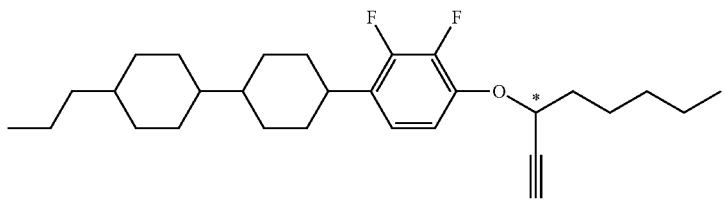
(Op-16)

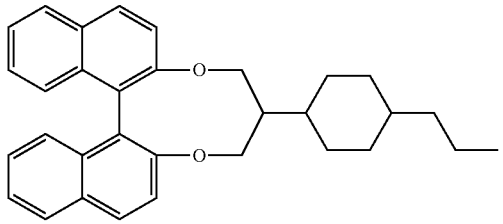
(Op-17)

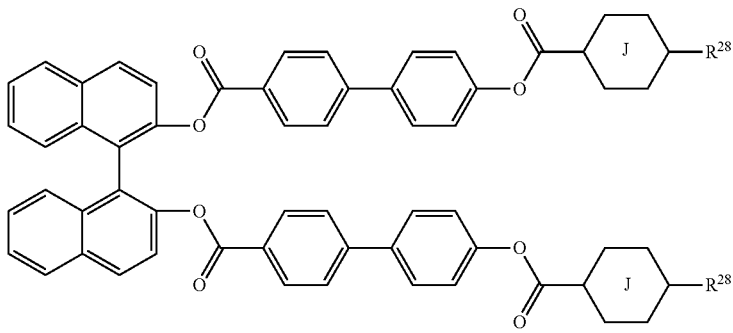
(Op-18)

The antioxidant is effective in maintaining a large voltage holding ratio. Preferred examples of the antioxidant include compounds (AO-1) and (AO-2) described below; and Irganox 415, Irganox 565, Irganox 1010, Irganox 1035, Irganox 3114, and Irganox 1098 (trade names; BASF SE). The ultraviolet light absorber is effective in preventing a decrease of the maximum temperature. Preferred examples of the ultraviolet light absorber include a benzophenone derivative, a benzoate derivative and a triazole derivative. Specific examples includes compounds (AO-3) and (AO-4) described below; Tinuvin 329, Tinuvin P, Tinuvin 326, Tinuvin 234, Tinuvin 213, Tinuvin 400, Tinuvin 328 and Tinuvin 99-2 (trade names; BASF SE); and 1,4-diazabicyclo [2.2.2]octane (DABCO).

The light stabilizer such as amine having steric hindrance is preferred for maintaining the large voltage holding ratio. Preferred examples of the light stabilizer include compounds (AO-5), (AO-6) and (AO-7) described below; Tinuvin 144, Tinuvin 765 and Tinuvin 770df (trade names; BASF SE); and LA-77Y and LA-77G (trade names; ADEKA corporation). The heat stabilizer is also effective in maintaining the large voltage holding ratio, and preferred examples include Irgafos 168 (trade name: BASF SE). A dichroic dye such as an azo dye or an anthraquinone dye is added to the composition to be adapted to a device having a guest host (GH) mode. The defoaming agent is effective in preventing foam formation. Preferred examples of the defoaming agent include dimethyl silicone oil and methylphenyl silicone oil.

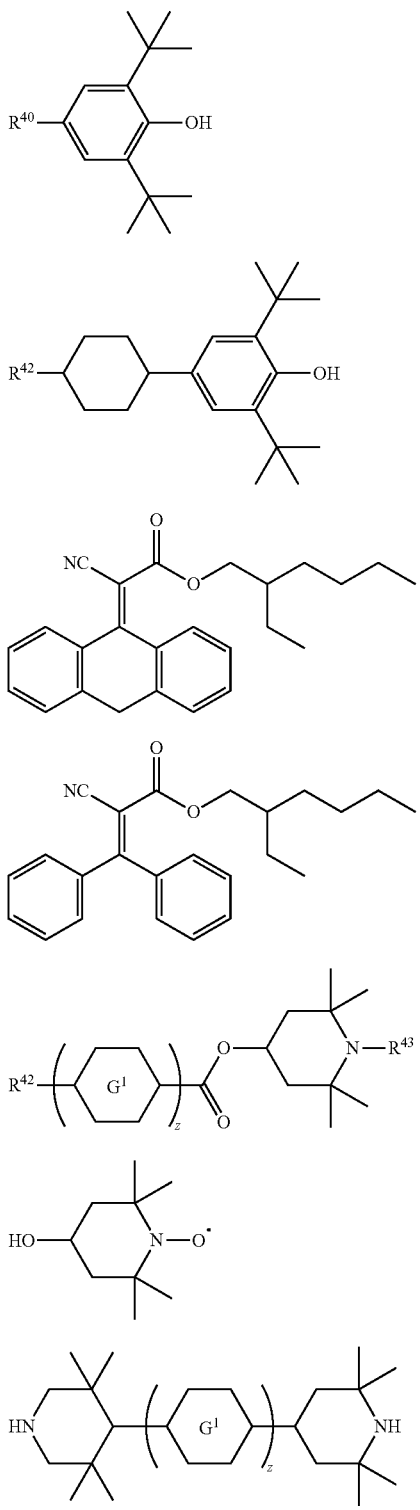

In compound (AO-1), $R^{40}$ is alkyl having 1 to 20 carbons, alkoxy having 1 to 20 carbons, —COOR$^{41}$ or —CH$_2$CH$_2$COOR$^{41}$, in which $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O. (oxygen radical); ring $G^1$ is 1,4-cyclohexylene or 1,4-phenylene; in compound (AO-7), ring $G^2$ is 1,4-cyclohexylene, 1,4-phenylene or 1,4-phenylene in which at least one piece of hydrogen is replaced by halogen; and in compounds (AO-5) and (AO-7), z is 1, 2 or 3.

4. Liquid Crystal Display Device

A liquid crystal composition can be used for a liquid crystal display device having an operating mode such as the PC mode, the TN mode, the STN mode, the OCB mode and the PSA mode, and driven by an active matrix. The composition can also be used for the liquid crystal display device having the operating mode such as the PC mode, the TN mode, the STN mode, the OCB mode, the VA mode and the IPS mode, and driven by a passive matrix mode. The devices can be applied to any of a reflective type, a transmissive type and a transflective type.

The composition is also suitable for a nematic curvilinear aligned phase device (NCAP), and the composition is microencapsulated herein. The composition can also be used for a polymer dispersed liquid crystal display device (PDLCD) and a polymer network liquid crystal display device (PNLCD). In the composition, a lot of polymerizable compounds are added. Meanwhile, when an adding amount of the polymerizable compound is in the range of about 10% by weight or less based on the weight of the liquid crystal composition, the liquid crystal display device having the PSA mode can be prepared. A preferred proportion is in the range of about 0.1% by weight to about 2% by weight. A further preferred proportion is in the range of about 0.2% by weight to about 1.0% by weight. The device having the PSA mode can be driven by a driving mode such as the active matrix or the passive matrix. Such devices can be applied to any of the reflective type, the transmissive type and the transflective type.

EXAMPLES

The invention is described in more detail by way of Examples (including Synthesis Examples and Use Examples). The invention is not limited by the Examples. The invention includes a mixture of a composition in Use Example 1 and a composition in Use Example 2. The invention also includes a composition prepared by mixing at least two of compositions in Use Examples.

1. Example of Compound (1)

Compound (1) was prepared according to procedures described below. The thus prepared compound was identified by a method such as an NMR analysis. Physical properties of the compound and the composition and characteristics of a device were measured by methods described below.

NMR analysis: DRX-500 made by Bruker BioSpin Corporation was used for measurement. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, CFCl$_3$ was used as an internal standard, and measurement was carried out under conditions of 24 times of accumulation. In the explanation of a nuclear magnetic resonance spectrum, s, d, t, q, quin, sex, m and br stand for a singlet, a doublet, a triplet, a quartet, a quintet, a sextet, a multiplet and br being broad, respectively.

Gas chromatographic analysis: GC-2010 Gas Chromatograph made by Shimadzu Corporation was used for measurement. Capillary column DB-1 (length: 60 m, bore: 0.25 mm, film thickness: 0.25 μm) made by Agilent Technologies, Inc. was used. Helium (1 mL/minute) was used as a carrier gas. A temperature of a sample vaporizing chamber was set to 300° C. and a detector (FID) part was also set to 300° C. A sample was dissolved in acetone to prepare a solution of 1% by weight, and then 1 microliter of the solution obtained was injected into the sample vaporizing chamber. GC Solution system made by Shimadzu Corporation or the like was used as a recorder.

HPLC analysis: Prominence (LC-20 AD; SPD-20A) made by Shimadzu Corporation was used for measurement. As a column, YMC-Pack ODS-A (length: 150 mm, bore: 4.6 mm, particle diameter: 5 μm) made by YMC Co., Ltd. was used. An elution liquid in which acetonitrile and water are appropriately mixed was used. An UV detector, a RI detector, a CORONA detector and so forth were appropriately used as a detector. A detection wavelength was set at 254 nm when the UV detector was used. A sample was dissolved in acetonitrile to prepare a solution of 0.1% by weight, and then 1 microliter of the solution was injected into a sample chamber. C-R7Aplus made by Shimadzu Corporation was used as a recorder.

Ultraviolet-visible spectroscopic analysis: PharmaSpec UV-1700 made by Shimadzu Corporation was used for measurement. A detection wavelength was adjusted in the range of 190 nanometers to 700 nanometers. A sample was dissolved in acetonitrile to prepare a solution of 0.01 mmol/L, and the solution was put in a quartz cell (optical path length: 1 cm) and measured.

Sample for measurement: Upon measuring phase structure and a transition temperature (a clearing temperature, a melting temperature, a polymerization starting temperature or the like), a compound itself was used as a sample. Upon measuring physical properties such as a maximum temperature of a nematic phase, viscosity, an optical anisotropy and dielectric anisotropy, a mixture of a compound and a base liquid crystal was used as a sample.

When the sample prepared by mixing the compound with the base liquid crystal was used, measurement was carried out according to the method described below. The sample was prepared by mixing 15% by weight of the compound and 85% by weight of the base liquid crystal. Then, extrapolated values were calculated from measured values of the sample, according to the extrapolation method represented by the equation below, and the extrapolated values were described:

{Extrapolated value}={100×(measured value of a sample)−(% by weight of a base liquid crystal)×(measured value of the base liquid crystal)}/(% by weight of a compound).

When crystals (or a smectic phase) precipitated at 25° C. at the proportion, a proportion of the compound to the base liquid crystal was changed in the order of (10% by weight: 90% by weight), (5% by weight: 95% by weight) and (1% by weight: 99% by weight). Physical properties of the sample were measured at a proportion at which no crystal (or no smectic phase) precipitate at 25° C. In addition, unless otherwise noted, a proportion of the compound to the base liquid crystal is 15% by weight: 85% by weight.

When dielectric anisotropy of the compound was zero or positive, base liquid crystal (A) described below was used. A proportion of each component was expressed in terms of % by weight.

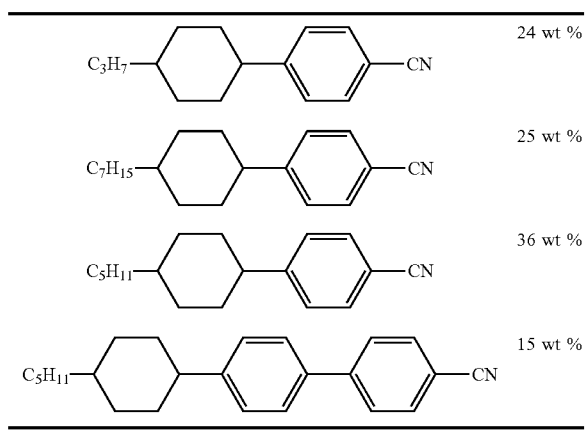

When the dielectric anisotropy of a compound was zero or negative, base liquid crystal (B) described below was used. A proportion of each component was expressed in terms of % by weight.

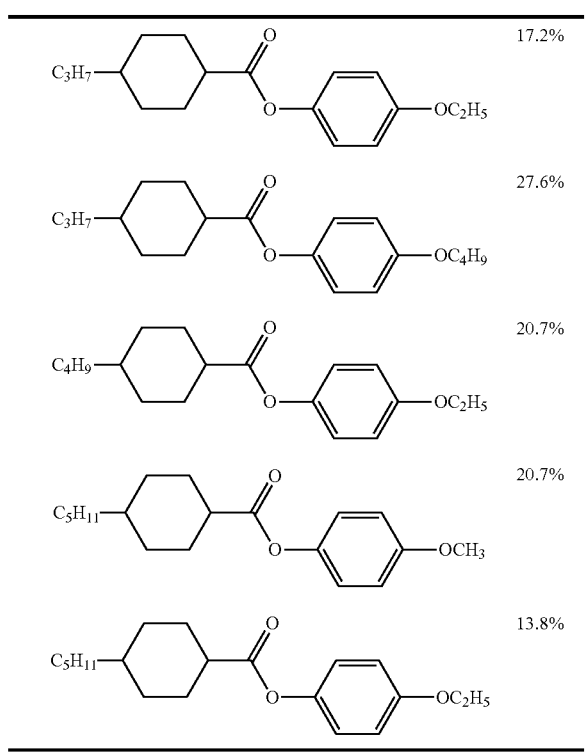

Measuring method: Measurement of characteristics was carried out by the methods described below. Most of the measuring methods are described in the Standard of Japan Electronics and Information Technology Industries Association (JEITA EIAJ ED-2521B) discussed and established in JEITA. Methods modified thereon were also applied. No thin film transistor (TFT) was attached to a TN device used for measurement.

(1) Phase structure: A sample was placed on a hot plate of a melting point apparatus (FP-52 Hot Stage made by Mettler-Toledo International Inc.) equipped with a polarizing microscope. A state of phase and a change thereof were observed with the polarizing microscope while the sample was heated at a rate of 3° C. per minute, and a kind of the phase was specified.

(2) Transition temperature (° C.): For measurement, a scanning calorimeter Diamond DSC System made by PerkinElmer, Inc., or a high-sensitivity differential scanning calorimeter X-DSC7000 made by SII NanoTechnology, Inc. was used. A sample was heated and then cooled at a rate of 3° C. per minute, and a starting point of an endothermic peak or an exothermic peak caused by a phase change of the sample was determined by extrapolation, and thus a transition temperature was determined. A melting point and a polymerization start temperature of a compound are also measured using the apparatus. Temperature at which a compound undergoes transition from a solid to a liquid crystal phase such as a smectic phase and a nematic phase may be occasionally abbreviated as "minimum temperature of the liquid crystal phase." Temperature at which a compound undergoes transition from the liquid crystal phase to liquid may be occasionally abbreviated as "clearing point."

A crystal was expressed as C. When kinds of the crystals were distinguishable, each of the crystals was expressed as $C_1$ or $C_2$. A smectic phase or a nematic phase was expressed as S or N. When a smectic A phase, a smectic B phase, a smectic C phase or a smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that the transition temperature from the crystal to the nematic phase was 50.0° C., and the transition temperature from the nematic phase to the liquid was 100.0° C.

(5) Compatibility of compound: Some compounds having a similar structure were mixed and a base liquid crystal having a nematic phase was prepared. A compound to be measured was added to the base liquid crystal. An example of a mixing proportion was 15% by weight of the compound and 85% by weight of the base liquid crystal. The compositions were kept for 30 days at low temperatures of −20° C., −30° C. and so forth. Whether or not a part of the composition was changed to crystals (or a smectic phase) was observed. A mixing proportion and a storage temperature were changed as required. From the measured result, a condition whether or not the crystals (or the smectic phase) precipitated was determined. The condition was a measure of compatibility.

(4) Maximum temperature of nematic phase ($T_{NI}$ or NI; ° C.): A sample was placed on a hot plate of a melting point apparatus equipped with a polarizing microscope, and heated at a rate of 1° C. per minute. Temperature when a part of the sample began to change from a nematic phase to an isotropic liquid was measured. When the sample was a mixture of compound (1) and a base liquid crystal, a maximum temperature was expressed as a symbol $T_{NI}$. When the sample was a mixture of compound (1) and a compound such as components (b), (c) and (d), the maximum temperature was expressed as a symbol NI. A higher limit of a temperature range of the nematic phase may be occasionally abbreviated as "maximum temperature."

(5) Minimum temperature of nematic phase ($T_c$; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_c$ was expressed as $T_c<−20°$ C. A minimum temperature of the nematic phase may be occasionally abbreviated as "minimum temperature."

(6) Viscosity (bulk viscosity; η; measured at 20° C.; mPa·s): A cone-plate (E type) rotational viscometer made by Tokyo Keiki, Inc. was used for measurement.

(7) Optical anisotropy (refractive index anisotropy; measured at 25° C.; Δn): Measurement was carried out by an Abbe refractometer having a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when a direction of polarized light was perpendicular to a direction of rubbing. A value of optical anisotropy was calculated from the equation: Δn=n∥−n⊥.

(8) Specific resistance (ρ; measured at 25 C; Ωcm): Into a vessel equipped with electrodes, 1.0 milliliter of a sample was injected. A DC voltage (10V) was applied to the vessel, and a DC current after 10 seconds was measured. A specific resistance was calculated from the following equation: (Specific resistance)={(voltage)×(electric capacity of a vessel)}/ {(direct current)×(dielectric constant of vacuum)}.

(9) Voltage holding ratio (VHR-1; measured at 25° C.; %): A TN device used for measurement had a polyimide alignment film, and a distance between two glass substrates (cell gap) was 5 micrometers. A sample was put in the device, and the device was sealed with an ultraviolet-curable adhesive. The device was charged by applying a pulse voltage (60 microseconds at 5 V). A decaying voltage was measured for 16.7 milliseconds with a high-speed voltmeter, and area A between a voltage curve and a horizontal axis in a unit cycle was determined. Area B was an area without decay. A voltage holding ratio was expressed in terms of a percentage of area A to area B.

(10) Voltage holding ratio (VHR-2; measured at 80° C.; %): A voltage holding ratio was measured by a method described above except that the voltage holding ratio was measured at 80° C. in place of 25° C. The thus obtained value was expressed in terms of VHR-2.

The measuring method of the characteristics may be different between a sample having a positive dielectric anisotropy and a sample having a negative dielectric anisotropy. When the dielectric anisotropy was positive, the measuring method was described in sections (11a) to (15a). When the dielectric anisotropy was negative, the measuring method was described in sections (11b) to (15b).

(11a) Viscosity (Rotational Viscosity; γ1; Measured at 25° C.; mPa·s)

Positive dielectric anisotropy: Measurement was carried out according to a method described in M. Imai et al., Molecular Crystals and Liquid Crystals, Vol. 259, p. 37 (1995). A sample was put in a TN device in which a twist angle was 0 degrees and a distance between two glass substrates (cell gap) was 5 micrometers. Voltage was applied stepwise to the device in the range of 16 V to 19.5 V at an increment of 0.5 V. After 0.2 seconds without voltage application, voltage was repeatedly applied under conditions of only one rectangular wave (rectangular pulse; 0.2 seconds) and no voltage application (2 seconds). A peak current and a peak time of a transient current generated by the applied voltage were measured. A value of rotational viscosity was obtained from the measured values and calculation equation (8) on page 40 of the paper presented by M. Imai et al. A value of dielectric anisotropy required for the calculation was determined using the device by which the rotational viscosity was measured and by a method described below.

(11b) Viscosity (Rotational Viscosity; γ1; Measured at 25° C.; mPa·s)

Negative dielectric anisotropy: Measurement was carried out according to a method described in M. Imai et al., Molecular Crystals and Liquid Crystals, Vol. 259, p. 37 (1995). A sample was put in a VA device in which a distance between two glass substrates (cell gap) was 20 micrometers. Voltage was applied stepwise to the device in the range of 39 V to 50 V at an increment of 1 V. After 0.2 seconds without voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) on page 40 of the paper presented by M. Imai et al. As dielectric anisotropy required for the calculation, a value measured in the section of dielectric anisotropy described below was used.

(12a) Dielectric Anisotropy (as; Measured at 25° C.)

Positive dielectric anisotropy: A sample was put in a TN device in which a distance between two glass substrates (cell gap) was 9 micrometers and a twist angle was 80 degrees. Sine waves (10 V, 1 kHz) were applied to the device, and after 2 seconds, a dielectric constant (∈∥) in a major axis direction of liquid crystal molecules was measured. Sine waves (0.5 V, 1 kHz) were applied to the device, and after 2 seconds, a dielectric constant (∈⊥) in a minor axis direction of liquid crystal molecules was measured. A value of dielectric anisotropy was calculated from an equation: Δ∈=∈∥−∈⊥.

(12b) Dielectric Anisotropy (Δ∈; Measured at 25° C.)

Negative dielectric anisotropy: A value of dielectric anisotropy was calculated from an equation: Δ∈=∈∥−∈⊥. Dielectric constants (∈∥ and ∈⊥) were measured as described below.

(1) Measurement of dielectric constant (∈∥): An ethanol solution (20 mL) of octadecyl triethoxysilane (0.16 mL) was applied to a well-cleaned glass substrate. After rotating the glass substrate with a spinner, the glass substrate was heated at 150° C. for 1 hour. A sample was put in a VA device in which a distance between two glass substrates (cell gap) was 4 micrometers, and the device was sealed with an ultraviolet-curable adhesive. Sine waves (0.5 V, 1 kHz) were applied to the device, and after 2 seconds, a dielectric constant (∈∥) in a major axis direction of liquid crystal molecules was measured.

(2) Measurement of dielectric constant (∈⊥): A polyimide solution was applied to a well-cleaned glass substrate. After calcining the glass substrate, a rubbing treatment was applied to the alignment film obtained. A sample was put in a TN device in which a distance between two glass substrates (cell gap) was 9 micrometers and a twist angle was 80 degrees. Sine waves (0.5 V, 1 kHz) were applied to the device, and after 2 seconds, a dielectric constant (SI) in a minor axis direction of liquid crystal molecules was measured.

(13a) Elastic Constant (K; Measured at 25° C.; pN)

Positive dielectric anisotropy: HP4284A LCR Meter made by Yokogawa-Hewlett-Packard Co. was used for measurement. A sample was put in a horizontal alignment device in which a distance between two glass substrates (cell gap) was 20 micrometers. An electric charge of 0 V to 20 V was applied to the device, and electrostatic capacity and an applied voltage were measured. The measured values were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in equation (3.18) on page 171. Elastic constant K was expressed using a mean value of the thus determined $K_{11}$, $K_{22}$ and $K_{33}$.

(13b) Elastic Constant ($K_{11}$ and $K_{33}$; Measured at 25° C.; pN)

Negative dielectric anisotropy: Elastic Constant Measurement System Model EC-1 made by TOYO Corporation was used for measurement. A sample was put in a vertical alignment device in which a distance between two glass substrates (cell gap) was 20 micrometers. An electric charge of 20 V to 0 V was applied to the device, and electrostatic capacity and an applied voltage were measured. Values of electrostatic capacity (C) and applied voltage (V) were fitted to equation (2.98) and equation (2.101) on page 75 of the "Liquid Crystal Device Handbook (Ekisho Debaisu Handobukku, in Japanese)" (The Nikkan Kogyo Shimbun, Ltd.), and a value of elastic constant was obtained from equation (2.100).

(14a) Threshold Voltage (Vth; Measured at 25° C.; V)

Positive dielectric anisotropy: An LCD-5100 luminance meter made by Otsuka Electronics Co., Ltd. was used for measurement. A light source was a halogen lamp. A sample was put in a normally white mode TN device in which a distance between two glass substrates (cell gap) was 0.45/An (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A threshold voltage was expressed in terms of a voltage at 90% transmittance.

(14b) Threshold Voltage (Vth; Measured at 25° C.; V)

Negative dielectric anisotropy: An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A threshold voltage was expressed in terms of a voltage at 10% transmittance.

(15a) Response Time (T; Measured at 25° C.; ms)

Positive dielectric anisotropy: An LCD-5100 luminance meter made by Otsuka Electronics Co., Ltd. was used for measurement. A light source was a halogen lamp. A low-pass filter was set at 5 kHz. A sample was put in a normally white mode TN device in which a distance between two glass substrates (cell gap) was 5.0 micrometers and a twist angle was 80 degrees. Rectangular waves (60 Hz, 5 V, 0.5 sec) was applied to the device. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. Rise time (τr: millisecond) is time taken to change 90% of transmissivity to 10%. Fall time (τf: millisecond) is time taken to change 10% of transmissivity to 90%. Response time was presented by a sum of the thus rise time and fall time.

(15b) Response Time (T; Measured at 25 C; ms)

Negative dielectric anisotropy: An LCD-5100 luminance meter made by Otsuka Electronics Co., Ltd. was used for measurement. A light source was a halogen lamp. A low-pass filter was set at 5 kHz. A sample was put in a normally black mode PVA device in which a distance between two glass substrates (cell gap) was 3.2 micrometers and a rubbing direction was anti-parallel. The device was sealed with an ultraviolet-curable adhesive. The device was applied with a voltage of a little exceeding a threshold voltage for 1 minute, and then was irradiated with ultraviolet light of 23.5 mW/cm$^2$ for 8 minutes, while applying a voltage of 5.6 V. Rectangular waves (60 Hz, 10 V, 0.5 sec) was applied to the device. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. Response time was a period of time required for a change from 90% transmittance to 10% transmittance (fall time; millisecond).

Synthesis Example 1

Compound (1-1-1)

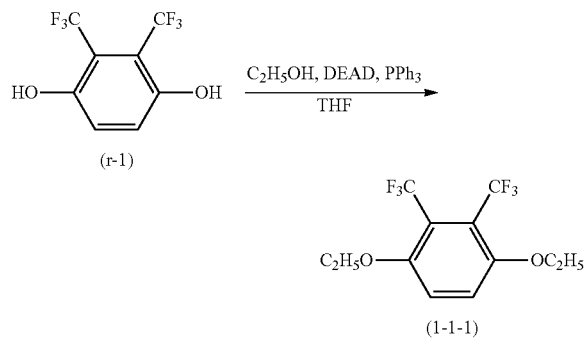

Compound (r-1) (10.0 g, 26.9 mmol), ethanol (3.9 g, 85.3 mmol) and triphenyl phosphine (25.6 g, 97.5 mmol) were dissolved in tetrahydrofuran (THF; 100 mL), and the resulting mixture was cooled in an ice bath. Diethyl azodicarboxylate (DEAD; a toluene solution of 2.2 mol/L; 44.3 mL, 97.5 mmol) was added dropwise thereto, and the resulting mixture was stirred at room temperature overnight. The solvent was distilled off, and the residue was purified by silica gel column chromatography (hexane), and then the resulting mixture was recrystallized from heptane/ethanol=1/3 (volume ratio) to obtain 1.2 g of compound (1-1-1).

$^1$H-NMR (CDCl$_3$; δ ppm): 7.16 (s, 2H), 4.07 (q, 4H), 1.41 (t, 6H).

In measuring a transition temperature, compound (1-1-1) itself was used as a sample. In measuring maximum temperature (T$_{NI}$), dielectric anisotropy (Δ∈) and optical anisotropy (Δn), a mixture of compound (1-1-1) and base liquid crystal (B) was used as the sample. A same rule also applies to compounds prepared below.

Transition temperature: C$_1$ 49.9 C$_2$ 68.8 I. T$_{NI}$=−116.1° C., Δ∈=−9.11, and Δn=−0.017.

Synthesis Example 2

Compound (1-1-3)

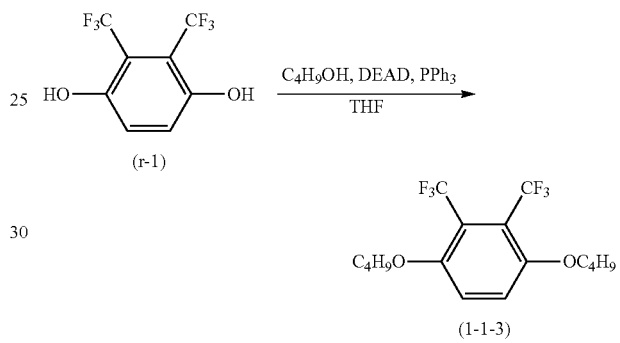

Compound (r-1) (10.0 g, 26.9 mmol), 1-butanol (6.3 g, 85.3 mmol), triphenyl phosphine (25.6 g, 97.5 mmol) were dissolved in tetrahydrofuran (THF; 100 mL), and the resulting mixture was cooled in an ice bath. DEAD (a toluene solution of 2.2 mol/L; 44.3 mL, 97.5 mmol) was added dropwise thereto, and the resulting mixture was stirred at room temperature overnight. The solvent was distilled off, and the residue was purified by silica gel column chromatography (hexane), and then the resulting mixture was recrystallized from ethanol to obtain 2.38 g of compound (1-1-3).

$^1$H-NMR (CDCl$_3$; δ ppm): 7.15 (s, 2H), 3.99 (t, 4H), 1.78 (quin, 4H), 1.50 (sex, 4H), 0.97 (t, 6H). Transition temperature: C 17.7 I. T$_{NI}$=−101.4° C., Δ∈=−10.1 and Δn=−0.003.

Synthesis Example 3

Compound (1-1-14)

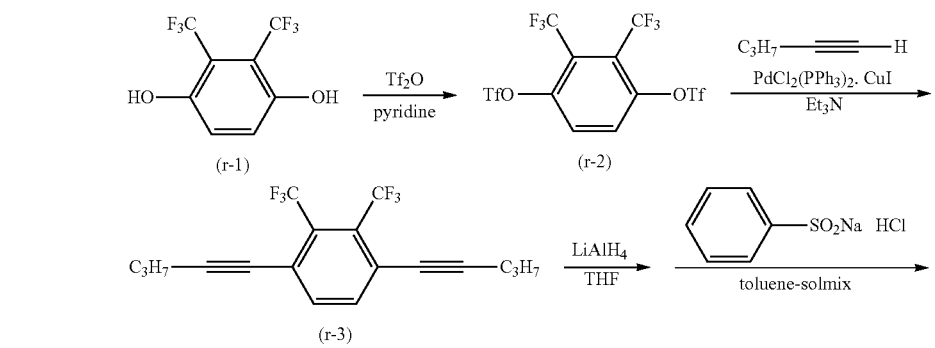

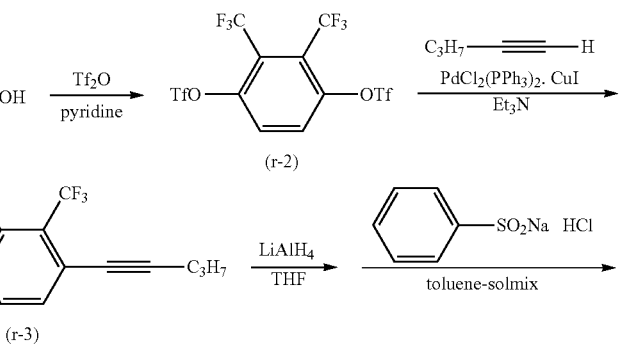

-continued

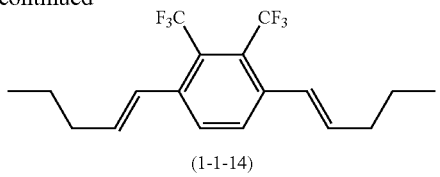

(1-1-14)

First Step: Preparation of Compound (r-2)

Compound (r-1) (18.0 g, 73.1 mmol) of compound (r-2) was dissolved in pyridine (100 mL), and the resulting mixture was cooled in an ice bath. Trifluoromethanesulfonic anhydride (29.7 mL, 175.5 mmol) was added dropwise thereto, and the resulting mixture was stirred at room temperature overnight. The solvent was distilled off and the residue was dissolved in diethyl ether, the ether solution was washed with 2M hydrochloric acid, and saturated brine, and dried over anhydrous magnesium sulfate. The solvent was distilled off, and the residue was purified by silica gel column chromatography (hexane/ethyl acetate=9/1 in a volume ratio) to obtain 34.9 g of compound (r-2).

Second Step: Preparation of Compound (r-3)

Compound (r-2) (15.1 g, 29.5 mmol), dichlorobistriphenylphosphine palladium (II) (0.202 g, 0.29 mmol) and copper iodide (I) (0.067 g, 0.35 mmol) were dissolved in triethylamine (60 mL), pent-1-yn (4.31 g, 63.3 mmol) was added dropwise thereto, and the resulting mixture was stirred at room temperature overnight for seven days. The solvent was distilled off, the residue was dissolved in toluene and the toluene solution was washed with a saturated aqueous solution of ammonium chloride, water and saturated brine, and then dried over anhydrous magnesium sulfate. The solvent was distilled off, and the residue was purified by silica gel column chromatography (heptane) to obtain 7.80 g of compound (r-3).

Third Step: Preparation of Compound (1-1-14)

Compound (r-3) (3.80 g, 11.0 mmol) was dissolved in THF (50 mL), lithium aluminum hydride (1.25 g, 32.9 mmol) was added thereto, and the resulting mixture was heated under reflux for 21 hours. The reaction mixture was cooled to room temperature, and then poured into ice water and subjected to extraction with ethyl acetate. The extract was washed with 1 M hydrochloric acid, and water, and dried over anhydrous magnesium sulfate. The solvent was distilled off, and the residue was purified by silica gel column chromatography (heptane). The resulting mixture was dissolved in acetonitrile (8 mL), and sodium benzenesulfinate dihydrate (0.46 g, 2.28 mmol) and 6M hydrochloric acid (0.38 mL) were further added thereto, and the resulting mixture was heated under reflux for 6 hours. After the resulting mixture was cooled to room temperature, the reaction mixture was poured into heptane. The organic layer was washed with water and brine, and then dried over anhydrous magnesium sulfate. The solvent was distilled off, the residue was purified by silica gel column chromatography (heptane), and further the resulting mixture was recrystallized from methanol to obtain compound (1-1-14).

$^1$H-NMR (CDCl$_3$; δ ppm): 7.56 (s, 2H), 6.68 (d, 2H), 6.09 (tt, 2H), 2.22 (q, 4H), 1.52 (sex, 4H), 0.95 (t, 6H). Transition temperature: C 17.8 I. $T_{NI}$=−116.4° C., Δ∈=−4.37, Δn=0.014.

Synthesis Example 4

Compound (1-1-27)

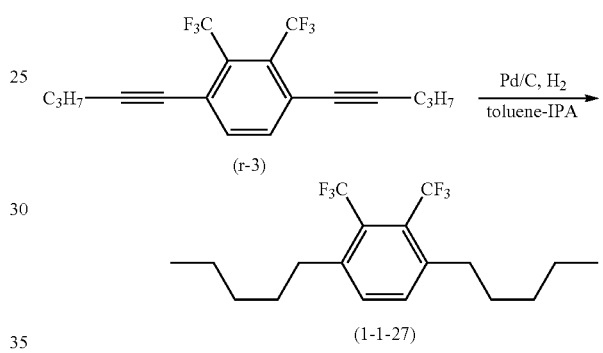

Compound (r-3) (3.00 g, 8.66 mmol) was dissolved in toluene (25 mL) and 2-propanol (25 mL), and Pd on carbon (0.17 g) was added thereto, the resulting mixture was stirred under a hydrogen atmosphere until no hydrogen was absorbed any more. Pd on carbon was filtrated off, and then the solvent was distilled off, the residue was purified by silica gel column chromatography (heptane), and further the resulting material was recrystallized from methanol to obtain compound (1-1-27).

$^1$H-NMR (CDCl$_3$; δ ppm): 7.36 (s, 2H), 2.75 (t, 4H), 1.62 (quin, 4H), 2.22 (q, 4H), 1.40-1.31 (m, 8H), 0.91 (t, 6H). Transition temperature: C 21.0 I. $T_{NI}$=−154.1° C., Δ∈=−2.36, Δn=−0.053.

Synthesis Example 5

Compound (1-2-20)

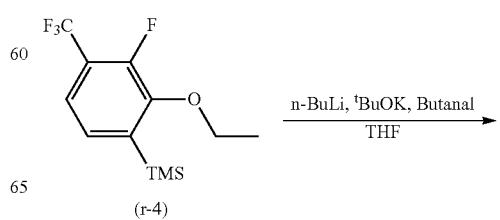

(r-4)

n-BuLi, $^t$BuOK, Butanal
THF

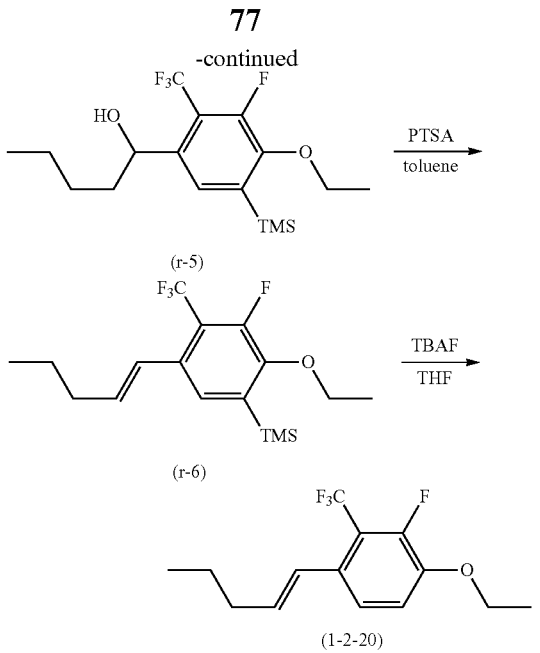

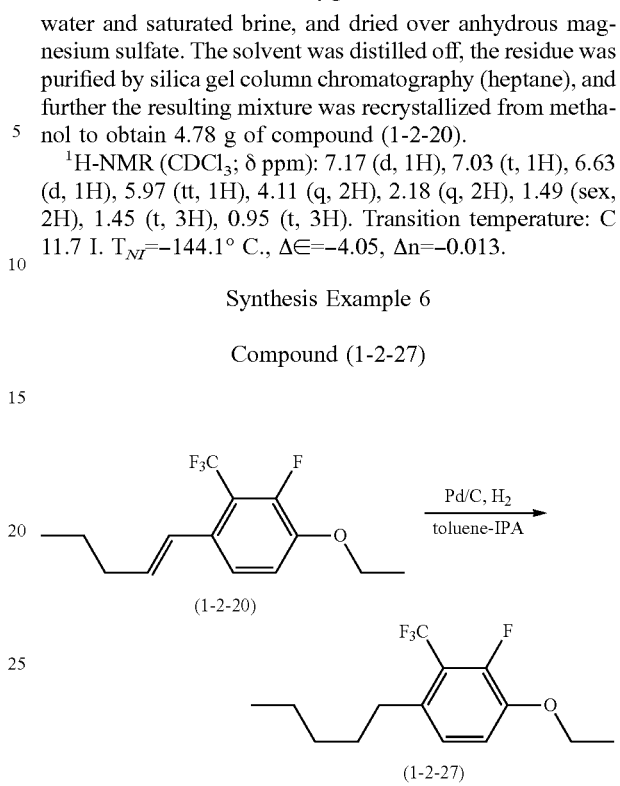

First Step: Preparation of Compound (r-4)

Compound (r-4) (10.0 g, 35.7 mmol) and t-BuOK (4.50 g, 40.1 mmol) were dissolved in THF (10 mL), the resulting material was cooled to −78° C., and then n-BuLi (a hexane solution of 1.6 M/L; 25.0 mL, 38.8 mmol) was added dropwise thereto, and the resulting mixture was stirred at the same temperature for 2 hours. Then, 1-butanal (3.37 g, 40.1 mmol) dissolved in THF (5 mL) was added dropwise thereto, and the resulting mixture was stirred at −78° C. for 3 hours. The reaction mixture was cooled to room temperature, and then poured into water. The resulting mixture was neutralized with an aqueous solution of ammonium chloride, and subjected to extraction with ethyl acetate. The extract was washed with water and saturated brine, and then dried over anhydrous sodium sulfate. The solvent was distilled off, and the residue was purified by silica gel column chromatography (heptane/ethyl acetate=9/1, volume ratio) to obtain 8.62 g of compound (r-5).

Second Step: Preparation of Compound (r-6)

Compound (r-5) (8.62 g, 23.5 mmol) was dissolved in toluene (80 mL), and p-toluenesulfonic acid monohydrate (0.23 g, 1.21 mmol) was added thereto, and then the resulting mixture was heated under reflux for 5 hours, while water produced was distilled off. The reaction mixture was cooled, and then poured into a saturated aqueous solution of sodium hydrogencarbonate. The organic layer was washed with water and saturated brine, and then dried over anhydrous magnesium sulfate. The solvent was distilled off, and the residue was purified by silica gel column chromatography (heptane) to obtain 6.37 g of compound (r-6).

Third Step: Preparation of Compound (1-2-20)

Compound (r-6) (6.37 g, 18.2 mmol) was dissolved in THF (50 mL), and tetrabutylammonium fluoride (a THF solution of 1.0 M/L; 19 mL, 19.0 mmol) was added dropwise thereto at a temperature of 10° C. or lower, and the resulting mixture was stirred at room temperature for 1 hour. The reaction mixture was poured into water, and subjected to extraction with toluene. The extract was washed with water and saturated brine, and dried over anhydrous magnesium sulfate. The solvent was distilled off, the residue was purified by silica gel column chromatography (heptane), and further the resulting mixture was recrystallized from methanol to obtain 4.78 g of compound (1-2-20).

$^1$H-NMR (CDCl$_3$; δ ppm): 7.17 (d, 1H), 7.03 (t, 1H), 6.63 (d, 1H), 5.97 (tt, 1H), 4.11 (q, 2H), 2.18 (q, 2H), 1.49 (sex, 2H), 1.45 (t, 3H), 0.95 (t, 3H). Transition temperature: C 11.7 I. $T_{NI}$=−144.1° C., Δ∈=−4.05, Δn=−0.013.

Synthesis Example 6

Compound (1-2-27)

Compound (1-2-20) (3.61 g, 13.1 mmol) was dissolved in toluene (25 mL) and 2-propanol (25 mL), Pd on carbon (0.14 g) was added thereto, and the resulting mixture was stirred under a hydrogen atmosphere until no hydrogen was absorbed. Pd on carbon was filtrated off, and then the solvent was distilled off. The residue was purified by silica gel column chromatography (heptane/toluene=9/1 in a volume ratio), and further the resulting mixture was recrystallized from methanol to obtain 2.47 g of compound (1-2-27).

$^1$H-NMR (CDCl$_3$; δ ppm): 7.02 (t, 1H), 6.94 (d, 1H), 4.08 (q, 2H), 2.69 (td, 2H), 1.55 (quin, 2H), 1.44 (t, 3H), 1.35-1.29 (m, 4H), 0.89 (t, 3H). Transition temperature: C 8.9 I. $T_{NI}$=−166.1° C., Δ∈=−2.78, Δn=−0.066.

Synthesis Example 7

Compound (1-2-9)

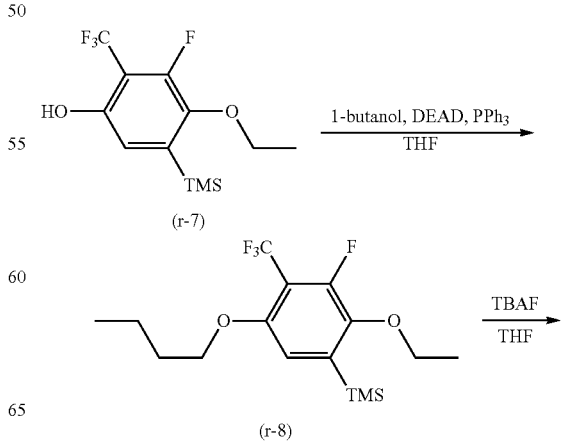

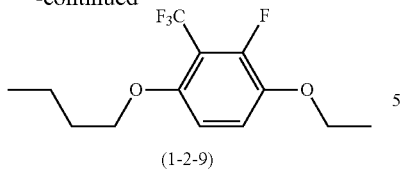

(1-2-9)

First Step: Preparation of Compound (r-8)

Compound (r-7) (6.64 g, 22.4 mmol), 1-butanol (1.84 g, 24.8 mmol) and triphenyl phosphine (6.52 g, 24.9 mmol) were dissolved in THF (70 mL), DEAD (a hexane solution of 2.2 M/L; 11.2 mL, 24.6 mmol) was added dropwise thereto under ice-cooling, and the resulting mixture was further stirred at room temperature for 2 hours. The solvent was distilled off, and then the residue was purified by silica gel column chromatography (heptane/toluene=4/1 in a volume ratio) to obtain 6.27 g of compound (r-8).

Third Step: Preparation of Compound (1-2-9)

Compound (r-8) (6.27 g, 17.8 mmol) was dissolved in THF (50 mL), Tetrabutylammonium fluoride (a THF solution of 1.0 M/L; 18 mL, 18.0 mmol) was added dropwise thereto at a temperature of 10° C. or lower, and the resulting mixture was stirred at room temperature for 1 hour. The reaction mixture was poured into water and subjected to extraction with toluene. The extract was washed with water and saturated brine and dried over anhydrous magnesium sulfate. The solvent was distilled off, and then the residue was purified by silica gel column chromatography (heptane/toluene=2/1 in a volume ratio), and further the resulting mixture was recrystallized from methanol to obtain 2.17 g of compound (1-2-9).

$^1$H-NMR (CDCl$_3$; δ ppm): 7.04 (t, 1H), 6.64 (d, 1H), 4.05 (q, 2H), 3.96 (t, 2H), 1.77 (q, 2H), 1.49 (sex, 2H), 1.42 (t, 3H), 0.96 (t, 3H). Transition temperature: C 9.2 I. T$_{NI}$=−137.4° C., Δ∈=−6.58, Δn=−0.026.

Synthesis Example 8

Compound (1-4-1)

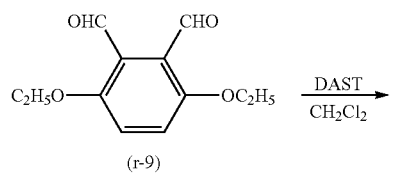

(r-9)

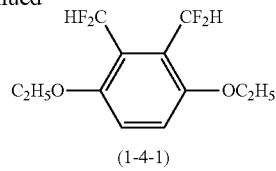

(1-4-1)

Compound (r-9) (5.00 g, 22.5 mmol) was dissolved in dichloromethane (20 mL), and diethylaminosulfas trifluoride (DAST) (6.2 mL; 7.6 g) was added thereto under ice-cooling, the resulting mixture was stirred at room temperature overnight. The reaction solution was poured into a saturated sodium carbonate aqueous solution, and subjected to extraction with dichloromethane, the oil layer was washed with a saturated sodium carbonate aqueous solution, and dried over anhydrous sodium sulfate. The solvent was distilled off, and then the residue was purified by silica gel column chromatography (heptane), and further the resulting mixture was recrystallized from methanol to obtain compound (1-4-1).

$^1$H-NMR (CDCl$_3$; δ ppm): 7.02 (s, 2H), 6.44 (t, 2H), 4.07 (q, 4H), 1.41 (t, 6H). Δ∈=−8.55.

Comparative Example 1

For comparison, compound (Ex-1) disclosed in Example 1 of WO 2011-098224 A was selected and synthesized.

$^1$H-NMR (CDCl$_3$; δ ppm): 6.62 (dd, 2H), 3.98 (t, 4H), 1.77 (quin, 4H), 1.49 (sex, 4H), 0.97 (t, 6H). Transition temperature: C −8.2 I. T$_{NI}$=−124.1° C., Δ∈=−5.88, Δn=−0.014.

Physical properties of comparative compound (Ex-1) and compound (1-1-3), each having the identical structure except for substituents in 2-position and 3-position on the benzene ring, were measured under the same conditions as described in the section "Measuring methods." Table 1 below summarizes the results. Two compounds had a melting point, and exhibited no nematic phase. The dielectric anisotropy of compound (1-1-3) was about 1.7 times the dielectric anisotropy of comparative compound (Ex-1), and the maximum temperature thereof was found to be higher by 23° C. in comparison with comparative compound (Ex-1). Accordingly, compound (1-1-3) can be concluded to be more useful from viewpoints of the maximum temperature and the dielectric anisotropy in comparison with comparative compound (Ex-1).

TABLE 1

| Comparison of physical properties | | |
|---|---|---|
| | Compound (1-1-3) in Synthesis Example 2 | Compound (Ex-1) in Comparative Example 1 |
| Structural formula | F$_3$C─⟨CF$_3$⟩ C$_4$H$_9$O─⟨⟩─OC$_4$H$_9$ | F─⟨F⟩ C$_4$H$_9$O─⟨⟩─OC$_4$H$_9$ |
| Transition temperature | C 17.7 I | C −8.2 I |
| Maximum temperature (TNI) | −101.4° C. | −124.1° C. |
| Dielectric anisotropy (Δε) | −10.1 | −5.9 |
| Optical anisotropy (Δn) | −0.003 | −0.014 |

Notes) The optical anisotropy had negative, which was caused by the extrapolation method.

Compounds described below can be prepared with reference to the methods described in Synthetic Example 1 or the like, and the section of "2. Synthesis of compound (1)."
(1-1-1)
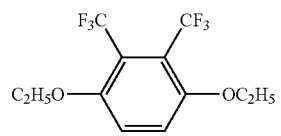
C₁ 49.9 C₂ 68.8 I (° C.)
$T_{NI}$: -116.1° C. Δε: -9.11 Δn: -0.017
(1-1-2)
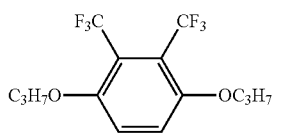
(1-1-3)
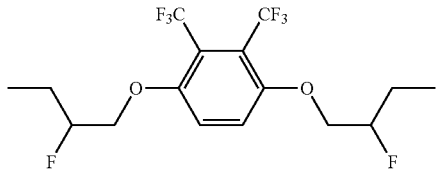
C 17.7 I (° C.)
$T_{NI}$: -101.4° C. Δε: -10.1 Δn: -0.003
(1-1-4)
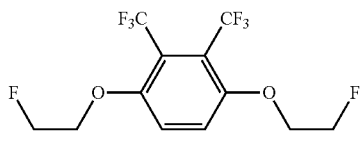
(1-1-5)
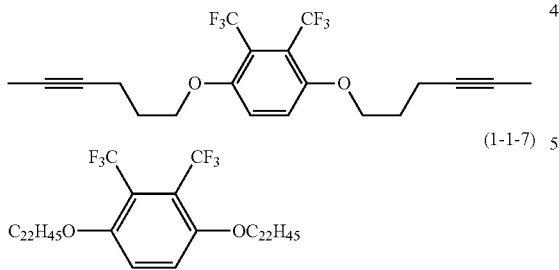
(1-1-6)
(1-1-7)
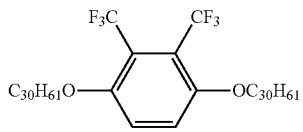
(1-1-8)
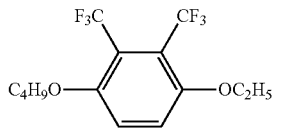
(1-1-9)
-continued
(1-1-10)
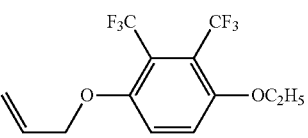
(1-1-11)
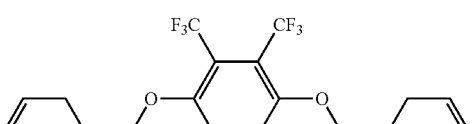
(1-1-12)
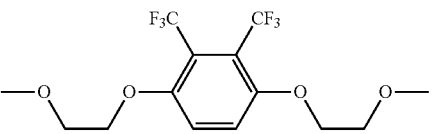
(1-1-13)
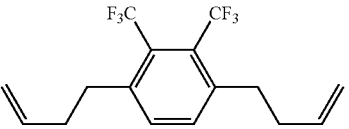
(1-1-14)
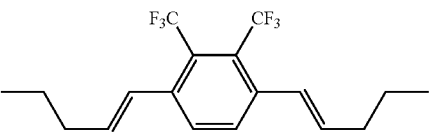
C 17.81 I (° C.)
$T_{NI}$: -116.4° C. Δε: -4.37 Δn: 0.014
(1-1-15)
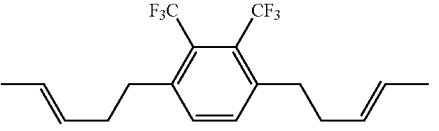
(1-1-16)
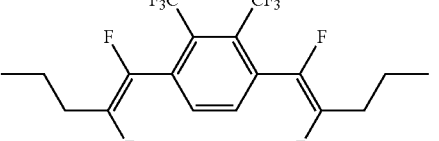
(1-1-17)
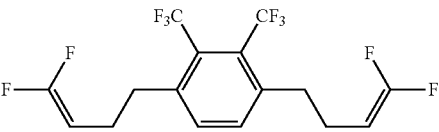
(1-1-18)
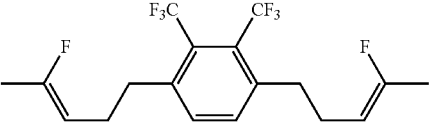
(1-1-19)
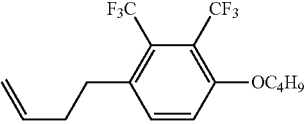

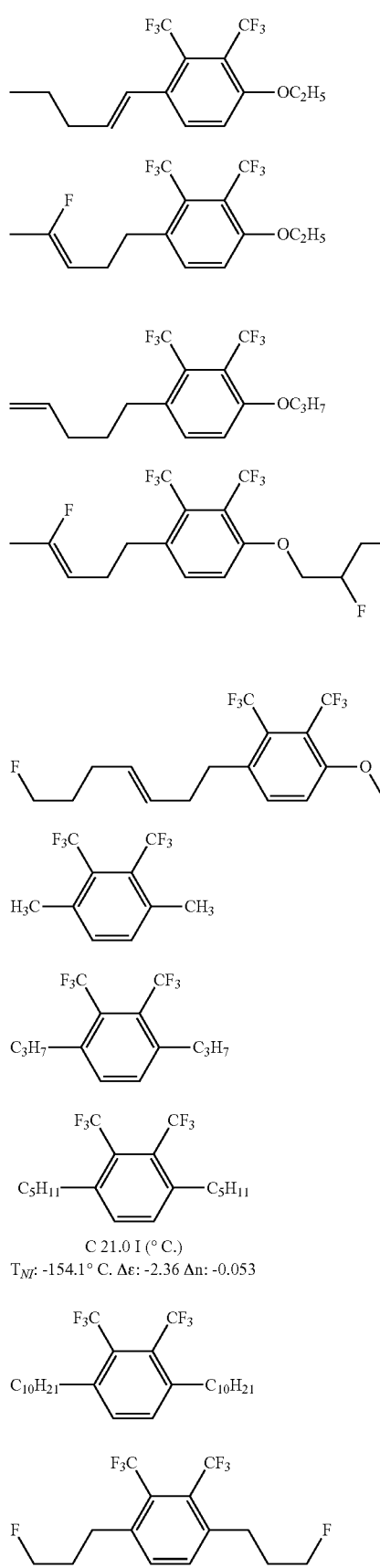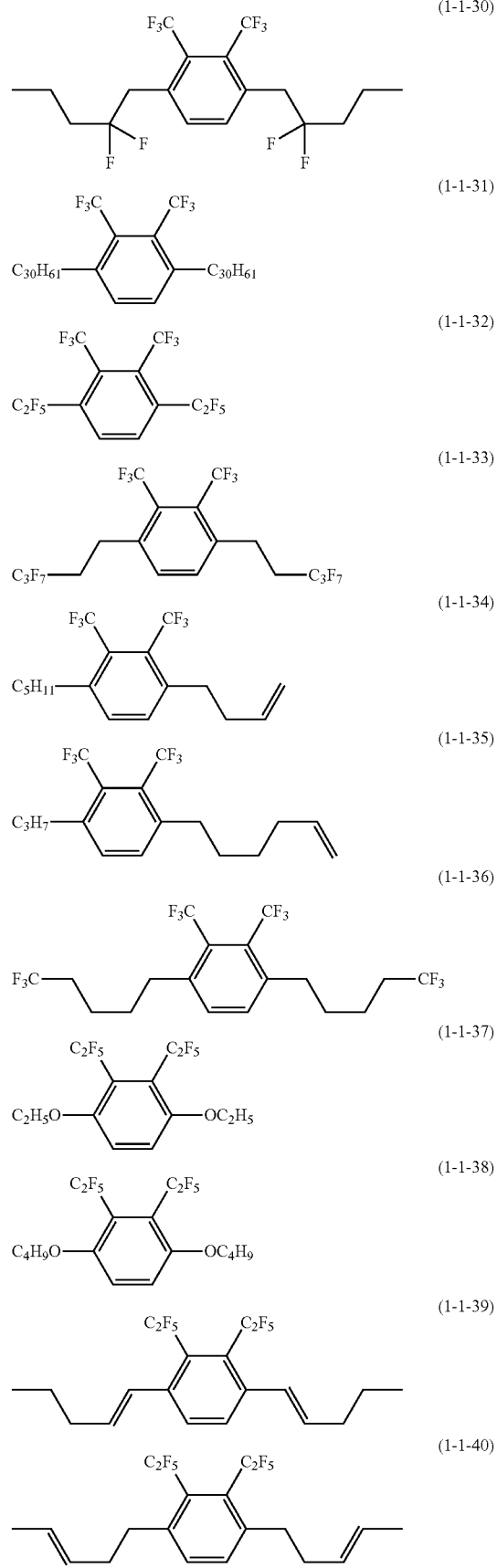

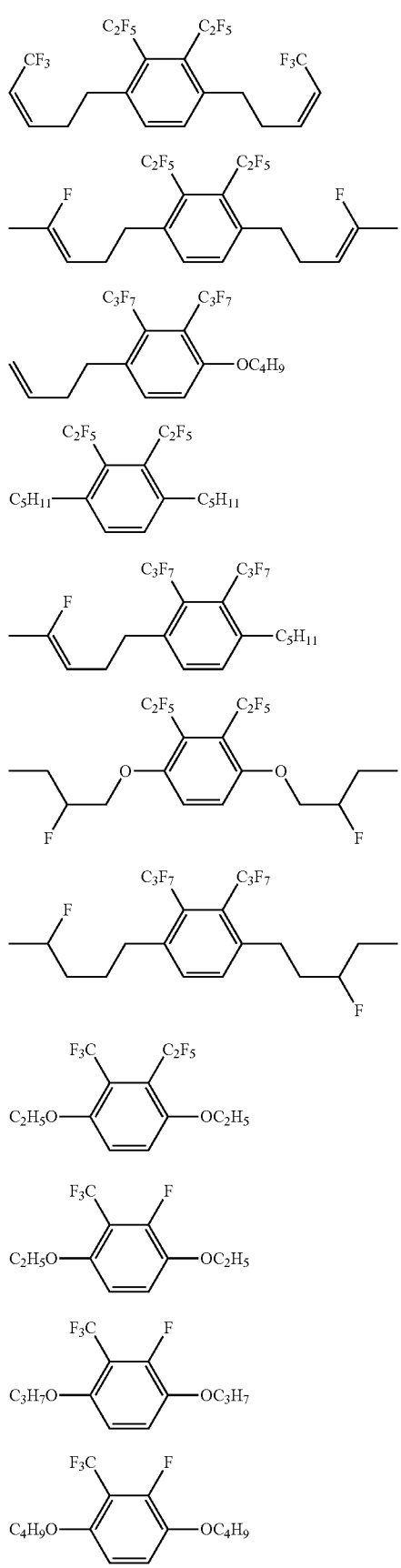
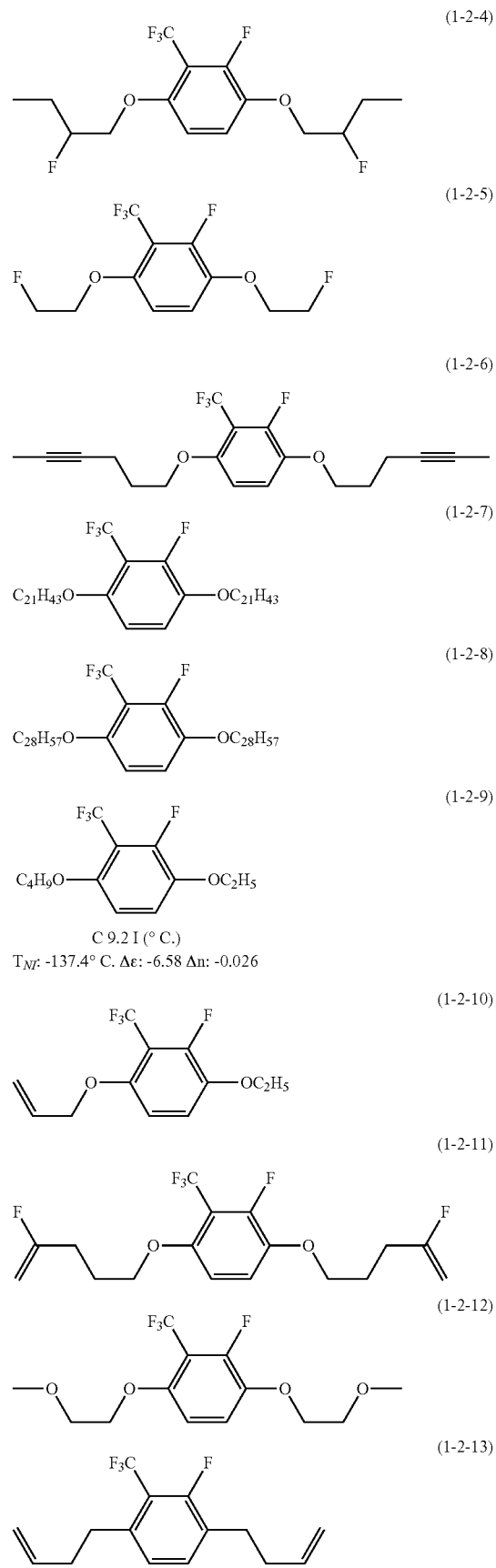
C 9.2 I (° C.)
T$_{NI}$: -137.4° C. Δε: -6.58 Δn: -0.026

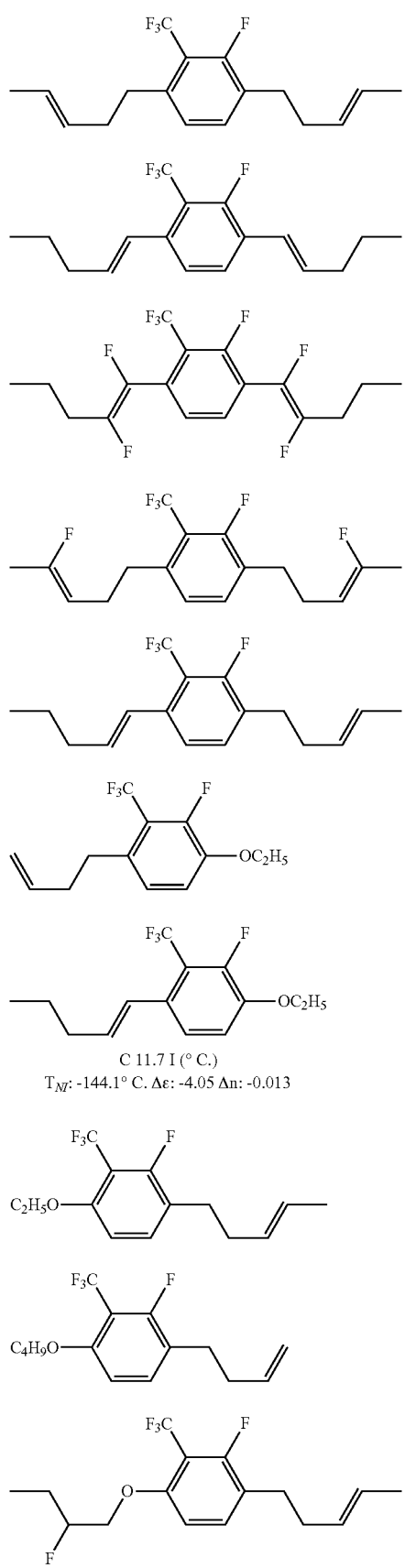
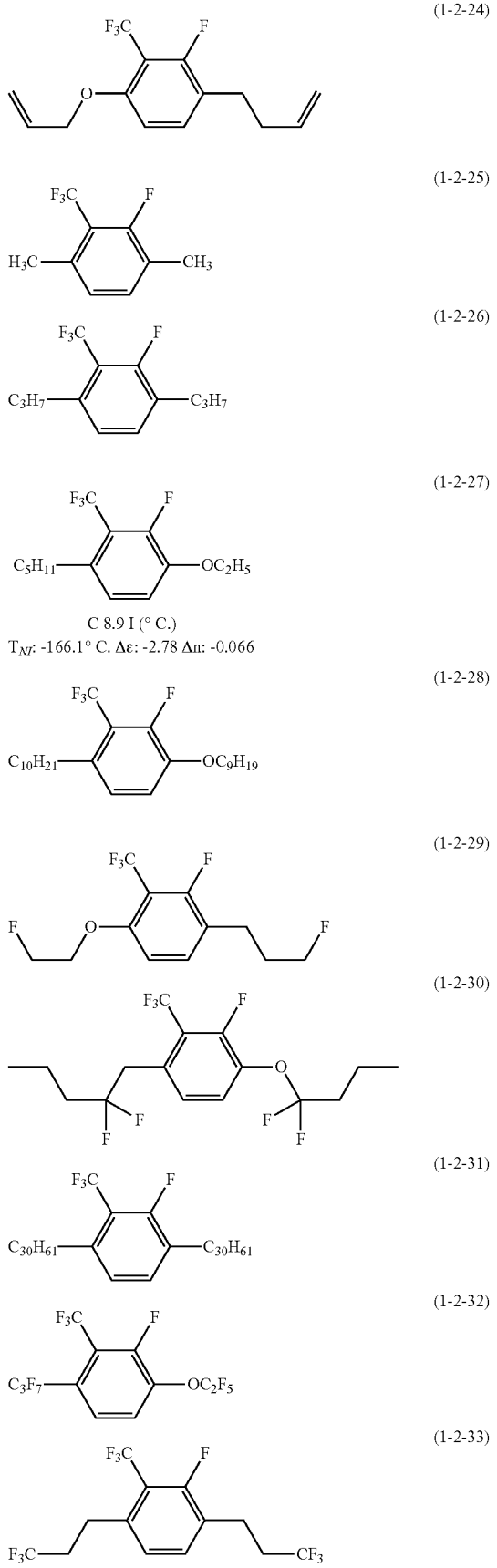

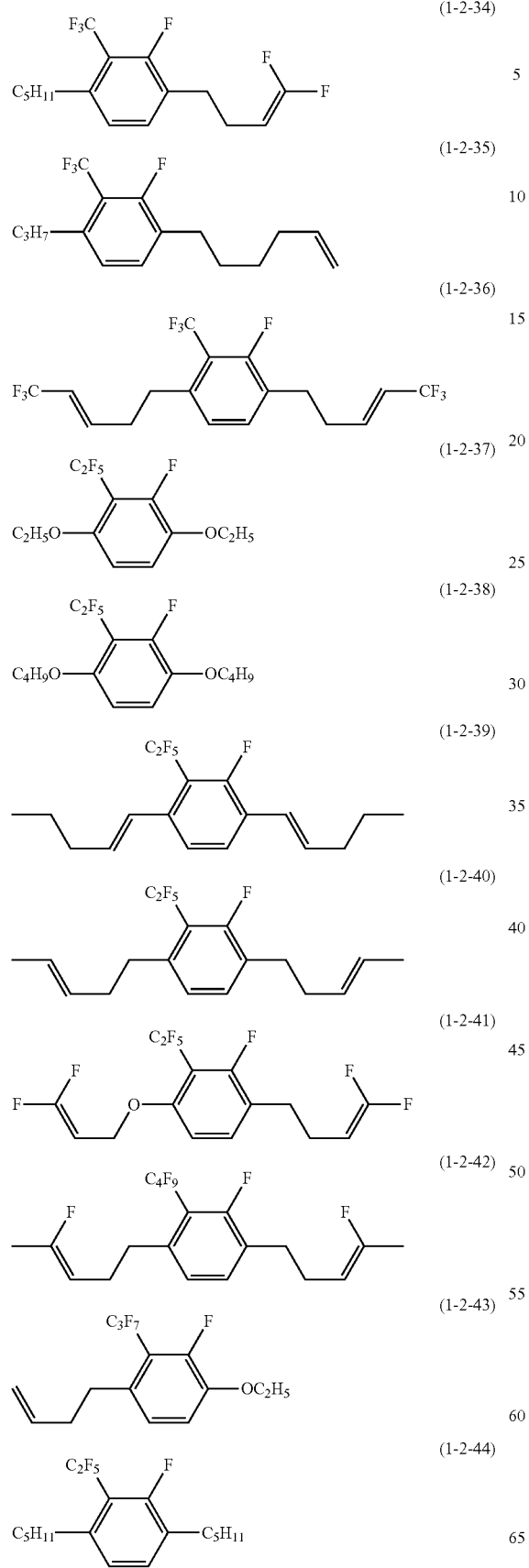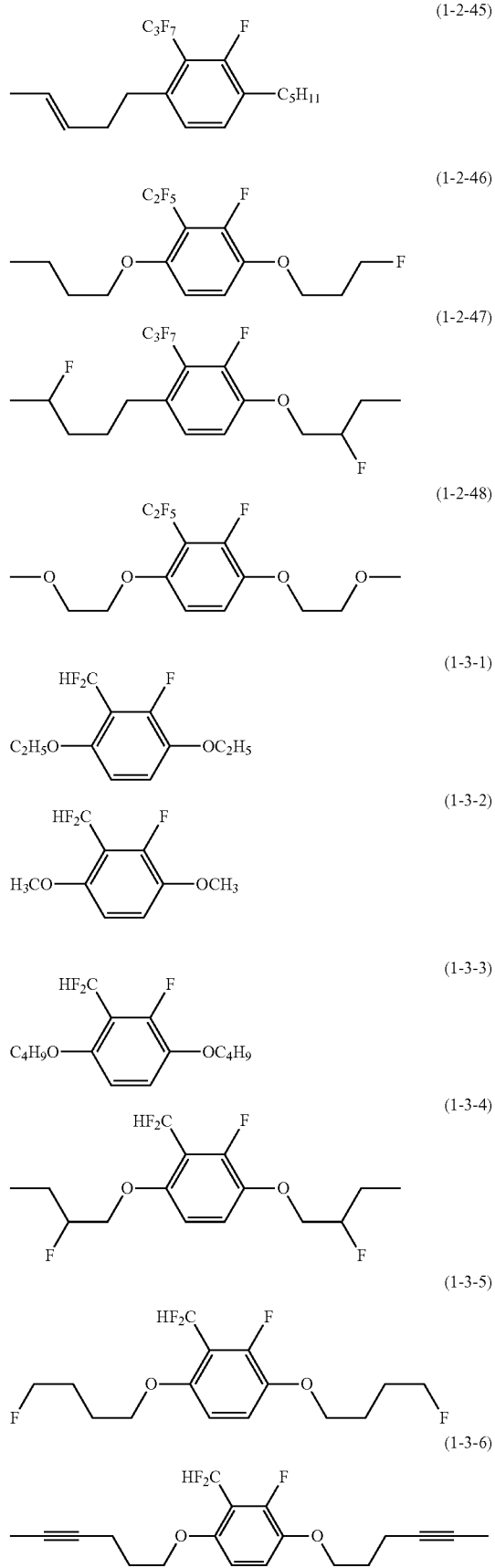

(1-3-7) 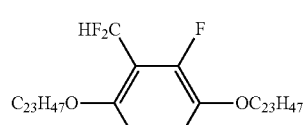
(1-3-8) 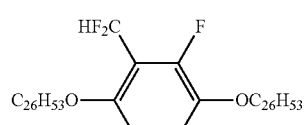
(1-3-9) 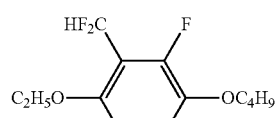
(1-3-10) 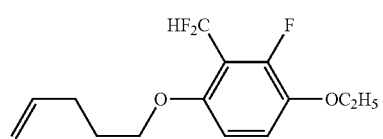
(1-3-11) 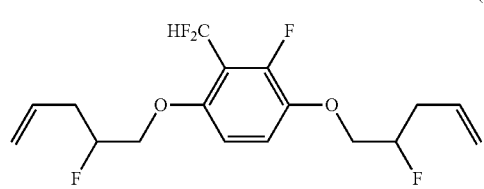
(1-3-12) 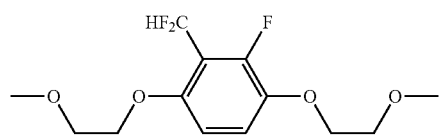
(1-3-13) 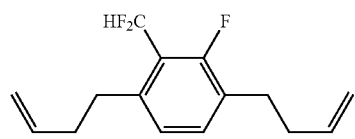
(1-3-14) 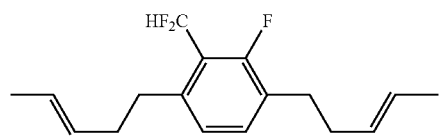
(1-3-15) 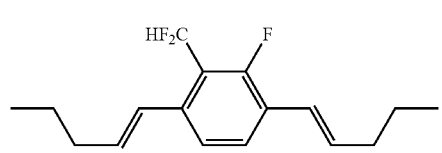
(1-3-16) 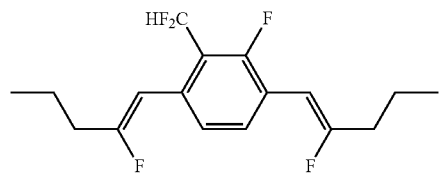
(1-3-17) 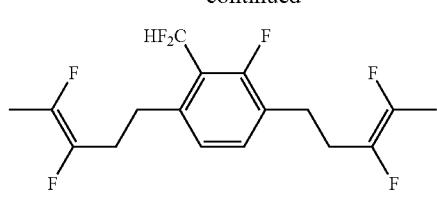
(1-3-18) 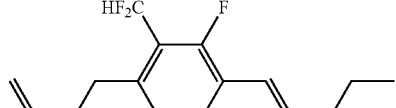
(1-3-19) 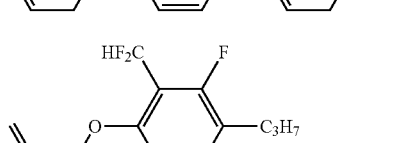
(1-3-20) 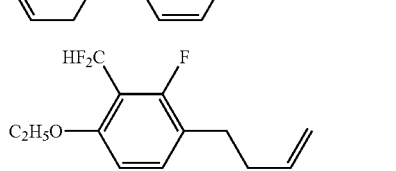
(1-3-21) 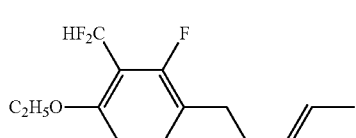
(1-3-22) 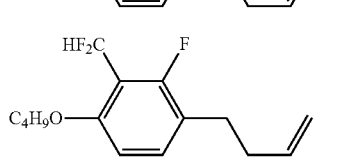
(1-3-23) 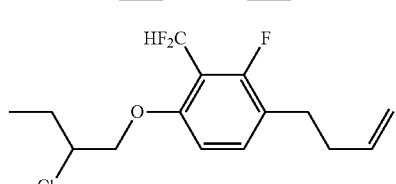
(1-3-24) 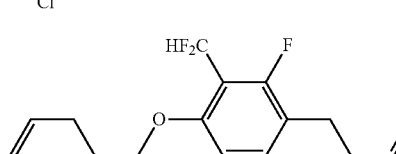
(1-3-25) 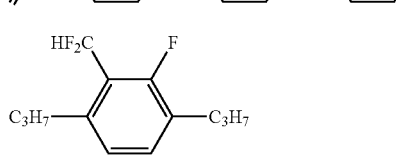
(1-3-26) 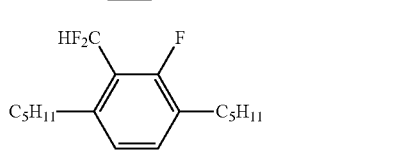
(1-3-27) 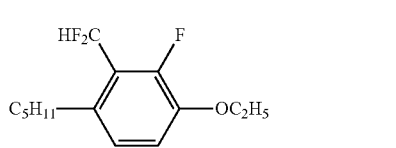

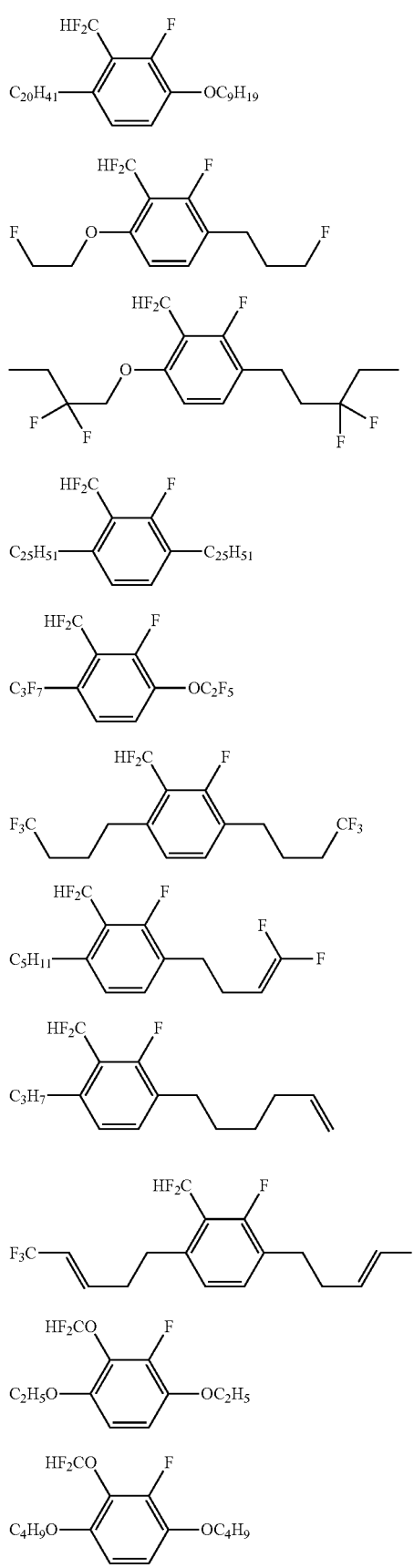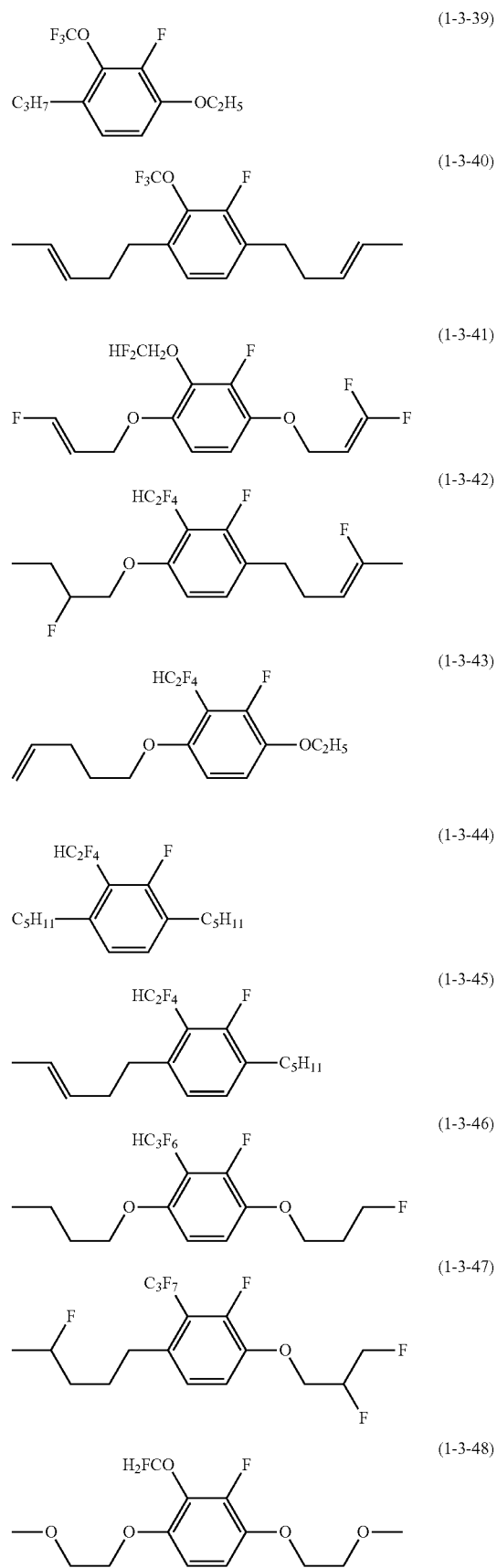

(1-4-1)
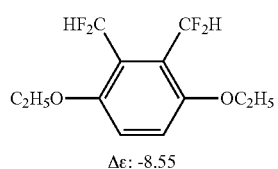
Δε: -8.55
(1-4-2)
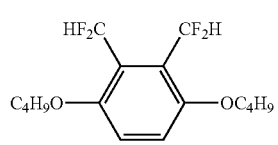
(1-4-3)
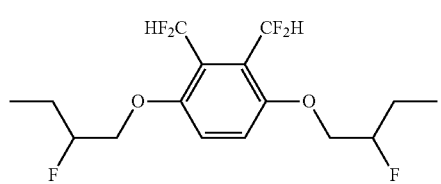
(1-4-4)
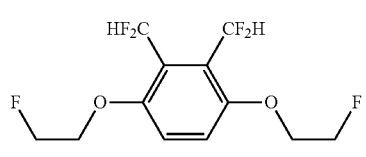
(1-4-5)
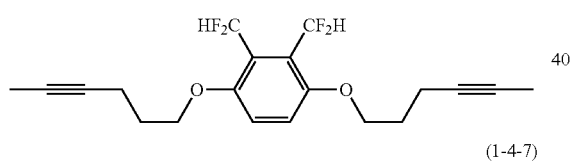
(1-4-6)
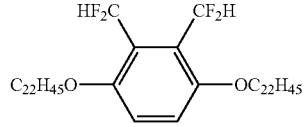
(1-4-7)
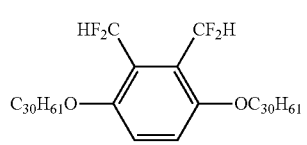
(1-4-8)
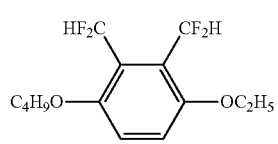
(1-4-9)
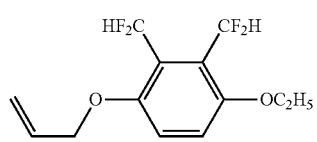
(1-4-10)
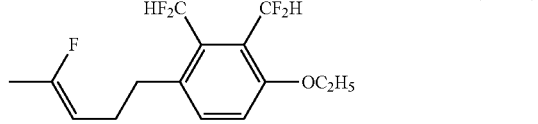
(1-4-11)
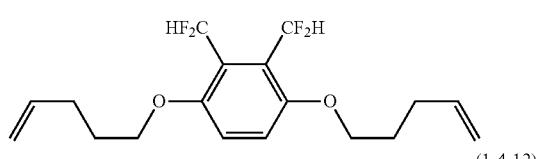
(1-4-12)
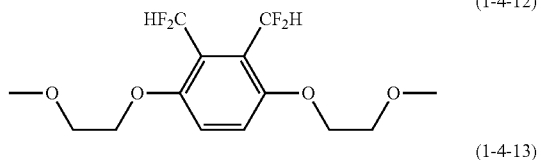
(1-4-13)
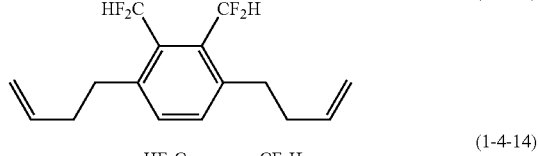
(1-4-14)
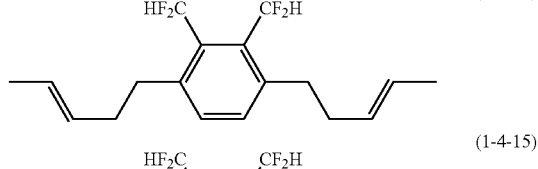
(1-4-15)
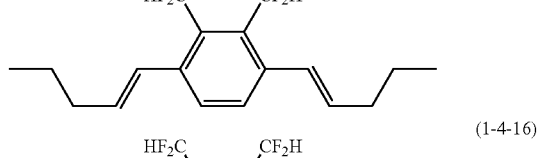
(1-4-16)
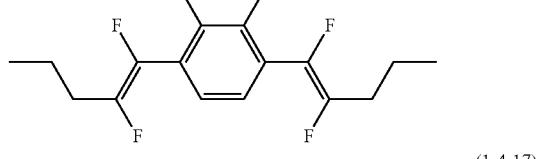
(1-4-17)
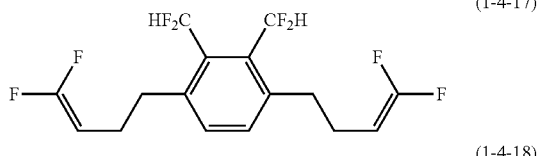
(1-4-18)
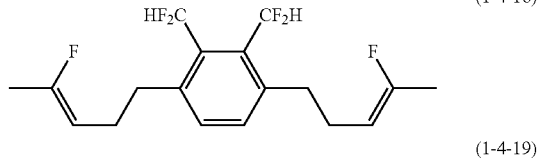
(1-4-19)
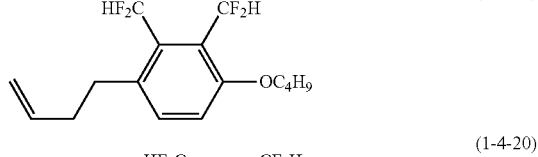
(1-4-20)
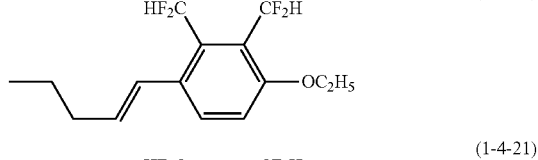
(1-4-21)

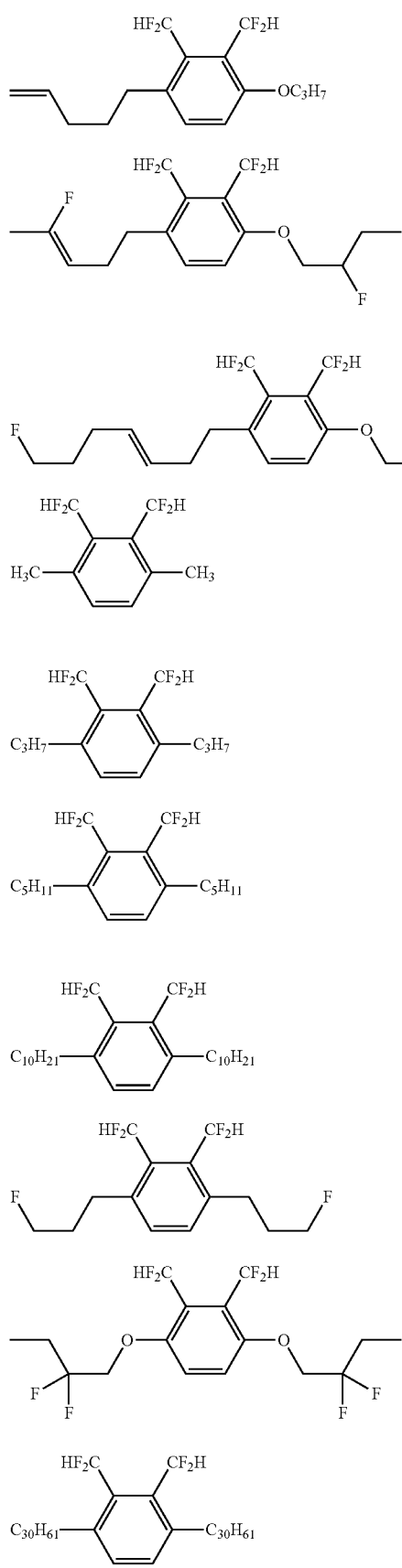
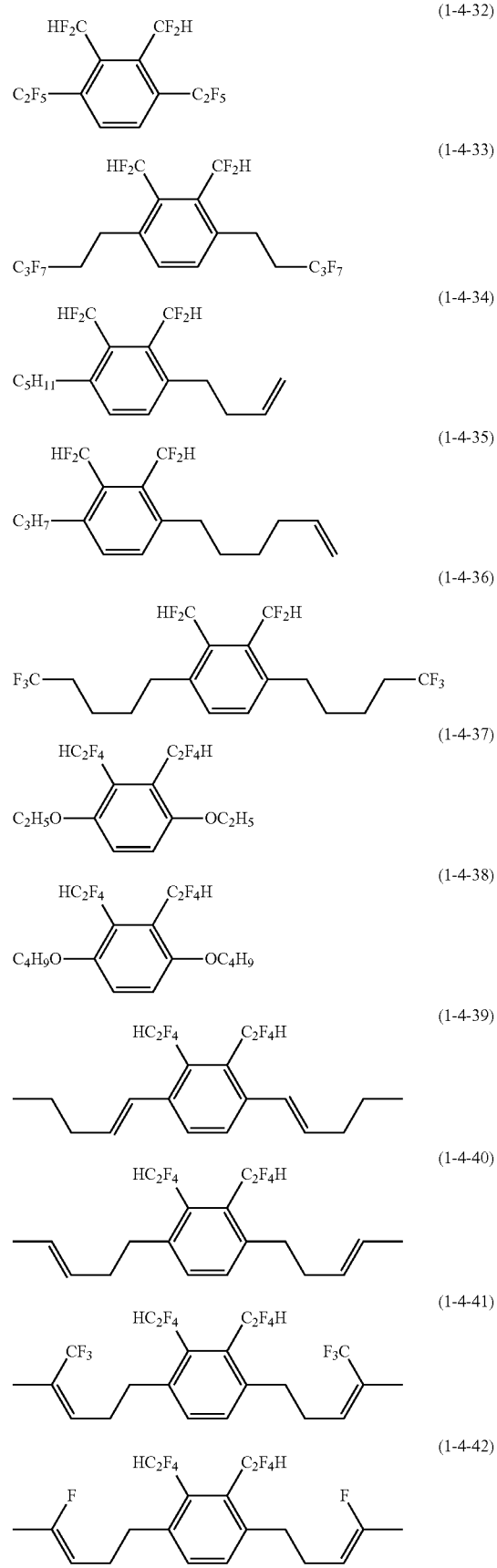

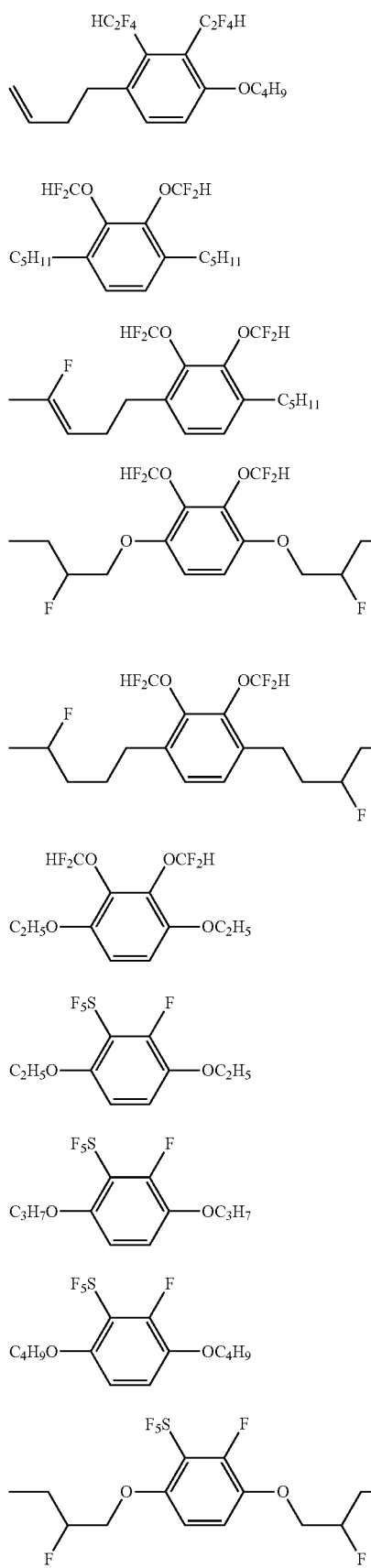
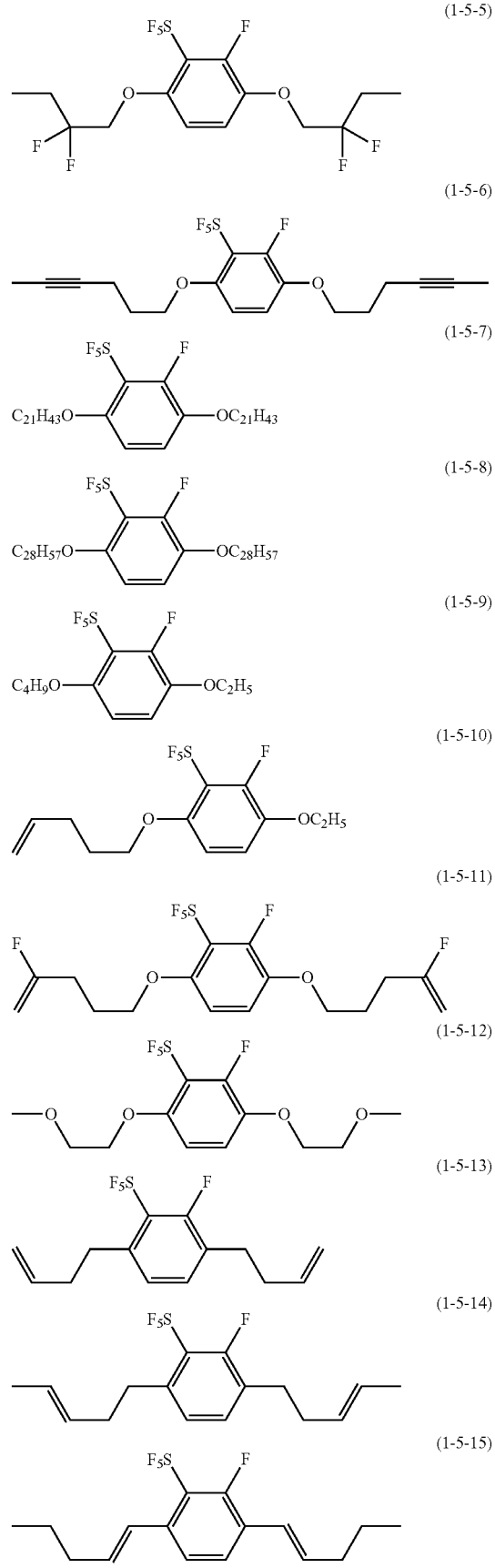

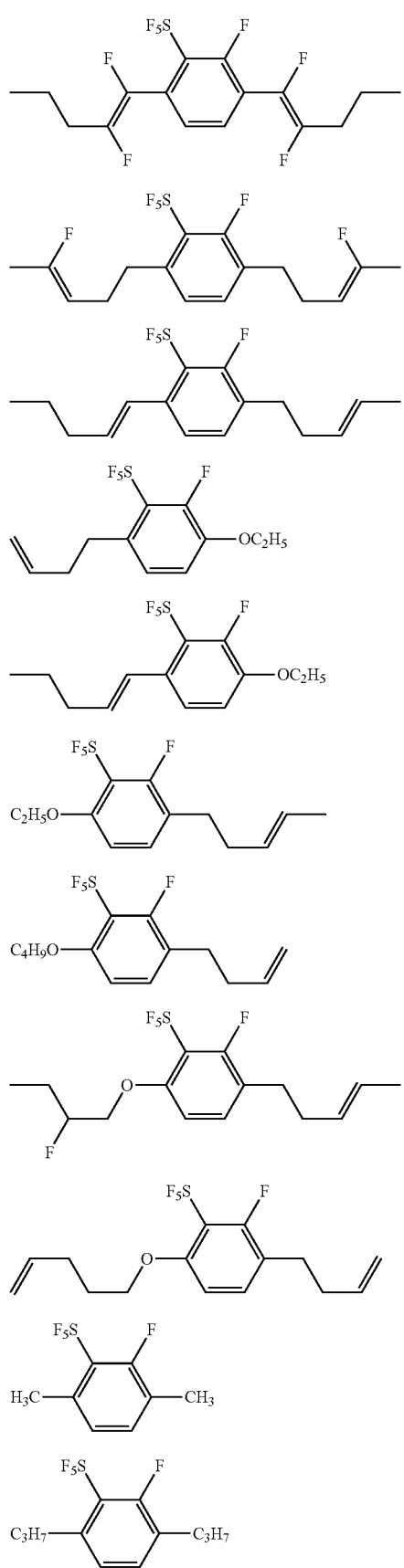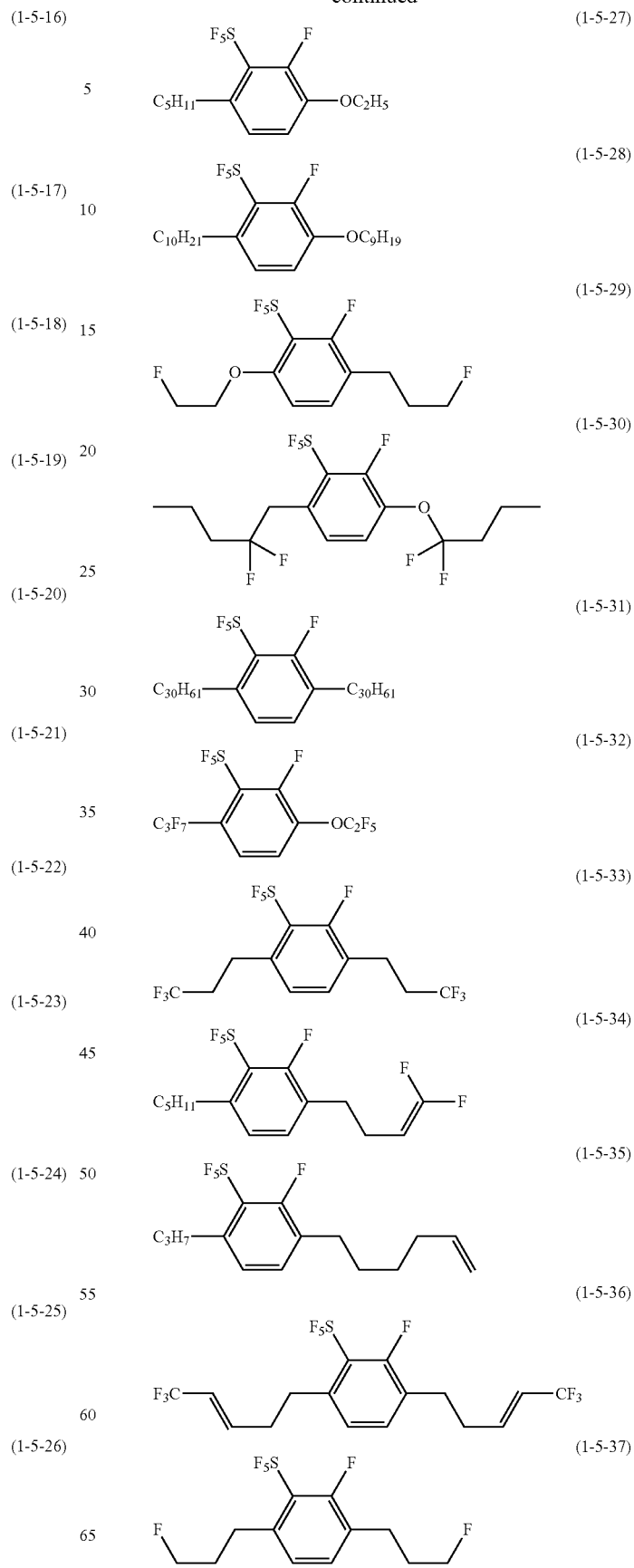

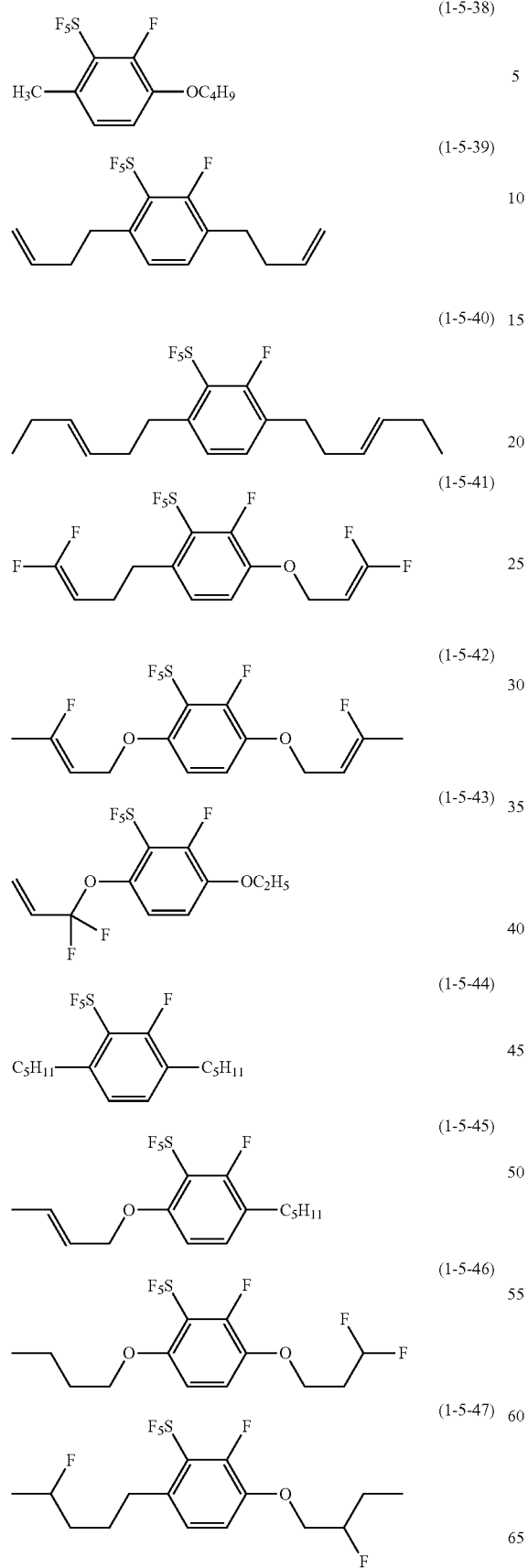
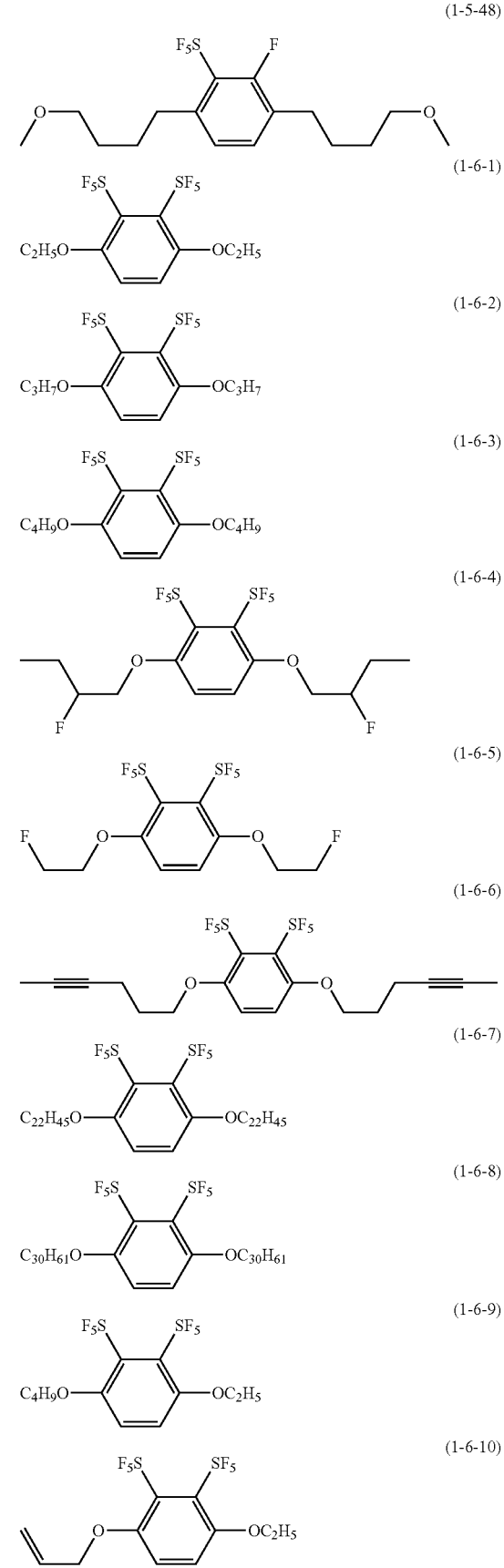

-continued
(1-6-11) 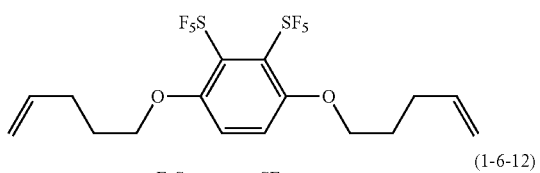
(1-6-12) 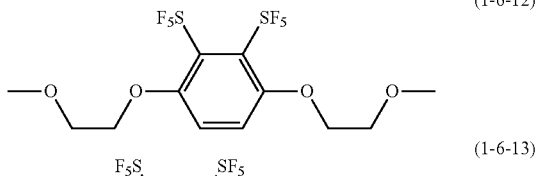
(1-6-13) 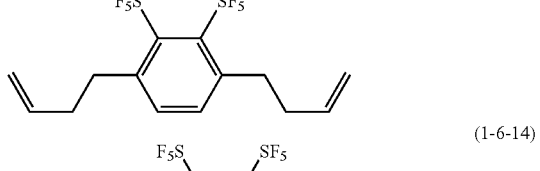
(1-6-14) 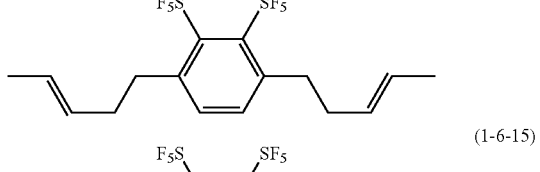
(1-6-15) 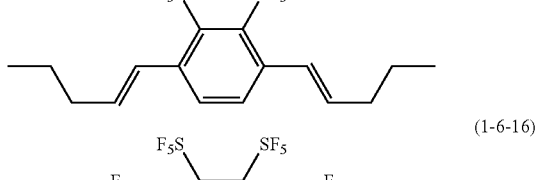
(1-6-16) 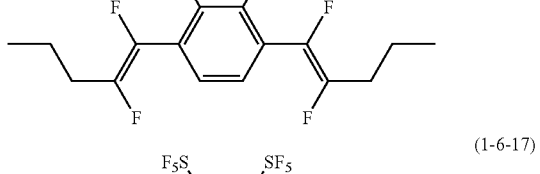
(1-6-17) 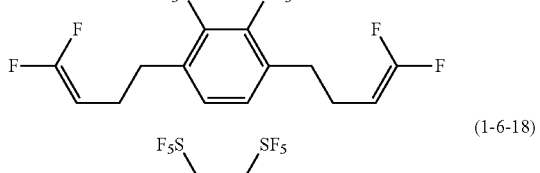
(1-6-18) 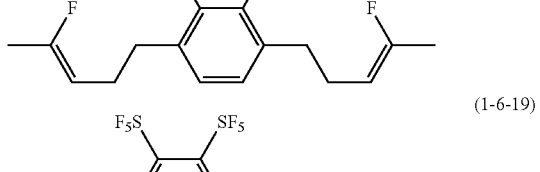
(1-6-19) 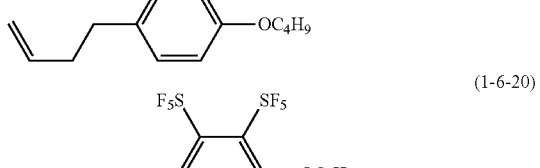
(1-6-20) 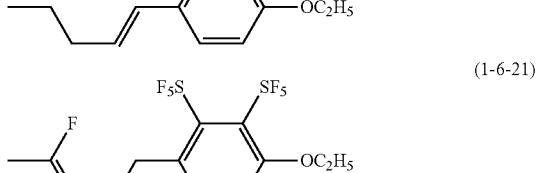
(1-6-21) 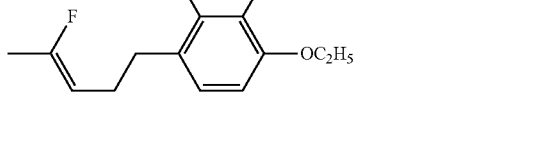
-continued
(1-6-22) 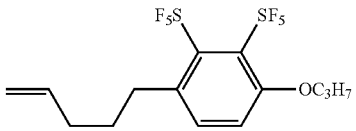
(1-6-23) 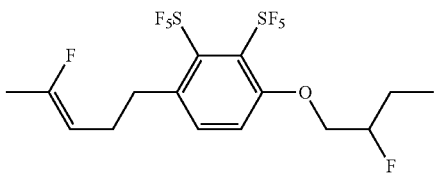
(1-6-24) 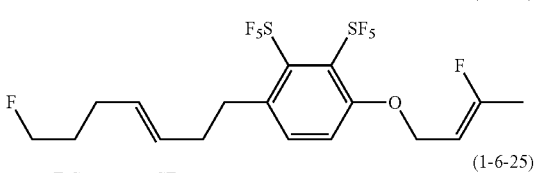
(1-6-25) 
(1-6-26) 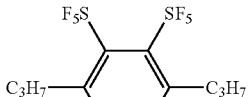
(1-6-27) 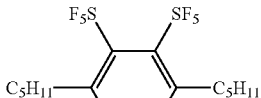
(1-6-28) 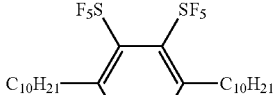
(1-6-29) 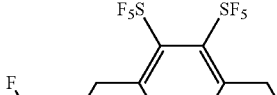
(1-6-30) 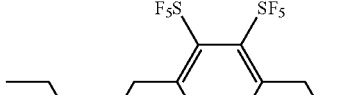
(1-6-31) 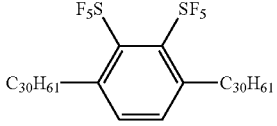

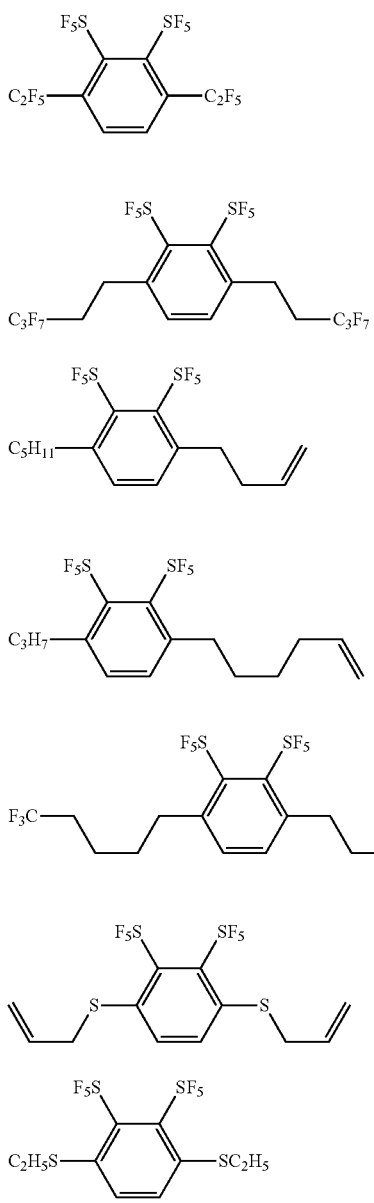
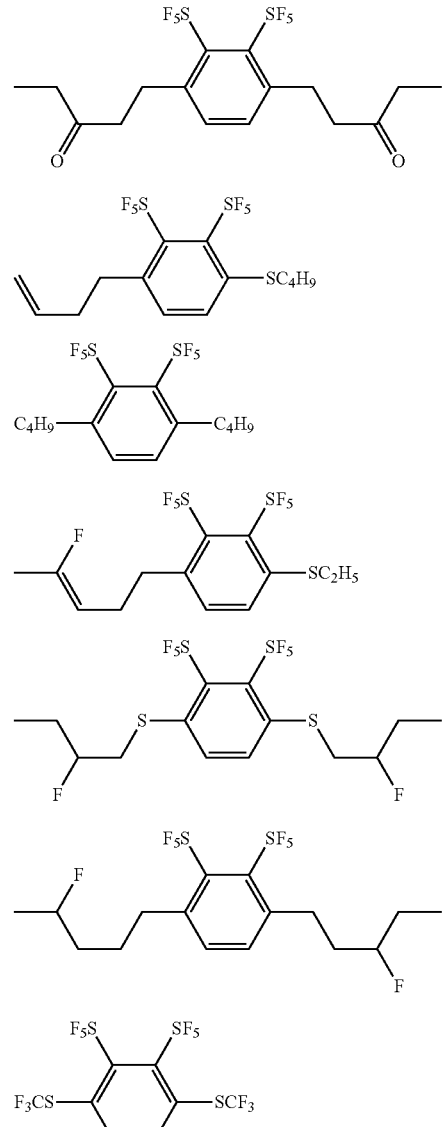

2. Example of Liquid Crystal Composition

The invention includes a mixture of a composition in Use example 1 and a composition in Use example 2. The invention also includes a mixture of at least two compositions in Use examples. The compounds in Use examples were represented using symbols according to definitions in Table 2 below. In Table 2, a configuration of 1,4-cyclohexylene is trans. In the Use examples, a parenthesized number next to a symbolized compound represent a chemical formula to which the compound belongs. A symbol (-) means any other liquid crystal compound different from compounds (2) to (15). A proportion (percentage) of the liquid crystal compound is expressed in terms of weight percent (% by weight) based on the weight of the liquid crystal composition. Values of physical properties of the composition are summarized in a last part. The physical properties were measured in accordance with the methods described above, and measured values are directly described (without extrapolation).

TABLE 2

Method for Description of Compounds using Symbols
R—(A)₁—Z₁— ... —Zₙ—(Aₙ)—R'

1) Left-terminal Group R—

| Group | Symbol |
|---|---|
| $C_nH_{2n+1}$— | n- |
| $C_nH_{2n+1}O$— | nO— |
| $C_mH_{2m+1}OC_nH_{2n}$— | mOn- |
| $CH_2=CH$— | V— |
| $C_nH_{2n+1}$—CH=CH— | nV— |
| $CH_2=CH$—$C_nH_{2n}$— | Vn- |
| $C_mH_{2m+1}$—CH=CH—$C_nH_{2n}$— | mVn- |
| $CF_2=CH$— | VFF— |
| $CF_2=CH$—$C_nH_{2n}$— | VFFn- |

2) Right-terminal Group —R'

| Group | Symbol |
|---|---|
| —$C_nH_{2n+1}$ | -n |
| —$OC_nH_{2n+1}$ | —On |
| —CH=$CH_2$ | —V |
| —CH=CH—$C_nH_{2n+1}$ | —Vn |
| —$C_nH_{2n}$—CH=$CH_2$ | -nV |
| —$C_mH_{2m}$—CH=CH—$C_nH_{2n+1}$ | -mVn |
| —CH=$CF_2$ | —VFF |
| —F | —F |
| —Cl | —CL |
| —$OCF_3$ | —OCF3 |
| —$OCF_2H$ | —OCF2H |
| —$CF_3$ | —CF3 |
| —C≡N | —C |

3) Bonding Group —Zn—

| Group | Symbol |
|---|---|
| —$C_nH_{2n}$— | n |
| —COO— | E |
| —CH=CH— | V |
| —$CH_2O$— | 1O |
| —$OCH_2$— | O1 |
| —$CF_2O$— | X |
| —C≡C— | T |

4) Ring Structure —An—

| Structure | Symbol |
|---|---|
| 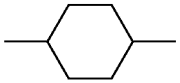 | H |
|  | B |
| 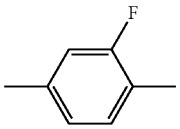 | B(F) |
| 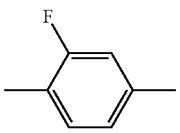 | B(2F) |
| 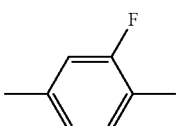 | B(F,F) |
| 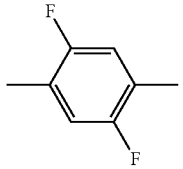 | B(2F,5F) |
| 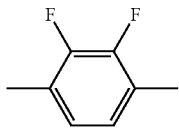 | B(2F,3F) |
| 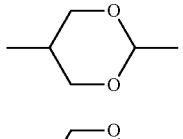 | G |
| 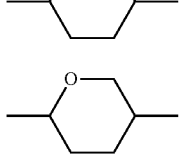 | dh |
| 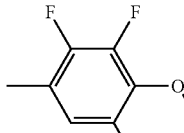 | Dh |
| 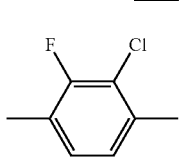 | Cro |
| 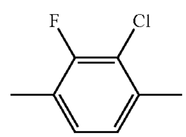 | B(2F,3CL) |
| 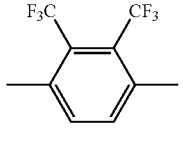 | B(2CF3,3CF3) |
| 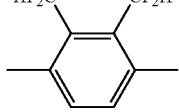 | B(2CF2H,3CF2H) |
| 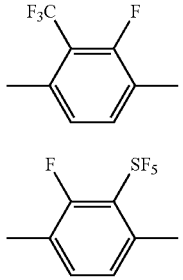 | B(2CF3,3F) |

TABLE 2-continued

Method for Description of Compounds using Symbols
R—(A)₁—Z₁— . . . —Zₙ—(Aₙ)—R'

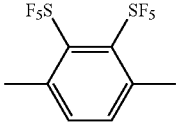

B(2SF5,3SF5)

5) Examples of Description

Example 1  5-B(2CF3,3CF3)-5

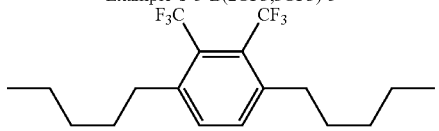

Example 2  3-HB-O2

Use Example 1

| | | |
|---|---|---|
| 4O-B (2CF3, 3CF3)-O4 | (1-1-3) | 3% |
| 3-GB (F) B (F, F) XB (F, F)-F | (14-57) | 5% |
| 3-BB (F) B (F, F) XB (F, F)-F | (14-47) | 3% |
| 4-BB (F) B (F, F) XB (F, F)-F | (14-47) | 7% |
| 5-BB (F) B (F, F) XB (F, F)-F | (14-47) | 3% |
| 3-HH-V | (2-1) | 40% |
| 3-HH-V1 | (2-1) | 7% |
| 3-HHEH-5 | (3-13) | 3% |
| 3-HHB-1 | (3-1) | 4% |
| V-HHB-1 | (3-1) | 5% |
| V2-BB (F) B-1 | (3-6) | 5% |
| 1V2-BB-F | (12-1) | 3% |
| 3-BB (F, F) XB (F, F)-F | (13-97) | 5% |
| 3-GB (F, F) XB (F, F)-F | (13-113) | 4% |
| 3-HHBB (F, F)-F | (14-6) | 3% |

NI = 77.9° C.;
η = 14.0 mPa · s;
Δn = 0.101;
Δε = 6.8.

Use Example 2

| | | |
|---|---|---|
| 2O-B (2CF3, 3CF3)-O2 | (1-1-1) | 3% |
| 5-HB (F) B (F, F) XB (F, F)-F | (14-41) | 5% |
| 3-BB (F) B (F, F) XB (F, F)-F | (14-47) | 3% |
| 4-BB (F) B (F, F) XB (F, F)-F | 14-47) | 6% |
| 5-BB (F) B (F, F) XB (F, F)-F | (14-47) | 3% |
| 3-HH-V | (2-1) | 40% |
| 3-HH-V1 | (2-1) | 7% |
| 3-HHEH-5 | (3-13) | 3% |
| 3-HHB-1 | (3-1) | 4% |
| V-HHB-1 | (3-1) | 5% |
| V2-BB (F) B-1 | (3-6) | 5% |
| 1V2-BB-F | (12-1) | 3% |
| 3-BB (F, F) XB (F, F)-F | (13-97) | 10% |
| 3-HHBB (F, F)-F | (14-6) | 3% |

NI = 77.1° C.;
η = 12.7 mPa · s;
Δn = 0.101;
Δε = 5.7.

Use Example 3

| | | |
|---|---|---|
| 3V-B (2CF3, 3CF3)-V3 | (1-1-14) | 5% |
| 1V2-BEB (F, F)-C | (15-15) | 5% |
| 3-HB-C | (15-1) | 17% |
| 2-BTB-1 | (2-10) | 10% |
| 5-HH-VFF | (2-1) | 29% |
| 3-HHB-1 | (3-1) | 4% |
| VFF-HHB-1 | (3-1) | 8% |
| VFF2-HHB-1 | (3-1) | 10% |
| 3-H2BTB-2 | (3-17) | 5% |
| 3-H2BTB-3 | (3-17) | 4% |
| 3-H2BTB-4 | (3-17) | 3% |

NI = 71.5° C.;
Δn = 0.124;
Δε = 5.6.

Use Example 4

| | | |
|---|---|---|
| 5-B (2CF3, 3CF3)-5 | (1-1-27) | 4% |
| 2-HH-3 | (2-1) | 5% |
| 3-HH-V1 | (2-1) | 10% |
| 1V2-HH-1 | (2-1) | 8% |
| 1V2-HH-3 | (2-1) | 7% |
| 3-BB (2F, 3F)-O2 | (5-3) | 7% |
| 5-BB (2F, 3F)-O2 | (5-3) | 3% |
| 3-H1OB (2F, 3F)-O2 | (5-5) | 6% |
| 2-HH1OB (2F, 3F)-O2 | (6-5) | 8% |
| 3-HH1OB (2F, 3F)-O2 | (6-5) | 19% |
| 3-HDhB (2F, 3F)-O2 | (-) | 7% |
| 3-HHB-1 | (3-1) | 3% |
| 3-HHB-3 | (3-1) | 2% |
| 2-BB (2F, 3F) B-3 | (5-3) | 11% |

NI = 78.3° C.;
η = 22.5 mPa · s;
Δn = 0.102;
Δε = −4.3.

Use Example 5

| | | |
|---|---|---|
| 4O-B (2CF3, 3F)-O2 | (1-2-9) | 3% |
| 1-BB-3 | (2-6) | 9% |
| 3-HH-V | (2-1) | 29% |
| 3-BB (2F, 3F)-O2 | (5-3) | 11% |
| 2-HH1OB (2F, 3F)-O2 | (6-5) | 20% |
| 3-HH1OB (2F, 3F)-O2 | (6-5) | 14% |
| 3-HHB-1 | (3-1) | 8% |
| 5-B (F) BB-2 | (3-8) | 6% |

NI = 70.5 ° C.;
η = 15.4 mPa · s;
Δn = 0.100;
Δε = −3.1.

Use Example 6

| | | |
|---|---|---|
| 3V-B (2CF3, 3F)-O2 | (1-2-20) | 4% |
| 2-HH-3 | (2-1) | 16% |
| 7-HB-1 | (2-5) | 9% |
| 5-HB-O2 | (2-5) | 8% |
| 3-HB (2F, 3F)-O2 | (5-1) | 15% |
| 5-HB (2F, 3F)-O2 | (5-1) | 15% |
| 3-HHB (2F, 3CL)-O2 | (6-12) | 3% |
| 4-HHB (2F, 3CL)-O2 | (6-12) | 3% |
| 5-HHB (2F, 3CL)-O2 | (6-12) | 2% |
| 3-HH1OCro (7F, 8F)-5 | (9-6) | 5% |

| | | |
|---|---|---|
| 5-HBB (F) B-2 | (4-5) | 10% |
| 5-HBB (F) B-3 | (4-5) | 10% |

NI = 70.2° C.;
η = 23.8 mPa · s;
Δn = 0.101;
Δε = −2.5.

Use Example 7

| | | |
|---|---|---|
| 5-B (2CF3, 3F)-O2 | (1-2-27) | 3% |
| 2-HH-3 | (2-1) | 20% |
| 3-HH-4 | (2-1) | 9% |
| 1-BB-3 | (2-8) | 8% |
| 3-HB-O2 | (2-5) | 2% |
| 3-BB (2F, 3F)-O2 | (5-3) | 8% |
| 5-BB (2F, 3F)-O2 | (5-3) | 5% |
| 2-HH1OB (2F, 3F)-O2 | (6-5) | 13% |
| 3-HH1OB (2F, 3F)-O2 | (6-5) | 21% |
| 3-HHB-1 | (3-1) | 5% |
| 3-HHB-O1 | (3-1) | 3% |
| 5-B (F) BB-2 | (3-8) | 3% |

NI = 70.3 ° C.;
η = 16.2 mPa · s;
Δn = 0.093;
Δε = −3.2.

Use Example 8

| | | |
|---|---|---|
| 2O-B (2F, 3SF5)-O2 | (1-5-1) | 3% |
| 2-HH-5 | (2-1) | 3% |
| 3-HH-4 | (2-1) | 15% |
| 3-HH-5 | (2-1) | 4% |
| 3-HB-O2 | (2-5) | 12% |
| 3-H2B (2F, 3F)-O2 | (5-4) | 12% |
| 5-H2B (2F, 3F)-O2 | (5-4) | 15% |
| 3-HHB (2F, 3CL)-O2 | (6-12) | 5% |
| 2-HBB (2F, 3F)-O2 | (6-7) | 3% |
| 3-HBB (2F, 3F)-O2 | (6-7) | 9% |
| 5-HBB (2F, 3F)-O2 | (6-7) | 9% |
| 3-HHB-1 | (3-1) | 3% |
| 3-HHB-3 | (3-1) | 4% |
| 3-HHB-O1 | (3-1) | 3% |

Use Example 9

| | | |
|---|---|---|
| 2O-B (2SF5, 3SF5)-O2 | (1-6-1) | 3% |
| 3-HB-O1 | (2-5) | 15% |
| 3-HH-4 | (2-1) | 5% |
| 3-HB (2F, 3F)-O2 | (5-1) | 12% |
| 5-HB (2F, 3F)-O2 | (5-1) | 12% |
| 2-HHB (2F, 3F)-1 | (6-1) | 11% |
| 3-HHB (2F, 3F)-1 | (6-1) | 12% |
| 3-HHB (2F, 3F)-O2 | (6-1) | 11% |
| 5-HHB (2F, 3F)-O2 | (6-1) | 13% |
| 3-HHB-1 | (3-1) | 6% |

Use Example 10

| | | |
|---|---|---|
| 5-B (2SF5,3SF5)-5 | (1-6-27) | 3% |
| 5-HB-CL | (12-2) | 3% |
| 7-HB (F)-F | (12-3) | 7% |
| 3-HH-4 | (2-1) | 9% |
| 3-HH-5 | (2-1) | 10% |
| 3-HB-O2 | (2-5) | 13% |
| 3-HHEB-F | (13-10) | 8% |
| 5-HHEB-F | (13-10) | 8% |
| 3-HHEB (F, F)-F | (13-12) | 9% |
| 4-HHEB (F, F)-F | (13-12) | 5% |
| 3-GHB (F, F)-F | (13-109) | 4% |
| 4-GHB (F, F)-F | (13-109) | 5% |
| 5-GHB (F, F)-F | (13-109) | 7% |
| 2-HHB (F, F)-F | (13-3) | 4% |
| 3-HHB (F, F)-F | (13-3) | 5% |

Use Example 11

| | | |
|---|---|---|
| 2O-B (2CF2H, 3CF2H)-O2 | (1-4-1) | 3% |
| 5-HB-CL | (12-2) | 14% |
| 7-HB (F, F)-F | (12-4) | 3% |
| 3-HH-4 | (2-1) | 10% |
| 3-HH-5 | (2-1) | 5% |
| 3-HB-O2 | (2-5) | 15% |
| 3-HHB-1 | (3-1) | 8% |
| 3-HHB-O1 | (3-1) | 5% |
| 2-HHB (F)-F | (13-2) | 7% |
| 3-HHB (F)-F | (13-2) | 7% |
| 5-HHB (F)-F | (13-2) | 7% |
| 3-HHB (F, F)-F | (13-3) | 6% |
| 3-H2HB (F, F)-F | (13-15) | 5% |
| 4-H2HB (F, F)-F | (13-15) | 5% |

Use Example 12

| | | |
|---|---|---|
| 2O-B (2CF3, 3CF3)-O2 | (1-1-1) | 2% |
| 4O-B (2CF3, 3CF3)-O4 | (1-1-3) | 2% |
| 3-HB-CL | (12-2) | 5% |
| 5-HB-CL | (12-2) | 3% |
| 3-HHB-OCF3 | (13-1) | 5% |
| 3-H2HB-OCF3 | (13-13) | 5% |
| 5-H4HB-OCF3 | (13-19) | 15% |
| V-HHB (F)-F | (13-2) | 4% |
| 3-HHB (F)-F | (13-2) | 4% |
| 5-HHB (F)-F | (13-2) | 7% |
| 3-H4HB (F, F)-CF3 | (13-21) | 8% |
| 5-H4HB (F, F)-CF3 | (13-21) | 10% |
| 5-H2HB (F, F)-F | (13-15) | 5% |
| 5-H4HB (F, F)-F | (13-21) | 7% |
| 2-H2BB (F)-F | (13-26) | 5% |
| 3-H2BB (F)-F | (13-26) | 8% |
| 3-HBEB (F, F)-F | (13-39) | 5% |

NI = 64.3 ° C.;
η = 27.1 mPa · s;
Δn = 0.092;
Δε = 8.0.

Use Example 13

| | | |
|---|---|---|
| 3V-B (2CF3, 3CF3)-V3 | (1-1-14) | 3% |
| 5-B (2CF3, 3CF3)-5 | (1-1-27) | 3% |
| 5-HB-CL | (12-2) | 10% |
| 3-HH-4 | (2-1) | 7% |
| 3-HHB-1 | (3-1) | 5% |
| 3-HHB (F, F)-F | (13-3) | 7% |
| 3-HBB (F, F)-F | (13-24) | 18% |
| 5-HBB (F, F)-F | (13-24) | 15% |

-continued

| | | |
|---|---|---|
| 3-HHEB (F, F)-F | (13-12) | 10% |
| 4-HHEB (F, F)-F | (13-12) | 3% |
| 5-HHEB (F, F)-F | (13-12) | 3% |
| 2-HBEB (F, F)-F | (13-39) | 3% |
| 3-HBEB (F, F)-F | (13-39) | 5% |
| 5-HBEB (F, F)-F | (13-39) | 3% |
| 3-HHBB (F, F)-F | (14-6) | 5% |

NI = 67.8 °C.;
Δn = 0.096;
Δε = 8.2.

Use Example 14

| | | |
|---|---|---|
| 4O-B (2CF3, 3F)-O2 | (1-2-9) | 5% |
| 5-HB-F | (12-2) | 12% |
| 6-HB-F | (12-2) | 9% |
| 7-HB-F | (12-2) | 7% |
| 2-HHB-OCF3 | (13-1) | 6% |
| 3-HHB-OCF3 | (13-1) | 7% |
| 4-HHB-OCF3 | (13-1) | 7% |
| 5-HHB-OCF3 | (13-1) | 5% |
| 3-HH2B-OCF3 | (13-4) | 4% |
| 5-HH2B-OCF3 | (13-4) | 4% |
| 3-HHB (F, F)-OCF2H | (13-3) | 3% |
| 3-HHB (F, F)-OCF3 | (13-3) | 4% |
| 3-HH2B (F)-F | (13-5) | 3% |
| 3-HBB (F)-F | (13-23) | 8% |
| 5-HBB (F)-F | (13-23) | 10% |
| 5-HBBH-3 | (4-1) | 3% |
| 3-HB(F) BH-3 | (4-2) | 3% |

NI = 74.2 °C.;
η = 15.2 mPa·s;
Δn = 0.085;
Δε = 4.0.

Use Example 15

| | | |
|---|---|---|
| 3V-B (2CF3, 3F)-O2 | (1-2-20) | 6% |
| 3-HHB (F, F)-F | (13-3) | 9% |
| 3-H2B (F, F)-F | (13-15) | 7% |
| 4-H2B (F, F)-F | (13-15) | 8% |
| 5-H2B (F, F)-F | (13-15) | 7% |
| 3-HBB (F, F)-F | (13-24) | 20% |
| 5-HBB (F, F)-F | (13-24) | 18% |
| 3-H2BB (F, F)-F | (13-27) | 8% |
| 5-HHBB (F, F)-F | (14-6) | 3% |
| 5-HHEBB-F | (14-17) | 2% |
| 3-HH2BB (F, F)-F | (14-15) | 4% |
| 1O1-HBBH-4 | (4-1) | 4% |
| 1O1-HBBH-5 | (4-1) | 4% |

NI = 86.7° C.;
η = 35.7 mPa·s;
Δn = 0.110;
Δε = 8.4.

A pitch was 65.3 micrometers when compound (Op-05) was added to the composition described above at a proportion of 0.25% by weight.

Use Example 16

| | | |
|---|---|---|
| 5-B (2CF3, 3F)-O2 | (1-2-27) | 5% |
| 5-HB-CL | (12-2) | 15% |
| 3-HH-4 | (2-1) | 11% |
| 3-HH-5 | (2-1) | 4% |

-continued

| | | |
|---|---|---|
| 3-HHB-F | (13-1) | 4% |
| 3-HHB-CL | (13-1) | 3% |
| 4-HHB-CL | (13-1) | 4% |
| 3-HHB (F)-F | (13-2) | 9% |
| 4-HHB (F)-F | (13-2) | 8% |
| 5-HHB (F)-F | (13-2) | 8% |
| 7-HHB (F)-F | (13-2) | 7% |
| 5-HBB (F)-F | (13-23) | 3% |
| 1O1-HBBH-5 | (4-1) | 3% |
| 3-HHBB (F, F)-F | (14-6) | 3% |
| 4-HHBB (F, F)-F | (14-6) | 3% |
| 5-HHBB (F, F)-F | (14-6) | 4% |
| 3-HH2BB (F, F)-F | (14-15) | 3% |
| 4-HH2BB (F, F)-F | (14-15) | 3% |

NI = 103.7° C.;
η = 21.0 mPa·s;
Δn = 0.085;
Δε = 3.6.

Use Example 17

| | | |
|---|---|---|
| 2O-B (2F, 3SF5)-O2 | (1-5-1) | 3% |
| 7-HB (F, F)-F | (12-4) | 3% |
| 3-HB-O2 | (2-5) | 7% |
| 2-HHB (F)-F | (13-2) | 10% |
| 3-HHB (F)-F | (13-2) | 10% |
| 5-HHB (F)-F | (13-2) | 8% |
| 2-HBB (F)-F | (13-23) | 9% |
| 3-HBB (F)-F | (13-23) | 9% |
| 5-HBB (F)-F | (13-23) | 15% |
| 2-HBB-F | (13-22) | 4% |
| 3-HBB-F | (13-22) | 4% |
| 5-HBB-F | (13-22) | 3% |
| 3-HBB (F, F)-F | (13-24) | 5% |
| 5-HBB (F, F)-F | (13-24) | 10% |

Use Example 18

| | | |
|---|---|---|
| 2O-B (2SF5, 3SF5)-O2 | (1-6-1) | 3% |
| 3-HB-CL | (12-2) | 12% |
| 3-HH-4 | (2-1) | 12% |
| 3-HB-O2 | (2-5) | 8% |
| 3-HHB (F, F)-F | (13-3) | 3% |
| 3-HBB (F, F)-F | (13-3) | 28% |
| 5-HBB (F, F)-F | (13-3) | 24% |
| 5-HBB (F) B-2 | (4-5) | 5% |
| 5-HBB (F) B-3 | (4-5) | 5% |

Use Example 19

| | | |
|---|---|---|
| 5-B (2SF5, 3SF5)-5 | (1-6-27) | 3% |
| 2-HB-C | (15-1) | 5% |
| 3-HB-C | (15-1) | 12% |
| 3-HB-O2 | (2-5) | 15% |
| 2-BTB-1 | (2-10) | 3% |
| 3-HHB-F | (13-1) | 3% |
| 3-HHB-1 | (3-1) | 7% |
| 3-HHB-O1 | (3-1) | 5% |
| 3-HHB-3 | (3-1) | 13% |
| 3-HHEB-F | (13-10) | 4% |
| 5-HHEB-F | (13-10) | 4% |
| 2-HHB (F)-F | (13-2) | 7% |
| 3-HHB (F)-F | (13-2) | 7% |

-continued

| 5-HHB (F)-F | (13-2) | 7% |
| 3-HHB (F, F)-F | (13-3) | 5% |

INDUSTRIAL APPLICABILITY

A liquid crystal compound of the invention has excellent physical properties. A liquid crystal composition containing the compound can be widely applied to a liquid crystal display device used for a personal computer, a television and so forth.

What is claimed is:

1. A compound, represented by formula (1):

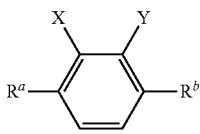
(1)

wherein, in formula (1),
$R^a$ and $R^b$ are independently alkyl having 1 to 30 carbons, and in the groups, at least one —CH$_2$— may be replaced by —O—, —S—, —CO— or —SiH$_2$—, at least one —CH$_2$CH$_2$— may be replaced by —CH=CH— or —C≡C—, and in the monovalent groups, at least one hydrogen may be replaced by fluorine or chlorine; and
X and Y are independently fluoroalkyl having 1 to 5 carbons, fluoroalkoxy having 1 to 5 carbons or pentafluorosulfanil, and one of X and Y may be fluorine.

2. The compound according to claim 1, wherein, in formula (1),
$R^a$ and $R^b$ are independently alkyl having 1 to 20 carbons, and in the groups, at least one —CH$_2$— may be replaced by —O— or —S—, one or two —CH$_2$CH$_2$— groups may be replaced by —CH=CH— or —C≡C—, and in the monovalent groups, at least one hydrogen may be replaced by fluorine or chlorine; and
X and Y are independently fluoroalkyl having 1 to 3 carbons, fluoroalkoxy having 1 to 3 carbons or pentafluorosulfanil, and one of X and Y may be fluorine.

3. The compound according to claim 1, wherein, in formula (1),
$R^a$ and $R^b$ are independently alkyl having 1 to 15 carbons, and in the groups, at least one or two —CH$_2$— groups may be replaced by —O—, one —CH$_2$CH$_2$— may be replaced by —CH=CH— or —C≡C—, and in the monovalent groups, at least one hydrogen may be replaced by fluorine; and
X is fluorine, fluoroalkyl having 1 to 3 carbons, fluoroalkoxy having 1 to 3 carbons or pentafluorosulfanil, and Y is fluoroalkyl having 1 to 3 carbons.

4. The compound according to claim 1, represented by formula (1a):

(1a)

wherein, in formula (1a),
$R^a$ and $R^b$ are independently alkyl having 1 to 10 carbons or alkoxy having 1 to 10 carbons; and Y is —CF$_3$, —CF$_2$H, —CFH$_2$ or fluorine.

5. The compound according to claim 4, wherein, in formula (1a), $R^a$ is alkyl having 1 to 10 carbons and $R^b$ is alkoxy having 1 to 10 carbons; and Y is —CF$_3$.

6. The compound according to claim 1, represented by formula (1b):

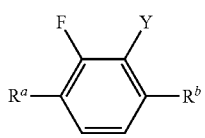
(1b)

wherein, in formula (1b),
$R^a$ and $R^b$ are independently alkyl having 1 to 10 carbons or alkoxy having 1 to 10 carbons; and Y is —CF$_3$, —CF$_2$H or —CFH$_2$.

7. The compound according to claim 6, wherein, in formula (1b), Ra and Rb are independently alkoxy having 1 to 10 carbons; and Y is —CF$_3$.

8. A liquid crystal composition, containing at least one compound according to claim 1.

9. The liquid crystal composition according to claim 8, containing at least one compound selected from the group of compounds represented by formulas (2) to (4):

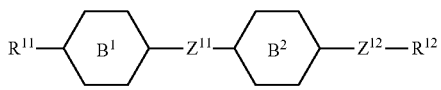
(2)

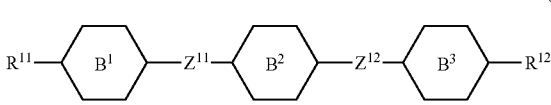
(3)

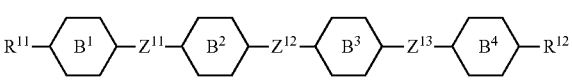
(4)

wherein, in formulas (2) to (4),
$R^{11}$ and $R^{12}$ are independently alkyl having 1 to 10 carbons or alkenyl having 2 to 10 carbons, and in the groups, at least one —CH$_2$— may be replaced by —O—, and in the monovalent groups, at least one hydrogen may be replaced by fluorine;
ring B$^1$, ring B$^2$, ring B$^3$ and ring B$^4$ are independently 1,4-cyclohexylene, 1,4-phenylene, 2-fluoro-1,4-phenylene, 2,5-difluoro-1,4-phenylene or pyrimidine-2,5-diyl; and
$Z^{11}$, $Z^{12}$ and $Z^{13}$ are independently a single bond, —COO—, —CH$_2$CH$_2$—, —CH=CH— or —C≡C—.

10. The liquid crystal composition according to claim 8, further containing at least one compound selected from the group of compounds represented by formulas (5) to (11):

(5)

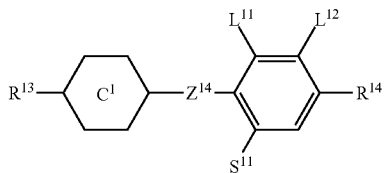

(6)

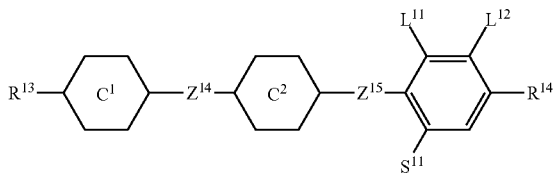

(7)

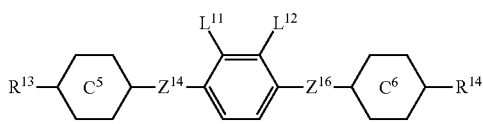

(8)

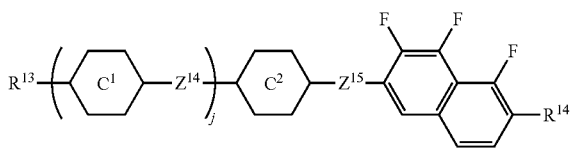

(9)

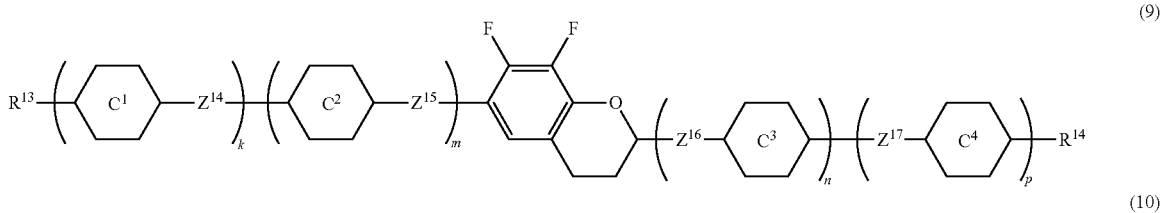

(10)

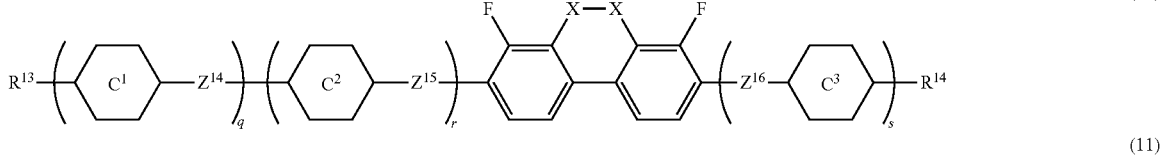

(11)

wherein, in formulas (5) to (11),
- $R^{13}$, $R^{14}$ and $R^{15}$ are independently alkyl having 1 to 10 carbons or alkenyl having 2 to 10 carbons, and in the groups, at least one —$CH_2$— may be replaced by —O—, and in the monovalent groups, at least one hydrogen may be replaced by fluorine, and $R^{15}$ may be hydrogen or fluorine;
- ring $C^1$, ring $C^2$, ring $C^3$ and ring $C^4$ are independently 1,4-cyclohexylene, 1,4-cyclohexenylene, 1,4-phenylene, 1,4-phenylene in which at least one hydrogen is replaced by fluorine, tetrahydropyran-2,5-diyl or decahydronaphthalene-2,6-diyl;
- ring $C^5$ and ring $C^6$ are independently 1,4-cyclohexylene, 1,4-cyclohexenylene, 1,4-phenylene, tetrahydropyran-2,5-diyl or decahydronaphthalene-2,6-diyl;
- $Z^{14}$, $Z^{15}$, $Z^{16}$ and $Z^{17}$ are independently a single bond, —COO—, —$CH_2O$—, —$OCF_2$—, —$CH_2CH_2$— or —$OCF_2CH_2CH_2$—;
- $L^{11}$ and $L^{12}$ are independently fluorine or chlorine;
- $S^{11}$ is hydrogen or methyl;
- X is —CHF— or —$CF_2$—; and
- j, k, m, n, p, q, r and s are independently 0 or 1, a sum of k, m, n and p is 1 or 2, a sum of q, r and s is 0, 1, 2 or 3, and t is 1, 2 or 3.

11. The liquid crystal composition according to claim 8, further containing at least one compound selected from the group of compounds represented by formulas (12) to (14):

(12)

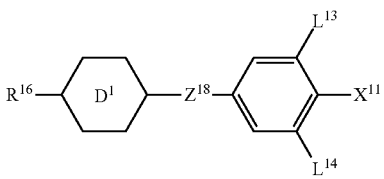

(13)

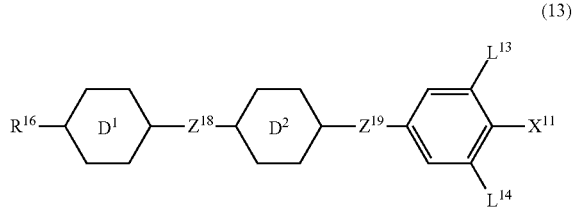

(14)

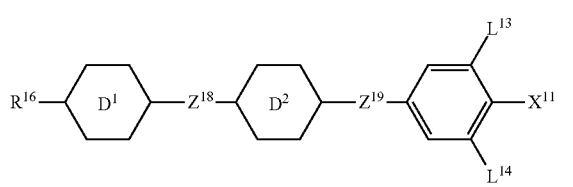

wherein, in formulas (12) to (14), $R^{16}$ is alkyl having 1 to 10 carbons or alkenyl having 2 to 10 carbons, and in the groups, at least one —$CH_2$— may be replaced by —O—, and in the monovalent groups, at least one hydrogen may be replaced by fluorine;

$X^{11}$ is fluorine, chlorine, —$CF_3$, —$CHF_2$, —$CH_2F$, —$OCF_3$, —$OCHF_2$, —$OCF_2CHF_2$ or —$OCF_2CHFCF_3$;

ring $D^1$, ring $D^2$ and ring $D^3$ are independently 1,4-cyclohexylene, 1,4-phenylene, 1,4-phenylene in which at least one hydrogen is replaced by fluorine, tetrahydropyran-2,5-diyl, 1,3-dioxane-2,5-diy or pyrimidine-2,5-diyl;

$Z^{18}$, $Z^{19}$ and $Z^{20}$ are independently a single bond, —COO—, —$CH_2O$—, —$CF_2O$—, —$OCF_2$—, —$CH_2CH_2$—, —CH=CH—, —C≡C— or —$(CH_2)_4$—; and $L^{13}$ and $L^{14}$ are independently hydrogen or fluorine.

12. The liquid crystal composition according to claim 8, further containing at least one compound selected from the group of compounds represented by formula (15):

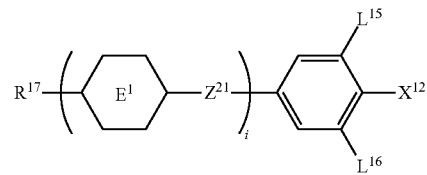

(15)

wherein, in formula (15), $R^{17}$ is alkyl having 1 to 10 carbons or alkenyl having 2 to 10 carbons, and in the groups, at least one —$CH_2$— may be replaced by —O—, and in the monovalent groups, at least one hydrogen may be replaced by fluorine;

$X^{12}$ is —C≡N or —C≡C—C≡N;

ring $E^1$ is 1,4-cyclohexylene, 1,4-phenylene, 1,4-phenylene in which at least one hydrogen is replaced by fluorine, tetrahydropyran-2,5-diyl, 1,3-dioxane-2,5-diyl or pyrimidine-2,5-diyl;

$Z^{21}$ is a single bond, —COO—, —$CH_2O$—, —$CF_2O$—, —$OCF_2$—, —$CH_2CH_2$— or —C≡C—;

$L^{15}$ and $L^{16}$ are independently hydrogen or fluorine; and i is 1, 2, 3 or 4.

13. A liquid crystal display device, including the liquid crystal composition according to claim 8.

* * * * *